US006921641B2

(12) United States Patent
Van Houten et al.

(10) Patent No.: US 6,921,641 B2
(45) Date of Patent: Jul. 26, 2005

(54) THERMOSTABLE UVRA AND UVRB POLYPEPTIDES AND METHODS OF USE

(75) Inventors: Bennet Van Houten, Durham, NC (US); Milan Skorvaga, Durham, NC (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/216,556

(22) Filed: Aug. 10, 2002

(65) Prior Publication Data

US 2003/0073113 A1 Apr. 17, 2003

Related U.S. Application Data

(60) Provisional application No. 60/311,336, filed on Aug. 10, 2001.

(51) Int. Cl.[7] .................................................. C12Q 1/68
(52) U.S. Cl. .............................. 435/6; 435/15; 435/183; 435/194; 530/350; 536/23.1; 536/23.2
(58) Field of Search .................................. 435/183, 194, 435/6, 15; 530/350; 536/23.1, 24.3

(56) References Cited

U.S. PATENT DOCUMENTS

| 5,114,551 A | 5/1992 | Hjerten et al. | .............. 204/452 |
| 6,132,968 A | 10/2000 | Le et al. | ........................ 435/6 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492–495.*
Abrahams et al., "Methods Used in the Structure of Determination of Bovine Mitochondrial $F_1$ ATPase," *Acta Crystallogr. D.*, 1997;52:30–42.
Amelunxen et al., "Mechanisms of Thermophily," *CRC Crit. Rev. Microbiol.*, 1978;6:343–393.
Argos et al., "Thermal Stability and Protein Structure," *UCLA Forum Med. Sci.*, 1979;21:159–169.
Bailey, "The CCP4 Suite: Programs for Protein Crystallography," *Acta Crystallogr. D.*, 1994;50:760–763.
Barton, Geoffrey J., "ALSCIPT: a tool to format multiple sequence alignments," *Protein Eng.*, 1993;6(1):37–40.
Belagaje et al., "Increased production of low molecular weight recombinant proteins in *Escherichia coli*," *Protein Science*, 1997;6:1953–1962.
Bertrand-Burggraf et al., "Identification of the Different Intermediates in the Interaction of (A)BC Excinuclease with its Substrates by DNase I Footprinting on two Uniquely Modified Oligonucleotides," *J. Mol. Biol.*, 1991;219:27–36.
Brandsma et al., "Identification of the uvrA6 Mutation of *Escherichia coli*," *J. Bacteriol.*, 1988;170:1012–1014.
Brock, T.D., "Life at High Temperatures," *Science*, Oct. 11, 1985;230:132–138.

Brünger, "X–PLOR Version 3.1A System for X-ray Crystallography and NMR," Yale University Press, New Haven, CT, 1992.
Bult et al., "Complete Genome Sequence of the Methanogenic Archaeon, *Methanococcus jannaschii*," *Science*, Aug. 23, 1996;273: 1058–1073.
Caron et al., "Involvement of a cryptic ATPase activity of UvrB and its proteolysis product, UvrB* in DNA repair," *Nucleic Acids Res.*, 1998;16(20):9651–9662.
Caron et al., "Involvement of cryptic ATPase activity of UvrB and is proteolysis product, UvrB* in DNA repair," *Nucleic Acids Res.*, 1988;16(22):10891–10902.
Chambers et al., "Physical characterization and over–expression of the *Bacillus caldotenax* superoxide dismutase gene," *FEMS Microbiol. Lett.*, 1992;70:277–284.
Choi et al., "Site Specific Benzo[a]pyrene Diol Epoxide–DNA Adducts Inhibit Transcription Elongation by Bacteriophage T7 RNA Polymerase," *Biochemistry*, 1994;33:780–787.
Chong et al., "Protein Splicing Involving the *Saccharomyces cerevisiae* VMA Intein," *J. Biol. Chem.*, Sep. 6, 1996;271:22159–22168.
Chong et al., "Single–column purification of free recombinant proteins using a self–cleavable affinity tag derived from a protein splicing element," *Gene*, 1997;192:277–281.
Chong et al., "Utilizing the C–terminal cleavage activity of a protein splicing element to purify recombinant proteins in a single chromatographic step," *Nucl. Acids Res.*, 1998;26(22):5109–5115.
Chong et al., "Modulation of Protein Splicing of the *Saccharomyces cerevisiae* Vacuolar Membrane ATPase Intein," *J. Biol. Chem.*, Apr. 24, 1998;273:10567–10577.
Claassen et al., "Deletion of Mutagenesis of the *Escherichia coli* UvrA Protein Localizes Domains for DNA Binding, Damage Recognition, and Protein–Protein Interactions," *J. Biol. Chem.*, Jun. 15, 1991;266:11388–11394.
Deckert et al., "The complete genome of the hyperthermophilic bacterium *Aquifex aeolicus*," *Nature*, 1998;392:353–358.
De La Fortelle et al., "[27] Maximum–Likelihood Heavy–Atom Parameter Refinement for Multiple Isomorphous Replacement and Mutliwavelength Anomalous Diffraction Methods," *Methods Enzymol.*, 1997;276:472–494.

(Continued)

*Primary Examiner*—Richard Hutson
(74) *Attorney, Agent, or Firm*—Mueting, Raasch & Gebhardt, P.A.

(57) ABSTRACT

The present invention provides thermostabile UvrA polypeptides, thermostable UvrB polypeptides and the polynucleotides that encode the UvrA and UvrB polypeptides. The invention also includes compositions and kits containing the UvrA and UvrB polypeptides of the present invention. Also provided by the present invention are methods of detecting DNA damage using the UvrA and UvrB polypeptides.

17 Claims, 19 Drawing Sheets

OTHER PUBLICATIONS

Delagoutte et al., "Sequence–dependent Modulation of Nucleotide Excision Repair: The Efficiency of the Incision Reaction is Inversely Correlated with the Stability of the Pre–incision UvrB–DNA Complex," *J. Mol. Biol.*, 1997;266:703–710.

Doig et al., "Why Water–Soluble, Compact, Globular Proteins Have Similar Specific Enthalpies of Unfolding at 110° C.," *Biochemistry*, 1992;31:9371–9375.

Dubendorff et al., "Controlling Basal Expression in an Inducible T7 Expression System by Blocking the Target T7 Promoter with lac Repressor," *J. Mol. Biol.*, 1991;219:45–59.

Friedberg et al., *DNA Repair and Mutagenesis*, American Society of Microbiological Press, Washington, D.C., 1995.

Goding, J., "Monoclonal Antibodies: Principles and Practice," 3rd Edition, Academic Press, 1996.

Gorbalenya et al., "Two related superfamilies of putative helicases involved in replication, recombination, repair and expression of DNA and RNA genomes," *Nucleic Acids Res.*, 1989;17(12):4713–4730.

Harlow et al., *Antibodies: A Laboratory Manual*, Cold Spring Harbor Laboratory Press, Cold Spring Harbor, NY; title page, publisher's page, and table of contents, 9 pages (1988).

Heinen, W., "Growth Conditions and Temperature–Dependent Substrate Specificity of Two Extremely Thermophilic Bacteria," *Arch Mikrobiol.*, 1971;76:2–17.

Hiramatsu et al., "Cloning and characterization of the uvrD gene from an extremely thermophilic bacterium, *Thermus thermophilus* HB8," *Gene*, 1997;199:77–82.

Ho et al., "Site–directed mutagenesis by overlap extension using the polymerase chain reaction," *Gene*, 1989;77:51–59.

Holm et al., "Dali: a network tool for protein structure comparison," *Trends Biochem. Sci.*, 1995;20:478–480.

Hsu et al., "Structure and Function of the UvrB Protein," *J. Biol. Chem.*, 1995 Apr. 7;270:8319–8327.

Husain et al., "Sequences of *Escherichia coli* uvrA Gene and Protein Reveal Two Potential ATP Binding Sites," *J. Biol. Chem.*, Apr. 15, 1986;261:4895–4901.

Ikemura, T., "Correlation between the Abundance of *Escherichia coli* Transfer RNAs and the Occurrence of the Respective Codons in its Protein Genes," *J. Mol. Biol.*, 1981;146:1–21.

Jones et al., "Improved Methods for Building Protein Models in Electron Density Maps and the Location of Errors in these Models," *Acta Crystallogr. A.*, 1991;47:110–119.

Jung et al., "Metabolic Differences in *Bacillus stearothermophilus* Grown at 55° C. and 37° C.," *Arch. Mikrobiol.*, 1974;95:125–138.

Kacinski et al., "A general approach for purifying proteins encoded by cloned genes without using a functional assay: isolation of the uvrA gene product from radiolabeled maxicells," *Nucleic Acids Res.*, 1981;9(18):4495–4508.

Kato et al., "RecA Protein from an Extremely Thermophilic Bacterium, *Thermus thermophilus* HB8," *J. Biochem (Tokyo)*, 1993;114:926–929.

Kato et al., "ATPase Activity of UvrB Protein from *Thermus thermophilus* HB8 and its Interaction with DNA," *J. Biol. Chem.*, 1996;271:9612–9618.

Kim et al., "Hepatitis C virus NS3 RNA helicase domain with a bound oligonucleotide: the crystal structure provides insights into the mode of unwinding," *Structure*, 1998;6:89–100.

Klenk et al., "The Complete genome sequence of the hyperthermophilic, sulphate–reducing archaeon *Archaeoglobus fulgidus*," Nature, Nov. 27, 1997;310:364–370.

Köhler et al., "Derivation of specific antibody–producing tissue culture and tumor lines by cell fusion," *Eur. J. Immunol.*, 1976;6:511–519.

Koo et al., "ATP–dependent partitioning of the DNA template into supercoiled domains by *Escherichia coli* UvrAB," *Proc. Natl. Acad. Sci. U.S.A.*, Feb. 1991;88:1212–1216.

Kuramitsu et al., "Pre–Steady–State Kinetics of *Escherichia coli* Aspartate Aminotransferase Catalyzed Reactions and Thermodynamic Aspects of Its Substrate Specificity," *Biochemistry*, 1990;29:5469–5476.

Kushner, "DNA Repair," Ingraham et al., *Escherichia coli and Salmonella typhimurium cellular and molecular biology*, Washington, D.C.,1987;1044–1053.

Lin et al., "Reconstitution of Nucleotide Excision Nuclease with UvrA and UvrB Proteins from *Escherichia coli* and UvrC Protein from *Bacillus subtilis,"* *J. Biol. Chem.*, Dec. 5, 1990;265:21337–21341.

Lin et al., "Active Site of (A)BC Excinuclease," *J. Biol. Chem.*, Sep. 5, 1992; 267:17693–17700.

Lin et al., "Active Site of (A)BC Excinuclease" *J. Biol. Chem.*, Sep. 5, 1992;267:17688–17692.

Ljungdahl, L.G., "Physiology of Thermophilic Bacteria," *Advances in Microbial Physiology*, Academic Press, New York, NY, 1979;I19:168–172.

Lopez–Camacho et al., "Amino acid substitutions enhancing thermostability of *Bacillus polymyxa* β–glucosidase A," *Biochem. J.*, 1996;314:833–838.

Machius et al., "Crystal structure of the NDA nucleotide excision repair enzyme UvrB from *Thermus thermophilus*," *Proc. Natl. Acad. Sci. U.S.A.*, 1999;96:11717–11722.

Marmur, J., "A Procedure for the Isolation of Deoxyribonucleic Acid from Micro–organisms," *J. Mol. Biol.*, 1961;3:208–218.

Matthews et al., "Effect of Single Amino Acid Substitutions on the Thermal Stability of the α Subunit of Tryptophan Synthase," *Biochemistry*, 1980;19:1290–1293.

Mazur et al., "Dimerization of *Escherichia coli* UvrA and Its Binding to Undamaged and Ultraviolet Light Damaged DNA," *Biochemistry*, 1991;30:4432–4443.

Merkler et al., "Protein Thermostability," *Int. J. Pept. Protein Res.*, 1981;18:430–442.

Miroux et al., "Over–production of Proteins in *Escherichia coli*: Mutant Hosts that Allow Synthesis of some Membrane Proteins and Globular Proteins at High Levels," *J. Mol. Biol.*, 1996;260:289–298.

Moolenaar et al., "Helicase Motifs V and VI of the *Escherichia coli* UvrB Protein of the UvrABC Endonuclease Are Essential for the Formation of the Preincision Complex," *J. Mol. Biol.*, 1994;240:294–307.

Moolenaar et al., "The C–terminal Region of the UvrB Protein of *Escherichia coli* Contains an Important Determined for UvrC Binding to the Preincision Complex but Not the Catalytic Site for 3'–Incision," *J. Biol. Chem.*, Dec. 22, 1995;270: 30508–30515.

Murshudov et al., "Refinement of Macromolecular Structures by the Maximum–Likelihood Method," *Acta Crystallogr. D.*, 1997;53:240–255.

Myles et al., "DNA Repair," *Chem. Res. Toxicol.*, Jul./Aug. 1989;2(4):197–226.

Myles et al., "Site–Specific Mutagenesis of Conserved Residues within Walker A and B Sequences of *Escherichia coli* UvrA Protein," *Biochemistry*, 1991;30:3824–3834.

Myles et al., "Isolation and Characterization of Functional Domains of UvrA," *Biochemistry*, 1991;30:3834–3840.

Navaratnam et al., "Evidence from Extended X–ray Absorption Fine Structure and Site–Specific Mutagenesis for Zinc Fingers in UvrA Protein of *Escherichia coli*," *J. Biol. Chem.*, Sep. 25, 1989;264:16067–16071.

Nelson et al., "Evidence for lateral gene transfer between Archaea and Bacteria from genome sequence of *Thermotoga maritima*," *Nature*, May 27, 1999;399:323–329.

Ochman et al., "Genetic Applications of an Inverse Polymerase Chain Reaction," *Genetics*, 1988;120:621–623.

Oh et al., "Helicase properties of the *Escherichia coli* UvrAB protein complex," *Proc. Natl. Acad. Sci. U.S.A.*, Jun. 1987;84:3638–3642.

Oh et al., "Characterization of the Helicase Activity of the *Escherichia coli* UvrAB Protein Complex," *J. Biol. Chem.*, Jan. 15, 1989;264:1336–1343.

Oh et al., "ATPase activity of the UvrA and UvrAB protein complexes of the *Escherichia coli* UvrABC endonuclease," *Nuclei Acids Res.*, 1989;17(11):4145–4159.

Okamoto et al., "An Asparate Aminotransferase from an Extremely Thermophilic Bacterium, *Thermus thermophilus* HB8," *J. Biochem (Tokyo)*, 1996;119:135–144.

Orren et al., "The (A)BC excinuclease of *Escherichia coli* has only the UvrB and UvrC subunits in the incision complex," *Proc. Natl. Acad. Sci. U.S.A.*, Jul. 1989;86:5237–5241.

Orren et al., "Formation and Enzymatic Properties of the UvrB–DNA Complex," *J. Biol. Chem.*, Sep. 15, 1990;265:15796–15803.

Orren et al., "Post–incision Steps of Nucleotide Excision Repair in *Escherichia coli* Disassembly of the UvrBC–DNA Complex by Helicase II and DNA Polymerase I," *J. Biol. Chem.*, Jan. 15, 1992;267:780–788.

Otwinowski et al., "Processing of X–Ray Diffraction Data Collected in Oscillation Mode," *Methods Enzymol.*, 1997;276:307–326.

Rost et al., "Prediction of Protein Secondary Structure at Better than 0% Accuracy," *J. Mol. Biol.*, 1993;232:584–599.

Sambrook et al., *Molecular Cloning: A Laboratory Manual*, Cold Spring Harbor Laboratory, Cold Spring Harbor, NY, 1989.

Sancar et al., *DNA Repair: A Laboratory Manual of Research Procedures*, 1987;3:481–510.

Sancar et al., "DNA Repair Enzymes," *Annu. Rev. Biochem*, 1988;57:29–67.

Seeberg et al., "Purification and Properties of the uvrA protein from *Escherichia coli*," *Proc. Natl. Acad. Sci. U.S.A.*, Feb. 1982;79:988–992.

Seeley et al., "Mutations in the *Escherichia coli* UvrB ATPase Motif compromise excision repair capacity," *Proc. Natl. Acad. Sci. U.S.A.*, Sep. 1989;86:6577–6581.

Sellmann et al., "Purification and Characterization of DNA Polymerases from *Bacillus* Species," *J. Bacteriol*, 1992;174:4350–4355.

Sharp et al., *Applied Microbial Physiology: A Practical Approach*, Rhodes and Stanbury, Oxford, U.K., 1997;23–52.

Sheldrick, "Phase Annealing in SHELX–90: Direct Methods for Larger Structures," *Acta Crystallogr. A.*, 1990;46:467–473.

Shi et al., "Electron Microscopic Study of (A)BC Excinuclease DNA is Sharply Bent in the UvrB–DNA Complex," *J. Mol. Biol.*, 1992;226:425–432.

Silver et al., "Novel Use of Polymerase Chain Reaction to Amplify Cellular DNA Adjacent to an Integrated Provirus," *J. Virol.*, May 1989;63(5):1924–1928.

Skorvaga et al., "The β–Hairpin Motif of UvrB Is Essential for DNA Binding, Damage Processing, and UvrC–mediated Incisions," *J. Biol. Chem.*, 2002;277:1553–1559.

Smith et al., "Complete Genome Sequence of *Methanobacterium thermoautotrophicum* ΔH: Functional Analysis and Comparative Genomics," *J. Bacteriol.*, 1997;179:7135–7155.

Snowden et al., "Initiation of the UvrABC Nuclease Cleavage Reaction Efficiency of Incisions is not Correlated with UvrA Binding Affinity," *J. Mol. Biol.*, 1991;220:19–33.

Soultanas et al., "DNA Binding Mediates Conformational Changes and Metal Ion Coordination in the Active Site of PcrA Helicase," *J. Mol. Biol.*, 1999;290:137–148.

Studier et al., "Use of Bacteriophage T7 RNA Polymerase to Direct Selective High–level Expression of Cloned Genes," *J. Mol. Biol.*, 1986;189:113–130.

Sung et al., "RAD3 protein of *Saccharomyces cerevisiae* is a DNA helicase," *Proc. Natl. Acad. Sci. U.S.A.*, Dec. 1987;84:8951–8955.

Sung et al., "Human xeroderma plgmentosum group D gene encodes a DNA helicase," *Nature*, 1993;365:852–855.

Tatusova et al., "BLAST 2 Sequences, a new tool for comparing protein and nucleotide sequences," *FEMS Microbiol. Lett.*, 1999;174:247–250.

Takamatsu et al., "Mismatch DNA recognition protein from an extremely thermophilic bacterium, *Thermus thermophilus* HB8," *Nucleic Acids Res.*, 1996;24:640–647.

Theis et al., "Crystal structure of UvrB, a DNA helicase adapted for nucleotide excision repair," *EMBO Journal*, 1999;18(24):6899–6907.

Theis et al., "The nucleotide excision repair protein UvrB, a helicase–like enzyme with a catch," *Mutation Research*, 2000;460:277–300.

Thiagalingam et al., "Both ATPase Sites of *Escherichia coli* UvrA Have Functional Roles in Nucleotide Excision Repair," *J. Biol. Chem.*, Jun. 15, 1991;266:11395–11403.

Thomas et al., "Amplification and Purification of UvrA, UvrB, and UvrC Proteins of *Escherichia coli*," *J. Biol. Chem.*, Aug. 15, 1985;260:9875–9883.

Thompson et al., "CLUSTAL W: improving the sensitivity of progressive multiple sequence alignment through sequence weighting, position–specific gap penalties and weight matrix choice," *Nucl. Acids Res.*, 1994;22:4673–4680.

Triglia et al., "A procedure for in vitro amplification of DNA segments that lie outside the boundaries of known sequences," *Nucleic Acids Res.*, 1988;16:8186.

Uemori et al., "Cloning of the DNA Polymerase Gene of *Bacillus caldotenax* and Characterization of the Gene Product," *J. Biochem. (Tokyo)*, 1993;113:401–410.

Van Houten, B., "Nucleotide Excision Repair in *Escherichia coli*," *Microbiol. Rev.*,1990;54:18–51.

Van Houten et al., "Mechanism of Action of the *Escherichia coli* UvrABC Nuclease: Clues to the Damage Recognition Problem," *BioEssays*, 1993;15:51–59.

Vassylyev et al., "Atomic Model of a Pyrimidine Dimer Excision Repair Enxyme Complexed with a DNA Substrate: Structural Basis for Damaged DNA Recognition," *Cell*, Dec. 1, 1995;83:773–782.

Velankar et al., "Crystal Structures of Complexes of PcrA DNA Helicase with a DNA Substrate Indicate an Inchworm Mechanism," *Cell*, Apr. 2, 1999;97:75–84.

Visse et al., "Uvr Excision Repair Protein Complex of *Escherichia coli* Binds to the Convex Side of a Cisplatin–induced Kink in the DNA," *J. Biol. Chem.*, Apr. 25, 1991;266:7609–7617.

Visse et al., "The Actual Incision Determines the Efficiency of Repair of Cisplatin–Damaged DNA by the *Escherichia coli* UvrABC Endonuclease," *Biochemistry*, 1994;33:1804–1811.

Visse et al., "Protein–DNA Interactions and Alterations in the DNA Structure upon UvrB–DNA Preincision Complex Formation during Nucleotide Excision Repair in *Escherichia coli*," *Biochemistry*, 1994;33:9881–9888.

Walker et al., "Distantly related sequences in the α– and β–subunits of ATP synthase, myosin, kinases and other ATP–requiring enzymes and a common nucleotide binding fold," *EMBO J.*, 1982;1:945–951.

Watanabe et al., "Multiple proline substitutions cumulatively thermostabilize *Bacillus cereus* ATCC7064 oligo–1, 6–glucosidase," *Eur. J. Biochem.*, 1993;226:277–283.

Xian et al., "DNA–protein binding assays from a single sea urchin egg: A high–sensitivity capillary electrophoresis methods," *Proc. Natl. Acad. Sci. U.S.A.*, 1996;93:86–90.

Yamamoto et al., "Cloning, sequencing and expression of the uvrA gene from an extremely thermophilic bacterium, *Thermus thermophilus* HB8," *Gene*, 1996;171:103–106.

Zou et al., "Interaction of the UvrAVC Nuclease System with a DNA duplez Containing a Single Stereoisomer of dG–(+)– or dG–(–)–anti–BPDE," *Biochemistry*, 1995;34:13582–13593.

Zou et al., "Formation of DNA Repair Intermediates and Incision by the ATP–dependent UvrB–UvrC Endonuclease," *J. Biol. Chem.*, 1997;272:4820–4827.

Zou et al., "Involvement of Molecular Chaperonins in Nucleotide Excision Repair," *J. Biol. Chem.*, May 22, 1998;273:12887–12892.

Zou et al., "Hydrophobic Forces Dominate the Thermodynamic Characteristics of UvrA–DNA Damage Interactions," *J. Mol. Biol.*, 1998;281:107–119.

Zou et al., "Strand opening by the UvrA$_2$B complex allows dynamic recongnition of DNA damage," *EMBO J.*, 1998;18(17): 4889–4901.

Zulli et al., "Engineering Thermostability and Activity of Lactate Dehydrogenases from Bacilli," *Biol. Chem. Hoppe Seyler*, 1991;372:363–372.

National Center for Biotechnology Information, National Library of Medicine, National Institutes of Health, GenBank Locus F69729, Accession No. F69729, "Excinuclease ABC Chain A– *Bacillus subtilis*," [online]. Bethesda, MD [retrieved on Apr. 16, 2003]. Retrieved from the Internet <URL:http://www.ncbi.nlm.nih.gov/entrez/query-.fcgi?cmd=Retrieve&db=protei n&list_uids= 7442691&dopt=GenPept>; 3 pgs.

National Center for Biotechnology Information, National Library of Medicine, National Institutes of Health, GenBank Locus P07025, Accession No. P07025, "UvrABC System protein B (UvrB protein) (Excinuclease ABC subunit B)," [online]. Bethesda, MD [retrieved on Apr. 16, 2003]. Retrieved from the Internet <URL:http://www.ncbi.nlm.nih.gov/entrez/query.fcgi?cmd=Retrieve&db=protei n&list_uids=137190&dopt=GenPept>; 6 pgs.

National Center for Biotechnology Information, National Library of Medicine, National Institutes of Health, GenBank Locus G69729, Accession No. G69729, "Excinuclease ABC cahing B—*Bacillus subtilis*," [online]. Bethesda, MD [retrieved on Apr. 16, 2003]. Retrieved from the Internet <URL:http://www.ncbi.nlm.nih.gov/entrez/query-.fcgi?cmd=Retrieve&db=protei n&list_uids= 7443925&dopt=GenPept>; 3 pgs.

National Center for Biotechnology Information, National Library of Medicine, National Institutes of Health, GenBank Locus P07028, Accession No. P07028, "UvrABC System protein C (UvrC protein) (Excinuclease ABC subunit C)," [online]. Bethesda, MD [retrieved on Apr. 16, 2003]. Retrieved from the Internet <URL:http://www.ncbi.nlm.nih.gov/entrez/query.fcgi?cmd=Retrieve&db=protei n&list_uids=29429164&dopt=GenPep>; 6 pgs.*

National Center for Biotechnology Information, National Library of Medicine, National Institutes of Health, GenBank Locus P14951, Accession No. P14951, "Excinuclease ABC subunit C)," [online]. Bethesda, MD [retrieved on Apr. 16, 2004]. Retrieved from the Internet <URL:http://www.ncbi.nlm.nih.gov/entrez/query.fcgi?cmd=Retrieve&db= protei n&list_uids=137192&dopt=GenPept>; 4 pgs.*

National Center for Biotechnology Information, National Library of Medicine, National Institutes of Health, GenBank Locus AY028962, Accession No. AY028962, "Characterization of thermophilic UvrA from *Bacillus caldotenax*," [online]. Bethesda, MD [retrieved on Jul. 28, 2003]. Retrieved from the Internet <URL:http://www.ncbi.nlm.nih.gov/entrez/query.fcgi?cmd=Retrieve&db=nucleo tide&list_uids= 13591421&dopt=GenPept>; 3 pgs.*

Gordienko et al., "The limited strand–separating of the UvrAB protein complex and its role in the recognition of DNA damage," *EMBO J*, 1997;16:889–895.*

Myles and Sancur, "Isolation and Characterization of Functional Domains of UvrA," *Biochemistry*, 1991;30: 3834–3840.*

National Center for Biotechnology Information, National Library of Medicine, National Institutes of Health, GenBank Locus AF017113, Accession No. AF017113, "Nucleotide Sequence of the 300–304 Chromosomal Segment of Bacillus Subtilis is Required for Spore Germination," [online]. Bethesda, MD [Dec. 8, 2003]. Retrieved from the Internet:<URL:www.ncbi.nlm.nih.gov/entrez/query-.fcgi?cmd=retrieve&db=nucl eotide&list_uids= 2618830&dopt=GenBank&term=AF017113&qty=1>; 36 pgs.

* cited by examiner

Fig. 1

```
SEQ ID NO:1  ATG GAT AAA ATT GTC GTC AAA GGG GCG CGC GCC CAC AAC TTG AAA      45
SEQ ID NO:2   M   D   K   I   V   V   K   G   A   R   A   H   N   L   K

AAC ATT GAC GTC GAA ATC CCG CGC GGC AAG CTC GTG GTC TTG ACC      90
              N   I   D   V   E   I   P   R   G   K   L   V   V   L   T

GGG CTG TCC GGG TCG GGG AAG TCG TCG CTG GCG TTT GAT ACG ATT     135
              G   L   S   G   S   G   K   S   S   L   A   F   D   T   I

TAC GCG GAA GGC CAG CGC CGC TAC GTC GAA TCG CTG TCG GCG TAT     180
              Y   A   E   G   Q   R   R   Y   V   E   S   L   S   A   Y

GCC CGC CAG TTT TTA GGG CAG ATG GAA AAA CCG GAC GTC GAT GCG     225
              A   R   Q   F   L   G   Q   M   E   K   P   D   V   D   A

ATT GAA GGG TTG TCG CCG GCC ATT TCG ATC GAT CAA AAA ACG ACG     270
              I   E   G   L   S   P   A   I   S   I   D   Q   K   T   T

AGC CGC AAC CCG CGC TCA ACC GTC GGC ACG GTG ACG GAA ATT TAC     315
              S   R   N   P   R   S   T   V   G   T   V   T   E   I   Y

GAT TAT TTA CGG CTG CTG TTC GCC CGC ATC GGC CGC CCA GTT TGC     360
              D   Y   L   R   L   L   F   A   R   I   G   R   P   V   C

CCG ACG CAC GGC ATT GAA ATC CAA TCG CAG ACG ATC GAG CAA ATG     405
              P   T   H   G   I   E   I   Q   S   Q   T   I   E   Q   M

GTC GAC CGG TTG CTC GCT TAC CCG GAG CGG ACG AAA ATG CAA ATT     450
              V   D   R   L   L   A   Y   P   E   R   T   K   M   Q   I

TTG GCG CCG ATC GTC TCG GGA AAA AAA GGG ACG CAC GCC AAG ACA     495
              L   A   P   I   V   S   G   K   K   G   T   H   A   K   T

TTG GAG GAT ATT CGC AAA CAA GGG TAT GTG CGC GTC CGC ATT GAC     540
              L   E   D   I   R   K   Q   G   Y   V   R   V   R   I   D

GGC GAG ATG CGC GAG TTG ACG GAG GAC ATT GAG CTG GAA AAA AAC     585
              G   E   M   R   E   L   T   E   D   I   E   L   E   K   N

AAA AAA CAT TCG ATT GAT GTC GTC GTC GAC CGC ATC ATC ATC AAA     630
              K   K   H   S   I   D   V   V   V   D   R   I   I   I   K

GAC GGC ATC GCC GCC AGG CTT GCC GAT TCG CTT GAG ACG GCG CTG     675
              D   G   I   A   A   R   L   A   D   S   L   E   T   A   L

AAG CTC GCC GAC GGC AAA GTG GTC GTT GAC GTG ATC GGC GAG GGG     720
              K   L   A   D   G   K   V   V   V   D   V   I   G   E   G

GAG CTC TTG TTC AGC GAA AAG CAC GCT TGT CCG TAC TGC GGC TTT     765
              E   L   L   F   S   E   K   H   A   C   P   Y   C   G   F

TCG ATC GGG GAG CTT GAA CCG CGT CTG TTT TCG TTC AAC AGT CCA     810
              S   I   G   E   L   E   P   R   L   F   S   F   N   S   P

TTC GGC GCC TGC CCG GAC TGC GAC GGG CTC GGG GCG AAG CTC GAA     855
              F   G   A   C   P   D   C   D   G   L   G   A   K   L   E

GTG GAT CTC GAT TTG GTC ATC CCG AAC GAT GAG CTG ACG TTA AAA     900
              V   D   L   D   L   V   I   P   N   D   E   L   T   L   K

GAA CAC GCC ATC GCT CCG TGG GAG CCG CAA AGC TCG CAA TAT TAC     945
              E   H   A   I   A   P   W   E   P   Q   S   S   Q   Y   Y

CCG CAG CTG CTC GAA GCC GTG TGC CGC CAT TAC GGC ATC CCG ATG     990
              P   Q   L   L   E   A   V   C   R   H   Y   G   I   P   M

GAC GTG CCG GTC AGA GAT TTG CCG AAA GAG CAG CTC GAT AAA ATT    1035
              D   V   P   V   R   D   L   P   K   E   Q   L   D   K   I
```

SEQ ID NO:1-2, continued

```
TTG TAC GGC AGC GGC GGA GAG CCG ATT TAT TTC CGC TAT ACG AAT    1080
 L   Y   G   S   G   G   E   P   I   Y   F   R   Y   T   N

GAT TTC GGA CAA GTG CGC GAA CAA TAC ATC GCA TTT GAA GGC GTC    1125
 D   F   G   Q   V   R   E   Q   Y   I   A   F   E   G   V

ATT CCG AAC GTC GAA CGC CGC TAT CGC GAG ACG AGC TCG GAC TAC    1170
 I   P   N   V   E   R   R   Y   R   E   T   S   S   D   Y

ATC CGC GAG CAG ATG GAA AAG TAT ATG GCG GAA CAA CCA TGT CCG    1215
 I   R   E   Q   M   E   K   Y   M   A   E   Q   P   C   P

ACA TGC CAA GGC TAC CGG CTG AAA AAA GAA AGC CTG GCC GTC CTT    1260
 T   C   Q   G   Y   R   L   K   K   E   S   L   A   V   L

GTC GGC GGC AAG CAT ATC GGC GAG GTC ACC GCC ATG TCG GTG ACC    1305
 V   G   G   K   H   I   G   E   V   T   A   M   S   V   T

GAG GCG CTC GCC TTT TTT GAC GGG CTC GAG CTG ACC GAA AAA GAA    1350
 E   A   L   A   F   F   D   G   L   E   L   T   E   K   E

GCG CAA ATC GCC CGC CTT ATT TTG CGT GAA ATT CGC GAC CGG CTC    1395
 A   Q   I   A   R   L   I   L   R   E   I   R   D   R   L

GGC TTT TTG CAA AAC GTC GGC CTC GAC TAT TTG ACG CTC AGC CGC    1440
 G   F   L   Q   N   V   G   L   D   Y   L   T   L   S   R

TCG GCA GGA ACG CTC TCC GGC GGC GAG GCG CAG CGC ATC CGC TTG    1485
 S   A   G   T   L   S   G   G   E   A   Q   R   I   R   L

GCG ACG CAG ATC GGC TCG CGG CTG ACG GGG GTG CTG TAC GTG CTC    1530
 A   T   Q   I   G   S   R   L   T   G   V   L   Y   V   L

GAC GAG CCG TCG ATC GGG CTT CAT CAG CGC GAC AAC GAC CGG CTG    1575
 D   E   P   S   I   G   L   H   Q   R   D   N   D   R   L

ATC GCG ACG TTG AAA AGC ATG CGC GAC CTC GGC AAT ACG CTC ATT    1620
 I   A   T   L   K   S   M   R   D   L   G   N   T   L   I

GTG GTG GAG CAC GAC GAG GAT ACC ATG CTG GCC GCG GAC TAT TTG    1665
 V   V   E   H   D   E   D   T   M   L   A   A   D   Y   L

ATT GAC ATT GGT CCG GGG GCG GGC ATC CAC GGC GGC GAA GTC ATA    1710
 I   D   I   G   P   G   A   G   I   H   G   G   E   V   I

TCT GCG GGT ACG CCG GAA GAA GTG ATG GAA GAT CCA AAT TCA TTA    1755
 S   A   G   T   P   E   E   V   M   E   D   P   N   S   L

ACG GGC AGC TAT TTA TCG GGG AAA AAA TTT ATC CCA TTG CCT CCT    1800
 T   G   S   Y   L   S   G   K   K   F   I   P   L   P   P

GAA AGA AGA AAG CCG GAC GGA CGT TAC ATT GAA ATT AAA GGC GCG    1845
 E   R   R   K   P   D   G   R   Y   I   E   I   K   G   A

CGC GAG CAT AAC TTG AAA AAC GTA TCG GTG AAA ATC CCG CTC GGC    1890
 R   E   H   N   L   K   N   V   S   V   K   I   P   L   G

ACG TTT GTC GCT GTC ACC GGG GTG TCG GGC TCG GGC AAA AGC ACG    1935
 T   F   V   A   V   T   G   V   S   G   S   G   K   S   T

CTT GTG AAC GAA GTG TTG TAT AAG GCG CTG GCG CAA AAG CTG CAC    1980
 L   V   N   E   V   L   Y   K   A   L   A   Q   K   L   H

CGG GCG AAG GCG AAA CCG GGC GAG CAC CGC GAC ATT CGC GGG CTG    2025
 R   A   K   A   K   P   G   E   H   R   D   I   R   G   L

GAG CAT CTC GAT AAA GTC ATT GAC ATC GAC CAG TCG CCG ATC GGC    2070
 E   H   L   D   K   V   I   D   I   D   Q   S   P   I   G
```

SEQ ID NO:1-2, continued

```
CGC ACG CCA CGC TCG AAC CCG GCG ACG TAC ACC GGG GTG TTT GAC    2115
 R   T   P   R   S   N   P   A   T   Y   T   G   V   F   D

GAC ATC CGC GAC GTG TTT GCC TCG ACG AAC GAA GCG AAA GTG CGC    2160
 D   I   R   D   V   F   A   S   T   N   E   A   K   V   R

GGC TAC AAA AAA GGG CGG TTC AGC TTC AAT GTC AAA GGC GGG CGC    2205
 G   Y   K   K   G   R   F   S   F   N   V   K   G   G   R

TGC GAG GCG TGC CAT GGC GAT GGC ATC ATC AAA ATT GAG ATG CAC    2250
 C   E   A   C   H   G   D   G   I   I   K   I   E   M   H

TTT TTG CCG GAC GTG TAC GTC CCG TGC GAA GTG TGC CAC GGC AAA    2295
 F   L   P   D   V   Y   V   P   C   E   V   C   H   G   K

CGG TAC AAC CGC GAG ACG CTC GAG GTG ACG TAT AAA GGA AAA AAC    2340
 R   Y   N   R   E   T   L   E   V   T   Y   K   G   K   N

ATC GCC GAG GTG CTC GAC ATG ACG GTC GAA GAT GCG CTC GAC TTT    2385
 I   A   E   V   L   D   M   T   V   E   D   A   L   D   F

TTC GCC TCG ATC CCG AAA ATC AAA CGC AAG CTC GAG ACG CTC TAT    2430
 F   A   S   I   P   K   I   K   R   K   L   E   T   L   Y

GAC GTC GGG CTC GGT TAT ATG AAG CTC GGC CAG CCG GCG ACG ACG    2475
 D   V   G   L   G   Y   M   K   L   G   Q   P   A   T   T

CTC TCG GGC GGC GAG GCG CAG CGC GTC AAG CTC GCC GCT GAG CTT    2520
 L   S   G   G   E   A   Q   R   V   K   L   A   A   E   L

CAC CGC CGC TCC AAC GGC CGG ACG CTC TAC ATT TTG GAC GAG CCG    2565
 H   R   R   S   N   G   R   T   L   Y   I   L   D   E   P

ACG ACC GGG CTT CAT GTC GAT GAC ATC GCC CGG CTG CTT GAT GTG    2610
 T   T   G   L   H   V   D   D   I   A   R   L   L   D   V

CTC CAC CGG CTC GTC GAC AAC GGC GAT ACC GTG CTT GTC ATT GAA    2655
 L   H   R   L   V   D   N   G   D   T   V   L   V   I   E

CAT AAC TTG GAC GTC ATC AAA ACC GCG GAC TAT ATC ATT GAC TTA    2700
 H   N   L   D   V   I   K   T   A   D   Y   I   I   D   L

GGT CCG GAA GGC GGC GAC CGA GGC GGA CAA ATC GTC GCT GTC GGC    2745
 G   P   E   G   G   D   R   G   G   Q   I   V   A   V   G

ACG CCG GAA GAG GTG GCC GAG GTG GAG GAG TCG CAC ACC GGC CGC    2790
 T   P   E   E   V   A   E   V   E   E   S   H   T   G   R

TAC TTA AAC CCG ATT CTC GAG CGC GAC CGG GCG CGC ATG CAG GCG    2835
 Y   L   N   P   I   L   E   R   D   R   A   R   M   Q   A

CAA TAT GAA GCG GTG AAG GCG TAA                                2859
 Q   Y   E   A   V   K   A   *
```

Fig. 2

```
SEQ ID NO:3  gtggagggccgttttcaattagtggcgccatacgaaccgcaaggcgatcagccgcaggcg
SEQ ID NO:4  V  E  G  R  F  Q  L  V  A  P  Y  E  P  Q  G  D  Q  P  Q  A
             atcgccaagctcgttgacggcctgcgccgcggggtgaagcatcaaacgctgcttggggcg
             I  A  K  L  V  D  G  L  R  R  G  V  K  H  Q  T  L  L  G  A
             acggggacgggcaaaacgtttacgatctcgaacgtgatcgcccaagtcaacaaaccgacg
             T  G  T  G  K  T  F  T  I  S  N  V  I  A  Q  V  N  K  P  T
             cttgtcatcgcccacaacaaaacgctcgctggccaattgtacagcgagctgaaagagttt
             L  V  I  A  H  N  K  T  L  A  G  Q  L  Y  S  E  L  K  E  F
             ttcccgcacaacgccgtcgaatattttgtcagctattacgattactatcagccggaagcg
             F  P  H  N  A  V  E  Y  F  V  S  Y  Y  D  Y  Y  Q  P  E  A
             tatgtgccgcagacggatacgtacattgaaaaagacgcgaaaatcaacgatgaaatcgac
             Y  V  P  Q  T  D  T  Y  I  E  K  D  A  K  I  N  D  E  I  D
             aaattgcggcactcggcgacatcagccttgtttgagcgccgggacgtgattatcgttgcg
             K  L  R  H  S  A  T  S  A  L  F  E  R  R  D  V  I  I  V  A
             agcgtgtcgtgcatttacggtttagggtcgccggaagagtaccgcgaactggtcgtatcg
             S  V  S  C  I  Y  G  L  G  S  P  E  E  Y  R  E  L  V  V  S
             ctgcgcgttgggatggagatcgagcgcaacgcgttgcttcggcggcttgtcgacatccaa
             L  R  V  G  M  E  I  E  R  N  A  L  L  R  R  L  V  D  I  Q
             tacgaccgcaatgacatcgatttccgccgcggcacgttccgcgtccgcggcgatgttgtc
             Y  D  R  N  D  I  D  F  R  R  G  T  F  R  V  R  G  D  V  V
             gaaatttttccccgcgtcgcgcgatgaacattgcatccgcgtcgaattttcggcgatgaa
             E  I  F  P  A  S  R  D  E  H  C  I  R  V  E  F  F  G  D  E
             atcgagcgcatccgcgaggtggacgccttaaccggcgaggtgctcggcgagcgcgagcat
             I  E  R  I  R  E  V  D  A  L  T  G  E  V  L  G  E  R  E  H
             gtcgccatttttcccggcgtcgcacttcgtgacgcgcgaggagaaaatgcggctcgccatt
             V  A  I  F  P  A  S  H  F  V  T  R  E  E  K  M  R  L  A  I
             caaaacatcgaacaagagcttgaggagcggcttgccgaactgcgcgcgcaaggaaagctc
             Q  N  I  E  Q  E  L  E  E  R  L  A  E  L  R  A  Q  G  K  L
             ttagaggcgcagcggcttgagcagcggacgcgctatgaccttgaaatgatgcgcgagatg
             L  E  A  Q  R  L  E  Q  R  T  R  Y  D  L  E  M  M  R  E  M
             ggcttttgttccggcatcgaaaactactcgcgccatttggcgctgcggccgccaggctcg
             G  F  C  S  G  I  E  N  Y  S  R  H  L  A  L  R  P  P  G  S
             acgccgtatacattgcttgactattttccggacgattttttgatcatcgttgatgagtcg
             T  P  Y  T  L  L  D  Y  F  P  D  D  F  L  I  I  V  D  E  S
             cacgtcaccttgccgcagctgcgcggcatgtacaacggcgaccgggcgcgcaagcaagtg
             H  V  T  L  P  Q  L  R  G  M  Y  N  G  D  R  A  R  K  Q  V
             cttgtcgaccacggcttccgtctgccgtcggcgcttgacaaccggccgctcacgtttgaa
             L  V  D  H  G  F  R  L  P  S  A  L  D  N  R  P  L  T  F  E
             gagttcgagcaaaaaatcaatcaaattatttacgtctcagcgacgccggggccgtatgag
             E  F  E  Q  K  I  N  Q  I  I  Y  V  S  A  T  P  G  P  Y  E
             cttgaacacagcccgggcgttgtcgaacaaatcatccgcccgaccgggcttctcgaccca
             L  E  H  S  P  G  V  V  E  Q  I  I  R  P  T  G  L  L  D  P
             acgatcgacgtccgcccgacgaaagggcaaatcgacgatttgatcggcgaaattcgcgag
             T  I  D  V  R  P  T  K  G  Q  I  D  D  L  I  G  E  I  R  E
             cgcgtcgagcggaacgagcggacgttggtgacgacgctgacgaaaaagatggcggaagat
             R  V  E  R  N  E  R  T  L  V  T  T  L  T  K  K  M  A  E  D
             ttgaccgattatttgaaagaagcggggatcaaggtggcgtatttgcattcggaaattaag
             L  T  D  Y  L  K  E  A  G  I  K  V  A  Y  L  H  S  E  I  K
             acgctcgagcgcattgaaatcatccgcgatttgcggctcggcaaatacgatgtattggtc
             T  L  E  R  I  E  I  I  R  D  L  R  L  G  K  Y  D  V  L  V
             ggcatcaacttgcttcgcgaagggctcgacatcccagaagtgtcgcttgtcgccattttg
             G  I  N  L  L  R  E  G  L  D  I  P  E  V  S  L  V  A  I  L
             gacgccgacaaagaagggttttgcgctcggagcgctcgctcatccagacgatcggccgg
             D  A  D  K  E  G  F  L  R  S  E  R  S  L  I  Q  T  I  G  R
```

SEQ ID NO:3-4, continued

```
gcggcgcgcaacgcgaacggccatgtgatcatgtacgccgatacgatcacgaaatcgatg
 A  A  R  N  A  N  G  H  V  I  M  Y  A  D  T  I  T  K  S  M
gaaatcgccattcaagagacgaagcggcgccgcgcgattcaagaagagtacaaccgaaag
 E  I  A  I  Q  E  T  K  R  R  R  A  I  Q  E  E  Y  N  R  K
cacggcatcgtgccgcgcacggtgaaaaaggagattcgcgacgtcatccgcgcgacgtat
 H  G  I  V  P  R  T  V  K  K  E  I  R  D  V  I  R  A  T  Y
gcggcggaagagacggagatgtacgaggcaaagccggcggcagcgatgacgaaacaagag
 A  A  E  E  T  E  M  Y  E  A  K  P  A  A  A  M  T  K  Q  E
cgggaagagctgattcgaacgctcgaagcggaaatgaaagaggcggccaaagcgctcgac
 R  E  E  L  I  R  T  L  E  A  E  M  K  E  A  A  K  A  L  D
ttcgagcgggccgcccagctgcgcgatatcattttcgaattgaaagcggaagggtga
 F  E  R  A  A  Q  L  R  D  I  I  F  E  L  K  A  E  G  -
```

Fig. 3

```
SEQ ID NO:5  atgaacgagcggctgaaagaaaaaactggctgtgctgccggagcagccgggctgctatttg
SEQ ID NO:6  M  N  E  R  L  K  E  K  L  A  V  L  P  E  Q  P  G  C  Y  L
             atgaaagacaaacacggaacggtgatttatgtcggggaaggcgaagtcgctgaaagagcgc
             M  K  D  K  H  G  T  V  I  Y  V  G  K  A  K  S  L  K  E  R
             gtccgctcgtattttaccgggacgcatgacggcaagacgcagcggcttgttgaggagatc
             V  R  S  Y  F  T  G  T  H  D  G  K  T  Q  R  L  V  E  E  I
             gctgatttcgaatacatcgtcacctcgtcaaacgccgaggcgctcattttggagatgaat
             A  D  F  E  Y  I  V  T  S  S  N  A  E  A  L  I  L  E  M  N
             ttgatcaaaaagcatgatccgaaatacaacgtcatgctgaaagatgataaaagctacccg
             L  I  K  K  H  D  P  K  Y  N  V  M  L  K  D  D  K  S  Y  P
             tttattaaaatcaccgcagaaaagcatccgcgcctgcttatcacccgcaaagtgaaaaaa
             F  I  K  I  T  A  E  K  H  P  R  L  L  I  T  R  K  V  K  K
             gacggcggcaaatatttcggcccgtatccaaacgtgcaggcggcgaacgaaacgaaaaag
             D  G  G  K  Y  F  G  P  Y  P  N  V  Q  A  A  N  E  T  K  K
             ctgctcgaccgcttatatccgctccgcaaatgttcgacgctgccttcgcgcgcctgtttg
             L  L  D  R  L  Y  P  L  R  K  C  S  T  L  P  S  R  A  C  L
             tattaccatatgggccaatgcctcgcccgtgcgtccacccggtgtcggacgaacaaaat
             Y  Y  H  M  G  Q  C  L  A  P  C  V  H  P  V  S  D  E  Q  N
             aaggcgatggttgaacaaatcgtccgcttttttaaacggcgggtatgaagacgtgaagcgg
             K  A  M  V  E  Q  I  V  R  F  L  N  G  G  Y  E  D  V  K  R
             gagttggccgagaaaatgcacgaggcggcggaaacgctcgagtttgaacgggcgaaagaa
             E  L  A  E  K  M  H  E  A  A  E  T  L  E  F  E  R  A  K  E
             taccgcgatcaaatcgcggcgattgagatgacgatggaaaagcaaaaaatgatgctcaac
             Y  R  D  Q  I  A  A  I  E  M  T  M  E  K  Q  K  M  M  L  N
             gacttcatcgaccgcgatgtattcggctatgcgtacgacaaaggctggatgtgcgtgcaa
             D  F  I  D  R  D  V  F  G  Y  A  Y  D  K  G  W  M  C  V  Q
             gtgttttttccttcgccaagggaagctgattgagcgcgacgtgtcgatcttcccgctttac
             V  F  F  L  R  Q  G  K  L  I  E  R  D  V  S  I  F  P  L  Y
             caagacccggatgaggaaatgcttacgttttgggtcagttttatgcgaaagcgcatcat
             Q  D  P  D  E  E  M  L  T  F  L  G  Q  F  Y  A  K  A  H  H
             ttgaagccaaaagaagtcgttctcccgtccgacattgacggcgagctcgcccgcgaattg
             L  K  P  K  E  V  V  L  P  S  D  I  D  G  E  L  A  R  E  L
             ctcggcgttgccgtcgtccagccgaaaaaagggaagaaaaaagagcttgttgagctggcg
             L  G  V  A  V  V  Q  P  K  K  G  K  K  K  E  L  V  E  L  A
             agcaaaaacgcggccattgctctgaaagaaaaattttatttcatcgagcgggacgaagaa
             S  K  N  A  A  I  A  L  K  E  K  F  Y  F  I  E  R  D  E  E
             cggacgatcaaagcggtcgaacgtctcggagagcgtcttggcattccggcgccgcgccgc
             R  T  I  K  A  V  E  R  L  G  E  R  L  G  I  P  A  P  R  R
             atcgaggcgtttgacaactcgaacatttacggggccgatccggtctcggcgctcgtcgtt
             I  E  A  F  D  N  S  N  I  Y  G  A  D  P  V  S  A  L  V  V
             ttcctcgatggcaagccggcgaaaaaagaataccggaaatataaggtgaaaacggtcgcg
             F  L  D  G  K  P  A  K  K  E  Y  R  K  Y  K  V  K  T  V  A
             gggccgaacgattatgaaacgatgcgcgaagtcgtgcgccgccgctatacgcgcgtgttg
             G  P  N  D  Y  E  T  M  R  E  V  V  R  R  R  Y  T  R  V  L
             aaagaaggattgccgcttcccgatttgatcattatcgacggcggcaaaggccacttgtcg
             K  E  G  L  P  L  P  D  L  I  I  I  D  G  G  K  G  H  L  S
             gcggtgcgggatgtgctcgaaaacgaacttggactggatgtgccgctggctggattggcg
             A  V  R  D  V  L  E  N  E  L  G  L  D  V  P  L  A  G  L  A
             aaagacgaaaaacatcgcacatcagagcttttggccggcgacccgccggatgtcgtgccg
             K  D  E  K  H  R  T  S  E  L  L  A  G  D  P  P  D  V  V  P
             ctcgaccggcaaagccaagagttttatttattgcagcgcatccaggatgaagtgcatcgg
             L  D  R  Q  S  Q  E  F  Y  L  L  Q  R  I  Q  D  E  V  H  R
             tttgccgttatgtttcaccgaaagacgcggcagaaaacgatgttccattccgtgcttgat
             F  A  V  M  F  H  R  K  T  R  Q  K  T  M  F  H  S  V  L  D
```

SEQ ID NO:5&6, continued

```
gacatccccggcgtcggggaaaagcggaaaaaagcactcttgaattatttcggctctgtg
 D   I   P   G   V   G   E   K   R   K   K   A   L   L   N   Y   F   G   S   V
aaaaagatgaaagaggcgacggtggaagagttgcagcgggcgaacattccgcgagcggtg
 K   K   M   K   E   A   T   V   E   E   L   Q   R   A   N   I   P   R   A   V
gcggagaaaatctatgaaaaactgcatgaataa
 A   E   K   I   Y   E   K   L   H   E   -
```

Fig. 4

ATP-binding site 1:                          ATP-binding site 2:

Bsu GLSGSGKSSLAFDTI (SEQ ID NO:7)  Bsu GVSGSGKSTLVNEIL (SEQ ID NO:9)
    :::::::::::::::                       :::::::::::::::
Bca GLSGSGKSSLAFDTI                  Bca GVSGSGKSTLVNEVL (SEQ ID NO:10)
    :::::::::::::.                        :::::::::::.:.:
Eco GLSGSGKSSLAFDTL (SEQ ID NO:8)  Eco GCSGSGKSTLINDTL (SEQ ID NO:11)

Zinc-finger 1:

Bsu CPHCGFSIGELEPRLFSFNSPFGACPTC (SEQ ID NO:12)
    :: :::::::::::::::::::::::::
Bca CPYCGFSIGELEPRLFSFNSPFGACPDC (SEQ ID NO:13)
    :: ::::: ::::::::::: :::: ::
Eco CPICGYSMRELEPRLFSFNNPAGACPTC (SEQ ID NO:14)

Zinc-finger 2:

Bsu CEACRGDGIIKIEMHFLPDVYVPCEVC (SEQ ID NO:15)
    :::: ::::::::::::::::::::::
Bca CEACHGDGIIKIEMHFLPDVYVPCEVC (SEQ ID NO:16)
    :::: :::::::: ::::::::: :::
Eco CEACQGDGVIKVEMHFLPDIYVPCDQC (SEQ ID NO:17)

Fig. 9

Fluorescein-labeled 50mer duplex

```
            RsaI                                      HaeIII
5' - GACTACGTACTGTTACGGCTCCATCFCTACCGCAATCAGGCCAGATCTGC - 3'
3' - CTGATGCATGACAATGCCGAGGTAGCGATGGCGTTAGTCCGGTCTAGACG - 5'
``` where $F_{26}$ = internal fluorescein-label

M13mp19(+) strand

3' TTGCTCATCTAAATCAAACTGGTAATCTATGTAAA 5'

5'...TAGATTTAGTTFGACCATTAGATACA...3'

*Fig. 11*

| UvrA | – | + | – | + | + | + | + | + | + | + |
|---|---|---|---|---|---|---|---|---|---|---|
| UvrB | – | – | wt | Δβh | wt | Δβh | wt | Δβh | wt | Δβh |
| | 0 | 0 | 20 | 20 | 1 | 1 | 5 | 5 | 10 | 10 |

UvrA$_2$B-DNA
UvrA$_2$-DNA
UvrB-DNA →

Substrate DNA → lanes  1  2  3  4  5  6  7  8  9  10

| UvrA | – | + | + | + | + | + | + | + |
|---|---|---|---|---|---|---|---|---|
| UvrB | – | – | 50 | 100 | 200 | 50 | 100 | 200 |
| | | | | wt | | | Δβh | |

UvrA$_2$B-DNA
UvrA$_2$-DNA
UvrB-DNA →

Substrate DNA → lanes  1  2  3  4  5  6  7  8

# THERMOSTABLE UVRA AND UVRB POLYPEPTIDES AND METHODS OF USE

CONTINUING APPLICATION DATA

This application claims the benefit of U.S. Provisional Application Ser. No. 60/311,336, filed Aug. 10, 2001, which is incorporated by reference herein.

GOVERNMENT FUNDING

The present invention was made with government support under Grant No. NIH ES-61060 and ES-07955, awarded by the National Institutes of Health. The Government has certain rights in this invention.

BACKGROUND

DNA repair provides a major defense mechanism against DNA lesions and their potential consequences, including mutagenesis, carcinogenesis, or cell death. The nucleotide excision repair (NER) pathway is a general repair process that removes a remarkably diverse array of structurally unrelated lesions, ranging from UV-induced photoproducts, chemical adducts, abasic sites to certain types of cross-links (Van Houten, *Microbiol. Rev.* 54, 18–51 (1990)).

The mechanism of NER is best studied in the bacterium *Escherichia coli*. This pathway, consisting of five steps: damage recognition, incision, excision, DNA repair synthesis and ligation, is error-free and leads to restoration of the integrity of the genetic information. The NER in bacterial cells is initiated by a combined action of three proteins, a UvrA protein, a UvrB protein, and a UvrC protein, leading to recognition and incision of damaged DNA. The three proteins, which are also referred to as UvrABC endouclease, are typically not stable. For instance, *E. coli* UvrA protein has been shown to be heat labile, especially in dilute concentrations with a $t_{1/2}$ of less than five minutes at 37° C. (Zou et al., *J. Biol. Chem.* 273, 12887–12892 (1998)).

The UvrA protein, which has a moderate affinity for damaged DNA (Van Houten, *Microbiol. Rev.* 54, 18–51 (1990); Seeberg et al., *Proc. Natl. Acad. Sci. USA* 79, 988–992 (1982); Claassen et al., *J. Biol. Chem.* 266, 11388–11394 (1991)), associates with the UvrB protein to form a UvrA$_2$UvrB complex that tracks along DNA (Koo et al., *Proc. Natl. Acad. Sci. USA* 88, 1212–1216 (1991)) and delivers UvrB to the damaged site. UvrA, in an ATP-dependent reaction, dissociates from this complex at the damaged site and a very stable UvrB-DNA complex is formed (Orren et al., *Proc. Natl. Acad. Sci. USA* 86, 5237–5241 (1989); Orren et al., *J. Biol. Chem.* 265, 15796–15803 (1990)). This complex constitutes a high affinity binding site for the UvrC protein, which upon binding to a UvrB-DNA complex, triggers incision at the 4th to the 7th phosphodiester bonds 3' to the damaged site (Lin et al., *J. Biol. Chem.* 267, 17693–17700 (1992); Moolenaar et al., *J. Biol. Chem.* 270, 30508–30515 (1995)). Immediately after the 3' incision, 5' incision occurs at the 8th phosphate group 5' to the DNA lesion (Lin et al. *J. Biol. Chem.* 267, 17688–17692 (1992); Zou et al., *Biochemistry* 34, 13582–13593 (1995)). Prokaryotic NER leads to the excision of lesions as oligomers 12–15 nucleotides in length.

Within this reaction cascade the UvrB protein plays a central role since it interacts with all the components of excision repair, namely UvrA, UvrC, UvrD (helicase 11), DNA polymerase I and DNA (Sancar and Sancar (1988) *Annu. Rev. Biochem.*, 57, 29-67; Orren et al. (1992) *J. Biol. Chem.*, 267, 780–788). Sequence comparisons have identified six helicase motifs throughout the sequence of UvrB (Gorbalenya et al. (1989) *Nucleic Acids Res.*, 17, 4713–4730) indicating that UvrB is a member of the helicase II superfamily, like the helicases Rad3 and XPD involved in eukaryotic NER (Sung et al. (1987) *Proc. Natl. Acad. Sci. USA*, 84, 8951–8955; Sung et al. (1993) *Nature*, 365, 852–855). In complex with UvrA, UvrB has been shown to have helicase-like activity in a reaction requiring the hydrolysis of ATP (Oh and Grossman (1987) *Proc. Natl Acad. Sci. USA*, 84, 3638–3642; Oh and Grossman (1989) *J. Biol. Chem.*, 264, 1336–1343). In addition to its possible role of tracking along the DNA, UvrB alters the affinity of the UvrA$_2$B complex towards more bulky adducts compared with UvrA alone (Snowden and Van Houten (1991) *J. Mol. Biol.*, 220, 19–33; Visse et al. (1991) *J. Biol. Chem.*, 266, 7609–7617; Visse et al. (1994) *Biochemistry*, 33, 1804–1811). The UvrA dimer is sufficient in recognizing damaged DNA, but it is the UvrA$_2$B complex that binds to damaged sites with increased specificity and allows efficient DNA damage recognition in vivo. Furthermore, this damage processing, which involves bending and unwinding of the DNA (Lin et al. (1992) *J. Biol. Chem.*, 267, 17693–17700; Visse et al. (1994) *Biochemistry*, 33, 9881–9888; Zou and Van Houten (1999) *EMBO J.*, 18, 4889–4901), leads to a stable UvrB-DNA pre-incision complex serving as a scaffold for the binding of UvrC.

Genetic and biochemical data show the prokaryotic pattern of NER to be present in more than 30 different eubacterial species, including three thermophilic microorganisms, *Thermus thermophilus* (Yamamoto et al., *Gene* 171, 103–106 (1996)), *Aquifex aeolicus* (Deckert et al., *Nature* 392, 353–358 (1998)), and *Thermotoga maritima* (Nelson et al., *Nature* 399, 323–329 (1999)). Sequence analyses indicate a high level of amino acid sequence similarity between Uvr proteins from different, even phylogenetically very distant bacterial species. Furthermore, it has been shown that the UvrA and UvrB proteins from *E. coli*, a gram-negative bacterium, can be complemented both in vitro and in vivo with the UvrC protein from gram-positive bacterium, *Bacillus subtilis* (Lin et al., *J. Biol. Chem.* 265, 21337–21341 (1990)) indicating a significant evolutionary conservation of the NER system among Eubacteria. More recently, homologues of uvrA, uvrB, and uvrC genes have been found in the genome of *Methanococcus thermoautotrophicum* (Smith et al., *J. Bacteriol.* 179, 7135–7155 (1997)), a member of the third kingdom of organisms, Archaea. In contrast, the genome sequences of archaeal *Methanococcus janaschii* (Bult et al., *Science* 273, 1058–1073 (1996)) and *Archaeoglobus fulgidus* (Klenk et al., *Nature* 310, 364–370 (1997)) do not contain uvr gene homologues, suggesting the presence of a novel pattern of NER pathway at least in some archaeal species.

SUMMARY OF THE INVENTION

One in four people in the US will be diagnosed with cancer in their lifetime. It has been estimated that as much as 90% of all cancers are due to exposure to agents in the environment that directly or indirectly damages DNA. One of the most important problems in cancer biology is linking exposure of an individual to DNA damaging agents with mutations in critical genes (oncogenes) which lead to cancer. The ability to accurately and routinely measure DNA damage in people who may have been exposed to environmental pollutants would more readily allow analysis of the relationship between DNA damaging agents and mutations. Moreover, in the treatment of cancer, chemotherapeutic drugs are often used which cause DNA damage. Knowing the amount of damage produced in the tumor target versus collateral damage in surrounding normal tissue in patients undergoing chemotherapy would help in increasing the effectiveness of the drug treatment. While several biomarkers of exposure to DNA damaging agents have been developed, such as antibodies to specific DNA lesions, no rapid and easy approach is available to quantify DNA lesions.

The present invention represents a significant advance in the art of detecting damaged DNA. With the present invention, the coding regions of the UvrA and UvrB polypeptides of the thermophilic microbe Bacillus caldotenax have been cloned, sequenced, produced, and isolated. B. caldotenax is a thermophilic gram-positive eubacterium, with an optimal growth temperature about 65° C. Several thermostable proteins with optimal activity between 65° C. to 70° C., including Bca DNA polymerase have been cloned and characterized from this thermophilic microorganism. Unlike previously characterized UvrA and UvrB proteins, the proteins of the present invention advantagously are more stable at higher temperatures for longer periods of time.

The present invention provides polynucleotides wherein the complement of the polynucleotide hybridizes to SEQ ID NO:1 under standard hybridization conditions, and the polynucleotide encodes a polypeptide with ATPase activity. The ATPase activity of the polypeptide is increased by at least about 200% in the presence of a double stranded DNA polynucleotide compared to the ATPase activity of the polypeptide in the absence of the double stranded DNA polynucleotide. The polynucleotide may have the nucleotide sequence of SEQ ID NO:1.

The present invention further provides a polypeptide with an amino acid sequence having a structural similarity of at least about 65% with SEQ ID NO:2, with an ATPase activity that is increased by at least about 200% in the presence of a double stranded DNA polynucleotide when compared to the ATPase activity of the polypeptide in the absence of the double stranded DNA polynucleotide. Also included in the present invention are compositions including this polypeptide. The polypeptide may have the amino acid sequence of SEQ ID NO:2.

The present invention provides a polynucleotide wherein the complement of the polynucleotide hybridizes to SEQ ID NO:3 under standard hybridization conditions, the polynucleotide encoding a polypeptide that forms a complex at about 50° C. to about 80° C. with a UvrA polypeptide of SEQ ID NO:2 and a BPDE-DNA substrate. In other aspects of the present invention, the polynucleotide may encode a polypeptide with ATPase activity in the presence of a UvrA polypeptide having SEQ ID NO:2. This ATPase activity is present after preincubation of the isolated polypeptide at 50° C. to about 80° C. for about 10 minutes. The polynucleotide may have the sequence of SEQ ID NO:3.

The present invention also provides a composition of a first polypeptide having an amino acid sequence having a structural similarity of at least about 65% with SEQ ID NO:2, the first polypeptide forming a complex at about 50° C. to about 80° C. with a UvrB polypeptide having SEQ ID NO:4, and a BPDE-DNA substrate; and a second polypeptide having an amino acid sequence having a structural similarity of at least about 65% with SEQ ID NO:4, the second polypeptide forming a complex at about 50° C. to about 80° C. with a UvrA polypeptide having SEQ ID NO:2, and a BPDE-DNA substrate.

In another aspect, the present invention provides a polynucleotide having SEQ ID NO:5.

The present invention provides a kit for detecting DNA damage. The kit includes a first and a second component. One component is a first polypeptide having an amino acid sequence having a structural similarity of at least about 65% with SEQ ID NO:2, the first polypeptide forming a complex at about 50° C. to about 80° C. with a UvrB polypeptide having SEQ ID NO:4 and a BPDE-DNA substrate. The second component is second polypeptide having an amino acid sequence having a structural similarity of at least about 65% with SEQ ID NO:4, the second polypeptide forming a complex at about 50° C. to about 80° C. with a UvrA polypeptide having SEQ ID NO:2 and a BPDE-DNA substrate. Included are kits in which the first polypeptide may have an amino acid of SEQ ID NO:2 and kits in which the second polypeptide may have an amino acid sequence of SEQ ID NO:4. Also included are kits that may have an additional component of an antibody that binds to a polypeptide having the amino acid sequence SEQ ID NO:2 and kits that may have an additional component of an antibody that binds to a polypeptide having the amino acid sequence SEQ ID NO:4.

In another aspect, the present invention includes a method for detecting DNA damage. The method includes combining a first polypeptide, a second polypeptide and a double stranded DNA to form a mixture; incubating the mixture such that a complex forms of the first polypeptide, the second polypeptide, and the double stranded DNA and detecting the complex, where the presence of a complex indicates the presence of DNA damage. The first polypeptide is encoded by a polynucleotide, where the complement of the first polynucleotide hybridizes to SEQ ID NO:1 under standard hybridization conditions, and the first polypeptide forms a complex at about 50° C. to about 80° C., with a UvrB polypeptide having SEQ ID NO:4 and a BPDE-DNA substrate. The second polypeptide is encoded by a polynucleotide where the complement of the polynucleotide hybridizes to SEQ ID NO:3 under standard hybridization conditions, and where the second polypeptide forms a complex at about 50° C. to about 80° C. with a UvrA polypeptide having SEQ ID NO:2 and a BPDE-DNA substrate. In some aspects of the present invention are methods in which the complex may be detected by detecting the presence of the second polypeptide; this may include detecting the presence of the second polypeptide with an antibody that binds to the second polypeptide. Also included are methods where the first polypeptide may have an amino acid sequence including SEQ ID NO:2 and methods where the second polypeptide may have an amino acid sequence including SEQ ID NO:4. Also included are methods where the double stranded DNA may be from a subject, including subjects undergoing treatment for cancer or subjects that have been exposed to a genotoxin. The double stranded DNA may be obtained from the subject either before, during, or after treatment or exposure to the genotoxin. The treatment for cancer may include chemotherapy.

BRIEF DESCRIPTION OF THE FIGURES

FIG. 1. Nucleotide sequence encoding the B. caldotenax (Bca) UvrA protein (SEQ ID NO:1) and amino acid sequence of the B. caldotenax (Bca) UvrA protein (SEQ ID NO:2).

FIG. 2. Nucleotide sequence encoding the B. caldotenax (Bca) UvrB protein (SEQ ID NO:3) and amino acid sequence of the B. caldotenax (Bca) UvrB protein (SEQ ID NO:4).

FIG. 3. Nucleotide sequence encoding the B. caldotenax (Bca) UvrC protein (SEQ ID NO:5) and amino acid sequence of the B. caldotenax (Bca) UvrC protein (SEQ ID NO:6).

FIG. 4. Alignment of amino acid sequences of zinc finger DNA binding domains of *B. subtilis* (Bsu), *B. caldotenax* (Bca), and *E. coli* (Eco) UvrA protein. Identical amino acids are indicated by a double-dot, and similar amino acid residues (conserved substitutions) are indicated by a dot.

FIG. 5. Overproduction and purification of various Bca UvrA proteins. High range molecular weight markers (Bio-Rad) are indicated on the left.

FIG. 7. Binding of *B. caldotenax* UvrA protein to the BPDE-DNA substrate.

FIG. 9. An alignment of UvrB amino acid sequences from different species (from top to bottom: UvrB from *B. caldotenax* (SEQ ID NO:4), *Thermus thermophilus* (SEQ ID NO:18) and *E. coli*.(SEQ ID NO:19)). The alignment was generated with the programs ClustalW and ALSCRIPT (Barton (1993) Protein Eng. 6, 37–40; and Thompson et al. (1994) *Nucl. Acids Res.* 22,4673–4680).

FIG. 11. A schematic representation of the helicase substrate, HS IF-M13 mp19(+). The figure shows the complete nucleotide sequence of a fluorescein-containing 26-mer (bottom strand) (SEQ ID NO:43), HS1F, that has been annealed to singlestranded M13 mp19(+) DNA (top strand) (SEQ ID NO:42). The position of the fluorescein adduct in the bottom strand is designated as a bold F.

FIG. 12. Binding of Δβh UvrB to F26-50 dsDNA. UvrA (20 nM) was incubated with various amounts of wild-type or mutant (Δβh) UvrB as indicated at 55° C. for 20 minutes in the presence of 2 nM F26-50 duplex DNA with the modified strand 5' terminally labeled. The reaction mixtures were analyzed on 4% polyacrylamide native gels in the presence of ATP (1 mM) and MgC12 (10 mM).

DETAILED DESCRIPTION OF PREFERRED EMBODIMENTS OF THE INVENTION

Definitions

Figure 5A:
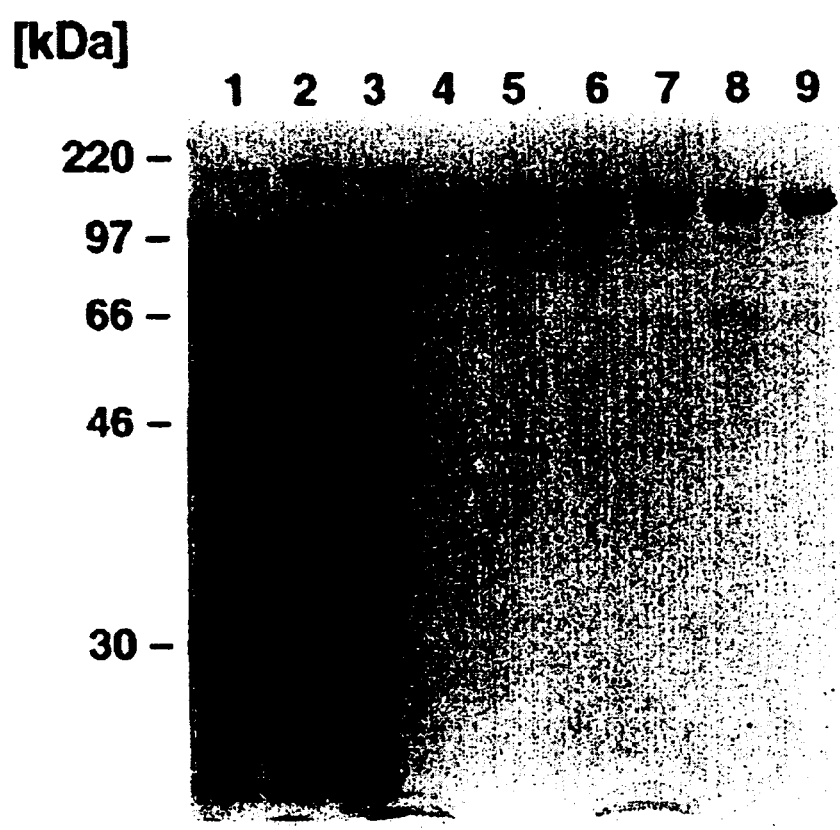
FIG. 5A represents overproduction and purification of Bca UvrA SD with removed internal Shine-Dalgarno site at position 564 (Bca UvrA$_{SD}$), expressed in *E coli* BL21(DE3) and induced with 1 mM IPTG at 30° C. for 3 hours (a large-scale purification from 9 liter-culture). Lane 1, 20 μl of non-induced cell extract; lane 2, 10 μl of induced cell extract; lane 3, 20 μl-aliquot of cell extract flow through the column; and lanes 4–9, 40 μl-aliquots of the first 6 fractions (~2-ml fractions) after elution from the chitin column, respectively.

As used herein, the term "isolated" means that a polynucleotide or polypeptide is either removed from its natural environment or synthetically derived, for instance by recombinant techniques, or chemically or enzymatically synthesized. An isolated polynucleotide denotes a polynucleotide that has been removed from its natural genetic milieu and is thus free of other extraneous or unwanted coding sequences, and is in a form suitable for use within genetically engineered protein production systems. Isolated polynucleotides of the present invention are free of other coding sequences with which they are ordinarily associated, but may include naturally occurring 5' and 3' untranslated regions such as promoters and terminators. Preferably, the polynucleotide or polypeptide is purified, i.e., essentially free from any other polynucleotides or polypeptides and associated cellular products or other impurities.

"Polynucleotide" and "nucleic acid sequences" are used interchangeably to refer to a linear polymeric form of nucleotides of any length, either ribonucleotides or deoxynucleotides, and includes both double- and single-stranded DNA and RNA. A polynucleotide can be linear or circular in topology. A polynucleotide can be obtained using any method, including, without limitations, common molecular cloning and chemical nucleic acid synthesis. A polynucleotide may include nucleotide sequences having different functions, including for instance coding sequences, and non-coding sequences.

As used herein "coding sequence," "coding region," and "open reading frame" are used interchangeably and refer to a polynucleotide that encodes a polypeptide, usually via mRNA, when placed under the control of appropriate regulatory sequences. The boundaries of the coding region are generally determined by a translation start codon at its 5' end and a translation stop codon at its 3'end.

A polynucleotide of the invention can be inserted in a vector. Construction of vectors containing a polynucleotide of the invention employs standard ligation techniques known in the art. See, for instance, Sambrook et al, *Molecular Cloning: A Laboratory Manual.*, Cold Spring Harbor Laboratory Press (1989). The term vector includes, but is not limited to, plasmid vectors, viral vectors, cosmid vectors, or artificial chromosome vectors. Typically, a vector is capable of replication in a bacterial host, for instance, *E. coli*.

Selection of a vector depends upon a variety of desired characteristics in the resulting construct, such as a selection marker, vector replication rate, and the like. A vector can provide for further cloning (amplification of the polynucleotide), e.g., a cloning vector, or for expression of the polypeptide encoded by the coding sequence, e.g., an expression vector. Suitable host cells for cloning or expressing the vectors herein are prokaryote or eukaryotic cells. Preferably the host cell secretes minimal amounts of proteolytic enzymes. Suitable prokaryotes include eubacteria, such as gram-negative or gram-positive organisms.

As used herein, an "expression vector" is a DNA molecule, linear or circular, that includes a segment encoding a polypeptide of interest operably linked to additional segments that provide for its transcription. Such additional segments may include promoter and terminator sequences, and optionally one or more origins of replication, one or more selectable markers, an enhancer, a polyadenylation signal, and the like. Expression vectors are generally derived from plasmid or viral DNA, or may contain elements of both.

By "host cell" is meant a cell that contains an expression vector and supports the replication or expression of the expression vector. Host cells may be prokaryotic cells such as E. coli, or eukaryotic cells such as yeast, insect, amphibian, or mammalian cells such as CHO, HeLa and the like, or plant cells.

Suitable plasmids for expression in E. coli, for example, include pUC(X), pKK223-3, pKK233-2, pTrc99A, and pET-(X) wherein (X) denotes a vector family in which numerous constructs are available. pUC(X) vectors can be obtained from Pharmacia Biotech (Piscataway, N.H.) or Sigma Chemical Co. (St. Louis, Mo.). pKK223-3, pKK233-2 and pTrc99A can be obtained from Pharmacia Biotech. pET-(X) vectors can be obtained from Promega (Madison, Wis.) Stratagene (La Jolla, Calif.) and Novagen (Madison, Wis.). To facilitate replication inside a host cell, the vector preferably includes an origin of replication (known as an "ori") or replicon. For example, ColE1 and PISA replicons are commonly used in plasmids that are to be propagated in E. coli.

An expression vector optionally includes regulatory sequences operably linked to the coding sequence. The invention is not limited by the use of any particular promoter, and a wide variety are known. Promoters act as regulatory signals that bind RNA polymerase in a cell to initiate transcription of a downstream (3' direction) coding sequence. The promoter used in the invention can be a constitutive or an inducible promoter. It can be, but need not be, heterologous with respect to the host cell. Preferred promoters for bacterial transformation include lac, lacUV5, tac, trc, T7, SP6 and ara.

An expression vector can optionally include a ribosome binding site (a Shine Dalgarno site for prokaryotic systems or a Kozak site for eukaryotic systems) and a start site (e.g., the codon ATG) to initiate translation of the transcribed message to produce the enzyme. It can also include a termination sequence to end translation. A termination sequence is typically a codon for which there exists no corresponding aminoacetyl-tRNA, thus ending polypeptide synthesis. The polynucleotide used to transform the host cell can optionally further include a transcription termination sequence. The rrnB terminators, which is a stretch of DNA that contains two terminators, T1 and T2, is an often used terminator that is incorporated into bacterial expression systems. Transcription termination sequences in vectors for eukaryotic cells typically include a polyadenylation signal 3' of the coding sequence.

The polynucleotide used to transform the host cell optionally includes one or more marker sequences, which typically encode a molecule that inactivates or otherwise detects or is detected by a compound in the growth medium. For example, the inclusion of a marker sequence can render the transformed cell resistant to an antibiotic, or it can confer compound-specific metabolism on the transformed cell. Examples of a marker sequence are sequences that confer resistance to kanamycin, ampicillin, chloramphenicol, tetracycline and neomycin.

"Complement" and "complementary" refer to the ability of two single stranded polynucleotides to base pair with each other, where an adenine on one polynucleotide will base pair to a thymine on a second polynucleotide and a cytosine on one polynucleotide will base pair to a guanine on a second polynucleotide. Two polynucleotides are complementary to each other when a nucleotide sequence in polynucleotide can base pair with a nucleotide sequence in a second polynucleotide. For instance, 5'-ATGC and 5'-GCAT are complementary. Typically two polynucleotides are complementary if they hybridize under the standard conditions referred to herein.

As used herein, "standard hybridization conditions" refer to hybridization conditions such as 6×SSC, 5× Denhardt, 0.5% sodium dodecyl sulfate (SDS), and 100 µg/ml fragmented and denatured salmon sperm DNA hybridized overnight at 65° C. and washed in 2×SSC, 0.1% SDS at least one time at room temperature for about 10 minutes followed by at least one wash at 65° C. for about 15 minutes followed by at least one wash in 0.2×SSC, 0.1% SDS at room temperature for at least 3–5 minutes. Typically, a 20×SSC stock solution contains about 3M sodium chloride and about 0.3M sodium citrate.

"Polypeptide" as used herein refers to a polymer of amino acids and does not refer to a specific length of a polymer of amino acids. Thus, for example, the terms peptide, oligopeptide, protein, and enzyme are included within the definition of polypeptide, whether naturally occurring or synthetically derived, for instance, by recombinant techniques or chemically or enzymatically synthesized. This term also includes post-expression modifications of the polypeptide, for example, glycosylations, acetylations, phosphorylations, and the like.

As used herein, a "biologically active" polypeptide is a polypeptide that can interact with another molecule, such as a polypeptide or a polynucleotide. The interaction can be, for instance, covalent or noncovalent binding interactions. Biological activity further includes incision and excision repair of a polynucleotide, and interactions of any type with other polypeptides that cause incision or excision repair of a polynucleotide. The biological activities of the polypeptides of the present invention are described herein.

As used herein, "structural similarity" refers to the identity between two polypeptides or two polynucleotides. For polypeptides, structural similarity is generally determined by aligning the residues of the two polypeptides (i.e., a candidate polypeptide and the polypeptide of SEQ ID NO:2, SEQ ID NO:4, or SEQ ID NO:6) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate polypeptide is the polypeptide being compared to the polypeptide of SEQ ID NO:2, SEQ ID NO:4, or SEQ ID NO:6. A candidate polypeptide can be isolated, for example, from an animal, preferably a microbe, or can be produced using recombinant techniques, or chemically or enzymatically synthesized. Preferably, polypeptides are compared using the Blastp program of the BLAST 2 search algorithm, as described by Tatiana, et al. (*FEMS Microbiol Lett,* 174, 247–250 (1999)), and available on the world wide web at ncbi.nlm.nih.gov/gorf/bl2.html. Preferably, the default values for all BLAST 2 search parameters are used, including matrix=BLOSUM62; open gap penalty=11, extension gap penalty=1, gap x_dropoff=50, expect=10, wordsize=3, and filter on. In the comparison of two amino acid sequences using the BLAST search algorithm, structural similarity is referred to as "identities." In some aspects of the present invention, polypeptides of the present invention include an amino acid sequence having a structural similarity with SEQ ID NO:2, SEQ ID NO:4, or SEQ ID NO:6 of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

For polynucleotides, structural similarity is generally determined by aligning the residues of the two polynucleotides (i.e., the nucleotide sequence of the candidate coding region and the nucleotide sequence of the coding region of SEQ ID NO:1, SEQ ID NO:3, or SEQ ID NO:5) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate coding region is the coding region being compared to a coding region present in SEQ ID NO:1, SEQ ID NO:3, or SEQ ID NO:5. Preferably, two polynucleotide sequences are compared using the Blastn program of the BLAST 2 search algorithm, as described by Tatiana, et al. (*FEMS Microbiol Lett,* 174, 247–250 (1999)), and available on the world wide web at ncbi.nlm.nih.gov/gorf/bl2.html. Preferably, the default values for all BLAST 2 search parameters are used, including reward for match=1, penalty for mismatch=−2, open gap penalty=5, extension gap penalty=2, gap x_dropoff=50, expect=10, wordsize=11, and filter on. In the comparison of two nucleotide sequences using the BLAST search algorithm, structural similarity is referred to as "identities." In some aspects of the present invention, the polynucleotides of the present invention include nucleotide sequences having a structural similarity with SEQ ID NO:1, SEQ ID NO:3, or SEQ ID NO:5 of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As used herein, "thermophilic microbe" refers to a microbe that typically grows at a temperature of at least about 50° C. An example of a thermophilic microbe is *Bacillus caldotenax*.

An "active analog" or "active fragment" of a polypeptide of the invention is a polypeptide having biological activity. An active analog of the invention includes a polypeptide having one or more amino acid substitutions that do not eliminate biological activity. Substitutes for an amino acid in the polypeptides of the invention may be selected from other members of the class to which the amino acid belongs. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$.

Analogs, as used herein, also include modifications. Modifications include a polypeptide that is chemically and enzymatically derivatized at one or more constituent amino acid, including side chain modifications, backbone modifications, and N- and C-terminal modifications including acetylation, hydroxylation, methylation, amidation, and the attachment of carbohydrate or lipid moieties, cofactors, and the like. Modified polypeptides of the invention will retain the biological activity of the unmodified polypeptide.

As used herein, fragments of a polypeptide of the invention include a portion of the polypeptide containing deletions or additions of one or more contiguous or noncontiguous amino acids such that the resulting polypeptide still retains the biological activity of the full length polypeptide.

"ATPase activity" as used herein refers to the hydrolysis of ATP to ADP.

As used herein, "DNA damage" and "damaged polynucleotide" refers to an altered polynucleotide. Alterations include, for example, UV-induced photoproducts, cross-links, alkylation products, deamination products, depurination and depyrimidination, phosphodiester bond cleavage, and other damaged nucleotides. Alterations also include, but are not limited to, UV dimers (e.g., cyclobutane pyrimidine dimers and 6,4-photoproducts), polycyclic aromatic hydrocarbon adducts (e.g., benzo(a)pyrene and dimethylbenzanthracene), cis-platinum adducts, aflatoxin adducts, psoralen adducts, anthramycin adducts, mitomycin C adducts, a-acetoxy-2-aminofluorene adducts, and N-hydroxy-2-aminofluorene adducts.

Other alterations include changes in the covalent or the noncovalent bonds in the polynucleotide sequence. Illustrative of a covalent interaction between a polynucleotide and another molecule are changes to a nucleotide base (e.g., formation of thumine glycol) and covalent cross-links between double-stranded DNA sequences which are introduced by ultraviolet radiation or by cis-platinum. Yet another example of a covalent interaction between a polynucleotide and another molecule includes covalent binding of two polynucleotide sequences to psoralen following ultraviolet irradiation. Non-covalent interactions between a polynucleotide and another molecule include non-covalent interactions of a polynucleotide sequence with a molecule other than a polynucleotide sequence and other than a polypeptide sequence. Non-covalent interactions between a polynucleotide sequence with a molecule other than a polynucleotide sequence and other than a polypeptide sequence are illustrated by non-covalent intercalation of ethidium bromide or of psoralen between the two strands of a double-stranded DNA sequence.

As used herein, "incised polynucleotide," "incision," and "incision activity" refer to cleavage of a phosphodiester bond between two bases in a damaged polynucleotide. The phosphodiester bond can be located 3' (i.e., downstream) of the alteration in the polypeptide, or 5' (i.e., upstream) of the alteration in the polypeptide.

As used herein, the term "complex" describes the molecular entity formed by the noncovalent interaction of a polypeptide or polypeptides with double stranded DNA. Such noncovalent interactions include, but are not limited to, hydrogen bonding, salt bridging, Van der Waals interactions, and combinations thereof.

As used herein, the term "thermostabile" indicates that a polypeptide remains biologically active at an elevated temperature higher than about 37° C. for a time period of about 5 minutes to about 60 minutes, including about 10 minutes to about 30 minutes, and including about 15 minutes to about 20 minutes. This includes, but is not limited to, temperatures of about 50° C. to about 80° C., about 55° C. to about 65° C., about 55° C., and about 65° C.

The term "mismatch" refers to a non-covalent interaction between two nucleic acids, each nucleic acid residing on a different single-stranded polynucleotide, which does not follow the base-pairing rules. For example, for the partially complementary sequences 5'-AGT-3' and 5'-AAT-3', a G-A mismatch is present.

As used herein, a "biological sample" refers to a sample of tissue or fluid isolated from a subject, including but not limited to, for example, blood, plasma, serum, lymph tissue and lymph fluid, cerebrospinal fluid, bone marrow, brain tissue, samples of the skin, organs, biopsies and also samples of in vitro cell culture constituents including but not limited to conditioned media resulting from the growth of cells and tissues in culture medium, and cell components, or combinations thereof. A biological sample suspected of containing a polynucleotide of interest may include a (prokaryotic or eukaryotic), a cell, a tissue or organ extract, body fluid, chromosomes or extrachromosomal elements isolated from a cell, genomic DNA, RNA, cDNA and the like.

A "subject" is an organism, including, for example, a microbe, a plant, or an animal. An animal may include, for example, a rat, mouse, or human. Subject also includes model organisms, including animal models, used to study the effects of a genotoxin on polynucletides.

"Treatment for cancer" as used herein includes therapies to decrease morbidity and mortality in a patient having cancer. Therapies include, for instance, chemotherapy and radiotherapy.

As used herein, "genotoxin" or a "genotoxic agent" refer to any agent that directly or indirectly damages DNA. This includes compounds that arise in the cell naturally, or are directly derived from the environment, or indirectly from exposure to a agent in the environment, such as organic or inorganic compounds and ionizing radiation. A genotoxin may also be called a mutagen or an environmental pollutant.

Unless otherwise specified, "a," "an," "the," and "at least one" are used interchangeably and mean one or more than one.

UvrA Polynucleotides:

The present invention provides isolated polynucleotides encoding thermostable UvrA polypeptides. As used herein a UvrA polypeptide refers to a polypeptide having one or more of the biological activities which are described herein. Such isolated polynucleotides may be isolated from a thermophilic organism, for example, from *Bacillus caldotenax*. Examples of the present invention include an isolated polynucleotide having the nucleotide sequence of SEQ ID NO:1, and the complement thereof. Also included in the present invention are polynucleotides hybridizing to SEQ ID NO:1 under standard hybridization conditions, and complements thereof, that encode a polypeptide that exhibits one or more of the biological activities of a UvrA polypeptide having the amino acid sequence of SEQ ID NO:2. Also included in the present invention are polynucleotides having a structural similarity of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98% or at least about 99% with the nucleotide sequence of SEQ ID NO:1, where the polynucleotide encodes a polypeptide that exhibits one or more of the biological activities of a UvrA polypeptide having the amino acid sequence of SEQ ID NO:2.

The biological activities a UvrA polypeptide, and the assays for measuring these biological activities, are described in more detail herein. Briefly, the biological activities of a UvrA polypeptide having the amino acid sequence of SEQ ID NO:2 include, but are not limited to: 1) forming a complex with a BPDE-DNA substrate; 2) exhibiting a thermostabile ATPase activity; 3) exhibiting an ATPase activity that is increased in the presence of a double stranded DNA polynucleotide compared to its ATPase activity in the absence of double stranded DNA polynculeotide; and 4) forming a complex that includes the UvrA polypeptide, a UvrB polypeptide having the amino acid sequence of SEQ ID NO:4 and a BPDE-DNA substrate.

As used herein, "BPDE-DNA substrate," refers to a 50 basepair double stranded DNA duplex, 5'GACTACGTACT-GTTACGGCTCCATCGCTACC GCAATCAGGCCA-GATCTGC3' (SEQ ID NO:44), containing a center located, site-specific cis(+)- or trans(+)-BPDE-$N^2$-quanine adduct. BPDE is benzo[a]pyrene diol epoxide, 7,8-dihydroxy-9,10-epoxy-7,8,9, 10-tetrahydrobenzo[a]pyrene. The BPDE-DNA substrate serves as standardized damaged, double stranded DNA template that is effectively recognized and incised by the UvrA, UvrB, and UvrC polypeptides of the NER repair system. A BPDE-DNA substrate may be produced as described by Zou et al., (1995) *Biochemistry* 34, 13582–13593 and may be 3'- or 5'-[$^{32}$P] labeled. Many other well defined damaged DNA templates may be used in assaying for recognition and incision by the UvrABC nuclease. Such defined templates may be a double stranded polynucleotide of about 50 to about 150 basepairs in length, have a defined nucleotide sequence and contain a defined lesion in a defined position. For example, a fluorescein-containing 50 basepair double stranded DNA substrate, containing a single internal fluorescein adduct ($F_{26}$-50 ds DNA), as prepared as described in Skorvaga et al., ((2002) *J. Biol. Chem.* 277, 1553–1559), may be used in the place of a BPDE-DNA substrate. See, for example, FIG. 10. Additional defined DNA templates are known to those of skill in the art. See, for example, Zou et al., (1997) *J. Biol. Chem.* 272, 4820–4827. Effective recognition by the UvrA and UvrB polypeptides of the NER system is not, however, limited to such defined damaged DNA substrates. The NER system has a broad substrate specificity range, recognizing and processing a large variety of DNA lesions having modifications of different sizes and with different chemical properties (See Theis et al. (2000) *Mutation Research* 460, 277–300; Van Houten, (1990) *Microbiol. Rev.* 54:18–51; and Van Houten and Snowden, (1993) *BioEssays* 15:51–59).

Also included in the present invention are polynucleotide fragments. A polynucleotide fragment is a portion of an isolated polynucleotide as described herein. Such a portion may be several hundred nucleotides in length, for example about 100, about 200, about 300, about 400, about 500, about 600, about 700, about 800, about 900 or about 1000 nucleotides in length. Such a portion may be about 10 nucleotides to about 100 nucleotides in length, including but not limited to, about 14 to about 40 nucleotides in length.

UvrA Polypeptides:

The present invention is also directed to isolated thermostable UvrA polypeptides, active analogs, active fragments thereof, and compositions including such polypeptides. Such isolated polypeptides may be isolated from a thermophilic organism, for example, from *Bacillus caldotenax*. One example of such a polypeptide is the isolated UvrA polypeptide having the amino acid sequence of SEQ ID NO:2. The present invention includes isolated UvrA polypeptides that have an amino acid sequence with a structural similarity of at least about 65% with the amino acid sequence of SEQ ID NO:2 and maintain one or more of the biological activities of a UvrA polypeptide having the amino acid sequence of SEQ ID NO:2. The present invention also includes isolated UvrA polypeptides with at least about 70%, at least about 75%, at least about 80%, at least about 85%, at least about 90%, at least about 95%, at least about 96%, at least about 97%, at least about 98%, or at least about 99% structural similarity with the amino acid sequence of SEQ ID NO:2 that maintain one or more of the biological activities of a UvrA polypeptide having the amino acid sequence of SEQ ID NO:2. Also included in the isolated UvrA polypeptides of the present invention are polypeptides encoded by a polynucleotide sequence that hybridizes under standard hybridization conditions to a nucleotide sequence of SEQ ID NO:1, the UvrA polypeptide maintaining one or more of the biological activities of a UvrA polypeptide having the amino acid sequence of SEQ ID NO:2.

The biological activities of a UvrA polypeptide having the amino acid sequence of SEQ ID NO:2 have been previously described, above. Such polypeptides may exhibit at least about 10%, including at least about 20%, at least about 30%, at least about 40%, at least about 50%, at least about 60%, at least about 70%, at least about 80%, at least about 90%, at least about 100%, at least about 120%, at least about 150%, at least about 200%, at least about 400%, at least about 500%, at least about 1000%, at least about 2000% or even more, of any one or more biological activities of a UvrA polypeptide having the amino acid of SEQ ID NO:2. These biological activities may be assayed for by methods that include, but are not limited to the following assays.

DNA Binding Assay

The formation of a complex of a BPDE-DNA substrate and a UvrA polypeptide may be assayed quantitatively by gel mobility shift. Typically, a labeled defined DNA substrate, such as a 3'- or 5'-[$^{32}$P] labeled BPDE-DNA substrate may be incubated with a UvrA polypeptide. Typically, about 1 to about 5 nM, preferably about 2 nM, of the DNA substrate is incubated with about 5 nM to about 300 nM, more preferably about 10 nM to about 100 nM, most preferably about 20 nM to about 50 nM of a UvrA polypeptide in about 20 ul of a UvrABC binding buffer in the presence or absence of about 1 mM ATP. The UvrABC buffer is about 25–100 mM Tris-HCl, more preferably about 50 mM Tris-HCl, about pH 7–10, more preferably about pH 7.5, about 25–500 mM KCl, more preferably about 50 mM KCl, about 10 mM MgCl$_2$, about 5 mM dithiothreitol. The incubation may take place at a temperature ranging from about 37° C. to about 95° C., more preferably from about 50° C. to about 85° C., even more preferably at about 55° C. or at about 65° C., for a time period of about 5 to about 30 minutes, preferably about 10 minutes to about 20 minutes, more preferably about 15 minutes. After incubation, glycerol at about 80% (v/v) is added to the reaction mixture and the reaction mixture is loaded onto a 4%, native polyacrylamide gel (acryl:bis at 80:1). The gel and TBE running buffer (89 mM Tris, 89 mM boric acid, 2 mM EDTA) typically contains about 1 mM ATP and about 10 mM MgCl$_2$. The reaction mixture can be electrophoresed for 2.5–3.0 hours at a constant voltage (for instance, about 100 V) at room temperature. The gel can be dried and autoradiographed using KODAK XAR5 X-ray film exposed to the gel overnight in the presence of intensifying screens at −80° C. Alternatively, if a fluorescein labeled DNA substrate has been used, the gel can be dried and exposed against a Storage Phosphor Screen (Molecular Dynamics, Amersham Biosciences, Sunnyvale, Calif.) overnight at room temperature. Quantification of DNA binding products is by well known procedures, for example with a PhosphorImager 425 (Molecular Dynamics)

The DNA binding assay, as described above, may also be used to assay for the formation of a complex of a UvrA polypeptide, a UvrB polypeptide and a BPDE-DNA substrate. Typically, when such a complex is being assayed, about about 5 nM to about 300 nM, more preferably about 10 nM to about 100 nM, most preferably about 20 to about 50 nM of a UvrB polypeptide is also added to the binding buffer. UvrB polypeptides are as decribed herein. Preferably, when the activity of a UvrA polypeptide is being assayed, the UvrB polypeptide has the amino acid sequence of SEQ ID NO:4.

Alternatively, after the gel mobility shift assay described above, the complex formed by the Uvr polypeptides interacting with a DNA substrate may be quantified by Western blotting analysis. Western blotting procedures are well described in the literature. Briefly, the gel is blotted to a nitrocellulose immobilization membrane (Schleicher & Schuell) using a Hoefer electrotransfer unit and manufacturer's instructions. The membrane is then treated with a UvrA- or UvrB-specific Antibody.

Assays for ATPase Activity

ATPase activities of a UvrA polypeptide may be measured using methods for determining the conversion of ATP to ADP. For example, ATPase activities may be measured using a coupled assay in which the hydrolysis of ATP to ADP is linked to the oxidation of NADH. For such an assay, the standard ATPase assay mixture may consist of about 25–500 mM Tris-Cl, more preferably about 50 mM Tris-Cl, about pH 7–10, more preferably about pH 7.5, about 100–500 mM KCl, more preferably about 100 mM KCl, about 10 mM MgSO$_4$, about 1 mM DTT, about 10% glycerol, about 2 mM phosphoenol pyruvate, about 0.15 mM NADH, pyruvate kinase (about 20 units/ml), lactate dehydrogenase (about 20 units/ml) and about 0.01 μM to about 1.0 μM, more preferably about 0.1 μM UvrA polypeptide. Assay mixtures, about 0.5 ml, are allowed to equilibrate to 37° C. and reactions are initiated by the addition of ATP (about 1 mM). The rate of ATP hydrolysis is calculated from the slope of the linear decrease in absorbance at 340 nm.

To determine the thermostability of ATPase activity, a 50 μl mixture containing 25–500 mM Tris-Ci, more preferably about 50 mM Tris-Cl, about pH 7–10, more preferably about pH 7.5, about 100–500 mM KCl, more preferably about 100 mM KCl, about 10% glycerol and about 1 μM of a UvrA polypeptide is preincubated at a temperature of about 37° C. to about 90° C., more preferably from about 50° C. to about 85° C., most preferably at about 55° C. or at about 65° C., for a time period of about 5 to about 30 minutes, preferably about 10 to about 20 minutes, more preferably about 15 minutes. Following heat treatment, the entire 50 μL mixture is added to a 450 μL standard ATPase assay mixture and the ATPase activity is measured as described above.

To determine the effect of double stranded DNA on the ATPase activities of a UvrA polypeptide, ATPase assays can be carried out under standard conditions as described above, however, a double stranded DNA, such as a plasmid, for instance a pGL-2 plasmid, is added in one μl-aliquots to the assay mixture and allowed to incubate in the presence of a UvrA polypeptide for about 5 minutes prior to the addition ATP. The concentrations of plasmid DNA can range from about 0.1 nM to about 20 nM, including from about 0.25 nM to about 10 nM, and including from about 1.0 nM to about 5.0 nM. ATPase activity may be increased at least about 200%, more preferably at least about 400%, and most preferably at least about 2000%.

Also included in the present invention are polypeptide fragments. A polypeptide fragment is a shortened portion of an isolated polypeptide as described herein. Such a portion may be about 75 amino acids or more in length, for example, of about 75, about 100, about 125, about 150, about 200, about 225, about 250, about 275, about 300, about 325, about 350 or more amino acids in length. Such a portion may be about 25 to about 75 amino acids in length, for example, about 25, about 30, about 35, about 40, about 45, about 50, about 55, about 60, about 65, about 70 or about 75 amino acids in length. Such a portion may be about 6 to about 25 amino acids in length, for example, about 6, 7, 8, 9, 10, 11, 12, 13, 14, 15, 16, 17, 18, 19, 20, 21, 22, 23 or 24 or amino acids in length.

UvrB Polynucleotides:

The present invention provides isolated polynucleotides encoding thermostable UvrB polypeptides. As used herein a UvrB polypeptide refers to a polypeptide having one or more of the biological activities which are described herein. Such isolated polynucleotides may be isolated from a thermophilic organism, for example, from *Bacillus caldotenax*. Examples of the present invention include an isolated polynucleotide having the nucleotide sequence of SEQ ID NO:3, and the complement thereof. Also included in the present invention are polynucleotides hybridizing to SEQ ID NO:3 under standard hybridization conditions, and complements thereof, that encode a polypeptide that exhibits one or more of the biological activities of a UvrB polypeptide having the amino acid sequence of SEQ ID NO:4. Also included in the present invention are polynucleotides having a structural similarity of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% with the nucleotide sequence of SEQ ID NO:3, where the polynucleotide encodes a polypeptide that exhibits one or more of the biological activities of a UvrB polypeptide having the amino acid sequence of SEQ ID NO:4.

The biological activities a UvrB polypeptide, and the assays for measuring these biological activities, are described in more detail herein. Briefly, the biological activities of a UvrB polypeptide having the amino acid sequence of SEQ ID NO:4 include, but are not limited to: 1) exhibiting a thermostabile ATPase activity in the presence of an UvrA polypeptide having the amino acid sequence of SEQ ID NO:2; and 2) forming a complex that includes the UvrB polypeptide, a UvrA polypeptide having the amino acid sequence of SEQ ID NO:2 and a BPDE-DNA substrate.

Also included in the present invention are polynucleotide fragments. A polynucleotide fragment is a portion of an isolated polynucleotide as described herein. Such a portion may be several hundred nucleotides in length, for example at least about 100, at least about 200, at least about 300, at least about 400, at least about 500, at least about 600, at least about 700, at least about 800, at least about 900, or at least about 1000 nucleotides in length. Such a portion may be about at least about 10 nucleotides to at least about 100 nucleotides in length, including but not limited to, at least about 14 to at least about 40 nucleotides in length.

UvrB Polypeptides:

The present invention is also directed to isolated thermostabile UvrB polypeptides, active analogs and active fragments thereof. The present invention also includes compositions including such polypeptides, and optionally including UvrA polypeptides. Such isolated polypeptides may be isolated from a thermophilic organism, for example, from *Bacillus caldotenax*. One example of such a polypeptide is the isolated UvrB polypeptide having the amino acid sequence of SEQ ID NO:4. The present invention includes isolated UvrB polypeptides that have an amino acid sequence with a structural similarity of at least about 65% with the amino acid sequence of SEQ ID NO:4 and maintain one or more of the biological activities of a UvrB polypeptide having the amino acid sequence of SEQ ID NO:4. The present invention also includes isolated UvrB polypeptides with at least about 70%, at least about 75%, at least about 80%, at least about 85%, at least about 90%, at least about 95%, at least about 96%, at least about 97%, at least about 98%, or at least about 99% structural similarity with the amino acid sequence of SEQ ID NO:4 that maintain one or more of the biological activities of a UvrB polypeptide having the amino acid sequence of SEQ ID NO:4. Also included in the isolated UvrB polypeptides of the present invention are polypeptides encoded by a polynucleotide sequence that hybridizes under standard hybridization conditions to a nucleotide sequence of SEQ ID NO:3, the UvrB polypeptide maintaining one or more of the biological activities of a UvrB polypeptide having the amino acid sequence of SEQ ID NO:4.

The biological activities of a UvrB polypeptide having the amino acid sequence of SEQ ID NO:4 have been described herein. The isolated polypeptides of the present invention may maintain one or more of the biological activities of a UvrB polypeptide having the amino acid sequence of SEQ ID NO:4. Such polypeptides exhibit at least about 10%, including at least about 20%, at least about 30%, at least about 40%, at least about 50%, at least about 60%, at least about 70%, at least about 80%, at least about 90%, at least about 100%, at least about 120%, at least about 150%, at least about 200%, at least about 400%, at least about 500%, at least about 1000%, at least about 2000% or even more, of any one or more of the biological activities of a UvrB polypeptide having the amino acid of SEQ ID NO:4.

These biological activities may be assayed for by methods that include, but are not limited to the following assays.

The formation of a complex of a UvrA polypeptide, UvrB polypeptide, and a BPDE-DNA substrate may be assayed quantitatively by a DNA Binding Assay, as previously described herein.

The ATPase activity of a UvrB polypeptide may be measured using methods for determining the conversion of ATP to ADP, including a coupled enzyme assay system consisting of pyruvate kinase and lactate dehydrogenase to link the hydrolysis of ATP to the oxidation of NADH. For such an assay, the standard ATPase assay mixture may consist of about 25–500 mM Tris-Cl, more preferably about 50 mM Tris-Cl, about pH 7–10, more preferably about pH 7.5, about 50 mM NaCl, about 4 mM $MgCl_2$, about 1 mM dithiothreitol, about 20 units/ml lactate dehydrogenase, about 20 units/ml pyruvate kinase, about 2 mM phosphoenol pyruvate, about 0.15 mM NADH, a UvrA polypeptide and a UvrB polypeptide in the presence or absence of about 50 ng of UV-irradiated DNA substrate. A UV-irradiated DNA substrate may be prepared by exposure of a plasmid, for instance, pUC 18, to 200 J/m2. Each of the UvrA polypeptide and the UvrB polypeptide are present in the assay mixture in an amount of about 100 nM to about 500 nM, more preferably about 200 nM. Prior to addition to the assay mixture, UvrA polypeptides and UvrB polypeptides may be preincubated at a temperature of about 37° C. to about 90°

C., more preferably from about 50° C. to about 85° C., most preferably at about 55° C. or at about 65° C., for a time period of about 5 to about 60 minutes, preferably about 10 to about 30 minutes, most preferably about 15 to about 20 minutes. Assay mixtures, about 0.5 ml, are allowed to equilibrate to 37° C. and reactions are initiated by the addition of ATP (about 0.5 mM to about 2.0 mM, more preferably about 1 mM). The rate of ATP hydrolysis is calculated from the slope of the linear decrease in absorbance at 340 nm.

Also included in the present invention are polypeptide fragments. A polypeptide fragment is a shortened portion of an isolated polypeptide as described herein. Such a portion may be for example, of about 100, about 125, about 150, about 200, about 225, about 250, about 275, about 300, about 325, about 350 or more amino acids in length. Such a portion may be about 25 to about 75 amino acids in length, for example, about 25, about 30, about 35, about 40, about 45, about 50, about 55, about 60, about 65, about 70 or about 75. Such a portion may be about 6 to about 25 amino acids in length, for example, 6, 7, 8, 9, 10, 11, 12, 13, 14, 15, 16, 17, 18, 19, 20, 21, 22, 23 or 24 or amino acids in length.

Antibodies:

Also included in the present invention are antibodies or other agents that specifically bind to the isolated polypeptides of the invention. As used herein, the term "antibodies" includes polyclonal antibodies, affinity-purified polyclonal antibodies, monoclonal antibodies, and antigen-binding fragments thereof, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. The term "polyclonal antibody" refers to an antibody produced from more than a single clone of plasma cells; in contrast "monoclonal antibody" refers to an antibody produced from a single clone of plasma cells. Polyclonal antibodies may be obtained by immunizing a variety of warm-blooded animals such as horses, cows, goats, sheep, dogs, chickens, rabbits, mice, hamsters, guinea pigs and rats as well as transgenic animals such as transgenic sheep, cows, goats or pigs, a pig or horse, with an immunogen. The resulting antibodies may be isolated from other proteins by using an affinity column having an Fc binding moiety, such as protein A, or the like. Monoclonal antibodies can be obtained by various techniques familiar to those skilled in the art. Briefly, spleen cells from an animal immunized with a desired antigen are immortalized, commonly by fusion with a myeloma cell [see, Kohler and Milstein (1976) *Eur. J. Immunol.* 6, 511–519; J. Goding (1986) In "Monoclonal Antibodies: Principles and Practice," Academic Press, pp 59–103]. Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and the yield of the monoclonal antibodies produced by such cells may be enhanced by various techniques, including injection into the peritoneal cavity of a vertebrate host.

The isolated polypeptides of the present invention, or fragments thereof, serve as an antigen to immunize an animal to elicit an immune response. Immunization with antigen may be accomplished in the presence or absence of an adjuvant, e.g., Freund's adjuvant. Booster immunizations may be given at intervals, e.g., 2–8 weeks. Both polyclonal and monoclonal antibodies may be labeled with detectable label using methods known in the art. For example, fluorescent labels or peroxidase may be used as detectable labels. Various techniques useful in these arts are discussed, for example, in Harlow and Lane, (1988) "Antibodies: A Laboratory Manual," Cold Spring Harbor, N.Y.

The phrase "specifically binds" or "specifically immunoreactive with," when referring to an antibody, refers to a binding reaction that is determinative of the presence of a protein in a heterogeneous population of proteins and other biologics. Thus, under designated immunoassay conditions, the specified antibodies bind to a particular protein at least two times the background and do not substantially bind in a significant amount to other proteins present in the sample. Typically a specific or selective reaction will be at least twice background signal or noise and more typically more than 10 to 100 times background. Specific binding to an antibody under such conditions may require an antibody that is selected for its specificity for a particular protein Included in the invention are antibodies that bind to the UvrA polypeptides of the present invention. Such antibodies may include antibodies that bind to a UvrA polypeptide of the present invention and do not bind to the UvrA polypeptide in *E. coli* (having the amino acid sequence of GenBank Accession Number AAA24754) or the UvrA polypeptide of *B. subtilus* (having the amino acid sequence of GenBank Accession Number F69729). The present invention also includes antibodies that bind to the UvrB polypeptides of the present invention. Such antibodies may include antibodies that bind to a UvrB polypeptide of the present invention and do not bind to the UvrB polypeptide in *E. coli* (having the amino acid sequence of GenBank Accession Number P07025) or the UvrB polypeptide of *B. subtilus* (having the amino acid sequence of GenBank Accession Number G69729).

Methods of Use:

The thermostabile polypeptides of the present invention may be used within diagnostic systems, providing methods for detecting DNA damage in a sample of double-stranded DNA. Preferably, such diagnostic systems are in kit form. Kits are described in greater detail herein.

One embodiment of the detection method of the present invention makes use of the damage-specific recognition property of the UvrA and UvrB polypeptides of the present invention to bind to, and quantify, a wide range of damaged DNA adducts in the sample of double-stranded DNA. In this method a UvrA polyeptide of the present invention, a UvrB polypeptide of the present invention, and a double-stranded DNA are combined to form a mixture. The mixture is incubated under conditions that allow for the formation of a complex of the UvrA polypeptide and the UvrB polypeptide at the site of the damaged DNA. Incubation conditions may be, but are not limited to, conditions described herein. For example, UvrA and UvrB polypeptides may be incubated with the double-stranded DNA sample in a UvrABC binding buffer in the presence or absence of 1 mM ATP. The UvrABC buffer may be about 25–100 mM Tris-HCl, more preferably about 50 mM Tris-HCl, about pH 7–10, more preferably about pH 7.5, about 25–500 mM KCl, more preferably about 50 mM KCl, about 10 mM MgCl2, about 5 mM dithiothreitol. The incubation may take place at a temperature ranging from about 37° C. to about 90° C., more preferably from about 50° C. to about 85° C., most preferably at about 55° C. or at about 65° C., for a time period of about 5 to about 30 minutes, preferably about 10 minutes to about 20 minutes, more preferably about 15 minutes. The UvrA and UvrB polypeptides may be provided at about a 10 to about 100 molar fold excess, more preferably about a 30 to about a 50 molar fold excess, over the concentration of damaged DNA sites. For example, if 1 nM of a plamid containing one DNA adduct per plasmid molecule is used in the assay, about 10 nM to about 100 nM, more preferably about 30 to 50 nM of each of a UvrA polypeptide and a UvrB polypeptide may be added to the assay mixture.

The presence of a complex is then detected, wherein the presence of a complex indicates the presence of DNA damage. The formation of a complex of a UvrA polypeptide, a UvrB polypeptide and DNA (also called a UvrA:UvrB:DNA complex) may be quantified, for example, by the gel mobility shift assay, as described herein. In another aspect, a fluorescently labelled anti-UvrB antibody may be used to detect and quantify the formation of a UvrA:UvrB:DNA complex. Alternatively, a fluorescently labeled UvrB polypeptide, produced as described in U.S. Pat. No. 6,132,968, may be used to form a fluorescently labeled UvrB:UvrA:DNA complex. In addition to the gel mobility shift assay, Western blotting procedures and capillary electrophoresis may be used to detect and quantify the UvrA:UvrB:DNA complex. Capillary electrophoresis, as described, for example, by Hjerten et al., U.S. Pat. No. 5,114,551, includes the use of capillaries which are filled either with a gel, for example, polyacrylamide, or with buffer. The use of capillary electrophoresis provides rapid sample analysis and permits the use of small sample volumes (see, for example, Xian et al. (1996) *Proc. Nail. Acad Sci. USA* 93, 86–90).

The importance of the methods of the present invention is reflected by the broad substrate range recognized by the polypeptides of the present invention. Also contributing to the importance of the methods of the present invention is the long-term stability of the assay imparted by the thermostability of the UvrA and UvrB polypeptides of the present invention. DNA lesions recognized by the polypeptides of the present invention include UV-induced photoproducts, alkylated bases and anti-cancer drug-DNA adducts. The UvrA and UvrB polypeptides may be used to specifically bind and quantify a wide range of DNA base modifications, including, but not limited to, UV dimers (e.g., cyclobutane pyrimidine dimers and 6,4-photoproducts), polycyclic aromatic hydrocarbon adducts (e.g., benzo(a)pyrene and dimethylbenzanthracene), cis-platinum adducts, aflatoxin adducts, psoralen adducts, anthramycin adducts, mitomycin C adducts, N-acetoxy-2-aminofluorene adducts, and N-hydroxy-2-aminofluorene adducts.

Double stranded DNA may be obtained from a wide range of sources and prepared by methods well known in the art. For example, a double stranded DNA may be obtained from an in vitro system, such as cell or tissue culture. Double stranded DNA may also be obtained from subjects. For example, double stranded DNA may be obtained from a subject, including a human subject, undergoing chemotherapy for cancer or exposed to a gentotoxin.

The methods of the present invention may be used to monitor the efficacy of chemotherapy, by monitoring the therapy's effect on accumulated DNA damage. This may be accomplished by taking an initial double stranded DNA sample from the patient prior to the initiation of chemotherapy, and taking one or more subsequent double stranded DNA samples after the initiation of chemotherapy. The extent of DNA damage in each sample is determined by the methods described herein. The efficacy of the chemotherapy is directly proportional to DNA damage assessed in the sample obtained after the initiation of chemotherapy. One widely used anti-cancer drug, cisplatin, reacts with DNA to inhibit DNA replication and results in cell death. DNA adducts resulting from cisplatin treatment are often rapidly repaired by tumor cells and can therefore be inactivated. The development of a rapid and efficient method for the quantitation of cisplatin-DNA adducts in patients undergoing cisplatin chemotherapy would allow more beneficial treatment strategies and the evaluation of possible chemotherapeutic agents.

In one aspect, the methods of the present invention may be used to detect and quantify the level of UV exposure in a subject. The methods of the present invention can also be used in molecular epidemiology studies, for example, quantifying the extent of UV-induced pyridine dimers in a population of subjects.

In another aspect, the methods of the present invention may be used for detecting the effect of environmental genotoxins. The extent of DNA damage in a biological sample taken from a subject potentially exposed to a genotoxin, such as an organic or inorganic compound, for example from a chemical spill site, may be compared to a sample taken from control subject not exposed to the gentotoxin. In this case the subject may be, for example, a microbe, a plant, or an animal, including a human subject.

In a preferred embodiment, the present methods use at least two double stranded DNA samples, generally, a control sample and a test sample. The control sample may be a duplicate of the test sample which has not been exposed to DNA damage, or it may be a sample taken prior to the initiation of chemotherapy.

Kits:

The present invention also provides kits for detecting damaged DNA. The kits include a UvrA polypeptide of the present invention and/or UvrB polypeptide of the present invention, in a suitable packaging material in an amount sufficient for at least one assay. Optionally, the kit may also include an antibody that binds to a UvrA polypeptide or an antibody that binds to an UvrB polypeptide. Additionally, the kit may include other reagents such as buffers and solutions needed to practice the invention are also included. Instructions for use of the packaged polypeptide or primer pair are also typically included.

As used herein, the phrase "packaging material" refers to one or more physical structures used to house the contents of the kit. The packaging material is constructed by well known methods, preferably to provide a sterile, contaminant-free environment. The packaging material has a label which indicates that the polypeptide can be used for detecting damaged DNA. In addition, the packaging material contains instructions indicating how the materials within the kit are employed to detect damaged DNA. As used herein, the term "package" refers to a solid matrix or material such as glass, plastic, paper, foil, and the like, capable of holding within fixed limits a polypeptide. Thus, for example, a package can be a glass vial used to contain milligram quantities of a polypeptide. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

The present invention is illustrated by the following examples. It is to be understood that the particular examples, materials, amounts, and procedures are to be interpreted broadly in accordance with the scope and spirit of the invention as set forth herein.

EXAMPLES

Example 1

Cloning and Expression of the uvrA Gene from Thermophilic Eubacterium, *Bacillus caldotenax*

Enzymes and Chemicals.

The DNA modification enzymes $T_4$ DNA ligase and calf intestinal phosphatase (CIP) were obtained from Promega (Madison, Wis.). Restriction endonucleases were obtained from Promega, Gibco (now Invitrogen, Carlsbad, Calif.) and New England Biolabs (NEB; Beverly, Mass.); Pyrococcus furiosus (Pfu) DNA polymerase was obtained from Stratagene (La Jolla, Calif.). Isopropyl-β-D-thiogalactopyranoside (IPTG) was from Sigma (St. Louis, Mo.). ATP was from Roche (Indianapolis, Ind.), and γ-$[^{32}P]$-ATP was purchased from Dupont (Wilmington, Del.). All other chemicals, if not specified otherwise, were obtained from Fisher Scientific (Pittsburgh, Pa.).

The T7 IMPACT System (New England BioLabs; Beverly, Mass.) was used for protein purification. IMPACT (Intein Mediated Purification with an Affinity Chitin-binding Tag) utilizes the inducible cleavage activity of engineered protein splicing elements (termed inteins) to purify recombinant proteins by a single affinity column. See Chong et al., *Gene* 192, 27–281 (1997); Chong et al., *Nucl. Acids Res.* 26, 5109–5115 (1998); Chong et al., *J. Biol. Chem.* 273, 10567–77 (1998); and Chong et al., *J. Biol. Chem.* 271, 22159–22168 (1996). This system distinguishes itself from other protein fusion systems by its ability to separate a recombinant protein from the affinity tag without the use of a protease.

The DNA oligonucleotide primers used in PCR were synthesized on a 394 DNA/RNA Synthesizer (Applied Biosystems, Foster City, Calif.).

*E. coli* UvrA protein was purified from *E. coli* MH1 Δuvr4 AuvrA containing plasmid pSST10 as described previously (Zou et al., *Biochemistry* 34, 13582–13593 (1995)). *E. coli* UvrB and UvrC were overproduced from *E coli* strain CH296 containing plasmids pUC211 and pDR374, and purified as described previously (Zou et al., *J. Biol. Chem.* 273, 12887–12892 (1998); Sancar et al., *DNA Repair: A Laboratory Manual of Research Procedures* 3, 481–510 (1987), Marcel Dekker Inc., New York).

Strains, Media, and Plasmids.

The *E. coli* strains used for plasmid DNA manipulations were: DH5α (recA1 endA1 gyrA96 thi-1 hsdR17 supE44 DlacU196 (θ80 lacZΔM15) relA1); and XL-1 Blue (recA1 endA1 gyrA96 thi-1 hsdR17 supE44 relA1 lac[F′ proAB lacI$^q$ ZΔM15 Tn10 (Tet$^R$)].

The *E. coli* strain used for the screening of the Bca library was: UNCI 158 (thr-1 ara-14 leuB6 Δ(gpt-proA)$_{62}$ lacY1 tsx-33 gsr'-O glnV44 (AS) galK2 (Oc) LAM⁻ rac-O hisG4 (Oc) rtbD1 mg1-51 rpoS396 (Am) rpsL31 (strR) kdgK51 xylA5 mt1-1 argE3 (Oc) thi-1 uvrA::Tn10 Tet$^R$).

The *E. coli* strains used for overexpression of Bca UvrA protein were: BL21 (DE3) F⁻ ompT hsdS gal dcm(DE3) [λcIts87 indA1 Sam7 nin5 lacUV5-T7 gene1]; HMS174 (DE3) F⁻ recAI hsdR Rif$^R$ (DE3) [λcIts87 indA1 Sam7 nin5 lacUV5-T7 gene 1]; C41 (DE3)—a derivative of BL21 (DE3) (Miroux and Walker, *J. Mol. Biol.* 260, 289–298 (1996)); and C43(DE3)—derived from C41(DE3) (Miroux and Walker, *J. Mol. Biol.* 260, 289–298 (1996)).

*Bacillus caldotenax* (Bca) cells were grown at the Centre for Applied Microbiology and Research, Wiltshire, UK, under conditions described in Sharp and Raven, *Applied Microbial Physiology: A Practical Approach*, eds. Rhodes, P. M., and Stanbury, P. F. (Oxford University Press, Oxford, U.K.), pp. 23–52 (1997)). The *E. coli* cells were grown in LB, TYE, or 2×TY medium (Sambrook et al., (1989) *Molecular Cloning: A Laboratory Manual*, Cold Spring Harbor Laboratory, Cold Spring Harbor, N.Y.).

The plasmids used were pUC8.0, pUC8.1, pUC8.2, pUC18, and pTYB1 (NEB T7 IMPACT system manual). In order to achieve high expression and rapid purification of the Bca UvrA protein in *E. coli*, the uvrA gene of *B. caldotenax* was subcloned into pTYBI vector of T7 IMPACT System. This expression system is based on an in-frame three part fusion between the target gene (Bca uvrA), an intein (from *S. cerevisiae*), and a chitin binding domain ((CBD); from *Bacillus circulans*). When crude extracts of cell from induced *E. coli* expression system are passed through a chitin column, the fusion protein binds to the column while all other contaminants are washed through the column. The fusion protein then undergoes an intein-mediated self cleavage in the presence of DTT, resulting in elution of the target protein while the intein-CBD fusion partner remains bound to the column. The pTYBI vector, 7280 bp, uses the T7 promoter to provide stringent control of the gene expression. This vector carries the lacI gene encoding Lac repressor for suppression of the fusion gene in the absence of IPTG. Two tandem transcription terminators (rrnB T1T2) placed upstream of the promoter minimize background readthrough transcription. The vector also contains the origin of Ml3 bacteriophage replication and the b/a gene which conveys ampicillin resistance to the host strain.

Construction of Genomic Library of *B. caldotenax*.

Genomic DNA isolated from *Bacillus caldotenax* cell paste (Marmur (1961) *J. Mol. Biol.* 3, 208–218) was digested completely with BamHI. DNA fragments (2–10 kb) were isolated from low melting agarose. These fragments were used for ligation into BamHI-digested and CIP-dephosphorylated pUC8 vector series –8.0, 8.1, and 8.2 which allow the construction of fusion between lacZ and target protein in all three possible reading frames. The ligation mixtures were electroporated into *E. coli* DH5α and total plasmid DNA was isolated from all resulting ampicillin resistant ((AmpR) transformants. The isolated plasmid DNA representing three Bca sublibraries was used in screening procedures.

Screening of Bca Library for UvrA Protein.

The Bca genomic DNA libraries were transformed into *E. coli* UvrA⁻ cells (UNCI 158) and resulting Amp$^R$ transformants were examined for complementation of ultraviolet (UV) sensitivity of the host cells. All Amp$^R$ colonies were resuspended in PBS, diluted to OD$_{550}$=0.3 and irradiated in the dark with UV light using germicidal lamp to deliver dosages of 25, 50, 75, and 100 Joules/meter² (J/m²). The cells surviving UV dose of 75 and 100 J/m², after appropriate dilutions, were either re-irradiated with 75 J/m² UV-dose or treated with UV-mimetic compound 4-nitroquinoline oxide (4NQO). The plasmid DNA from UV-resistant (UV$^R$) and 4Nqo-resistant (4NQO$^R$) single colonies was isolated and retransformed into *E. coli* UvrA⁻ cells to confirm that UV-resistance was due to plasmid DNA and not UvrA⁻ reversion in host cells.

As shown in Table 1, *E. coli* UNC1158 transformed with a pUC8.1Bca genomic DNA sublibrary exhibited the highest resistance to UV-irradiation and 4NQO. Plasmid DNA from ten randomly picked Amp$^R$ UV$^R$ *E. coli* UNC 1158/pUC8.1Bc colonies was isolated and digested with HindIII and EcoRI restriction endonucleases to determine the size of inserted Bca DNA; 8 out of 10 colonies contained the identical ~4.4 kb insert. Plasmid DNA from clone No.7 was used in all further experiments. *E. coli* UNC1158 cells were transformed with pUC8.1c7 plasmid DNA and the UV sensitivity of resulting transformants was compared in a UV-spot test (5, 10, 15 J/m²) to that of UNC1158/pUC18 (negative control) and UNCI 158/pSST10 (positive control with plasmid encoded *E. coli* uvrA gene), respectively. The negative control exhibited significantly higher UV sensitivity than the other two transformants. These results confirmed that the UV resistance of *E. coli* UNC1158/pUC8.1Bc7 clone was due to the ~4.4 kb-fragment of Bca genomic DNA cloned in pUC8.1 vector, and not caused by a reversion mutation or recombination event in the host cells. In addition, the results suggested that the cloned 4.4 kb fragment contained the uvrA gene of *B. caldotenax* capable of complementing *E. coli* UvrA subunit of the UvrABC endonuclease in vivo.

TABLE 1

UV- and 4NQO-resistance of *E. coli* UNC1158 transformed with Bca genomic DNA sublibraries (pUC8.0Bca, pUC8.1Bca, pUC8.2Bca).

| Bca sublibrary | 1ˢᵗ UV irradiation (Jm⁻²) | | | | 2ⁿᵈ irradiation (Jm⁻²) | 4NQO treatment |
|---|---|---|---|---|---|---|
| | 25 | 50 | 75 | 100 | 75 | 100 mg/ml |
| pUC8.0Bca | + | 118 | 15 | 3 | >500 | ~100 |
| pUC8.1Bca | + | 150 | 9 | 4 | confluent | >1000 |
| pUC8.2Bca | + | 3 | 0 | 0 | 7 | 0 |

Sequencing of the Bca uvrA Gene.

The plasmid conferring $UV^R$ and $4NQO^R$ phenotype of *E. coli* UvrA⁻ cells was digested with SalI restriction enzyme, and three fragments of size 2 kb, 1.2 kb, and 0.5 kb were subcloned into pUC 18 vector and sequenced on an ABI PRIZM 310 Genetic Analyzer (Applied Biosystems, Foster City, Calif.) using pUC forward and reverse primers, respectively. The sequencing results obtained were used to design internal Bca uvrA gene specific sense and antisense primers for subsequent rounds of sequencing the cloned gene. Nucleotide sequencing of the $UV^R$ $4NQO^R$ conferring DNA fragment identified an open reading frame of 2,859 nucleotides encoding a protein of ~106 kilodaltons (kDa). The complete nucleotide sequence of Bca uvrA gene (SEQ ID NO:1) with aligned amino acid sequence (SEQ ID NO:2) is shown in FIG. 1. Sequence alignments showed the Bca uvrA sequence to have 71% identity with that of *Bacillus subtilis*. The deduced amino acid sequence of Bca UvrA protein depicts a characteristic duplicated structure, including two Walker A-type ATP binding sites (GKS consensus motif), and two zinc-finger DNA binding motifs, were found.

Table 2 provides comparison of amino acid sequence identity (%) and zinc finger DNA binding motif, C—$X_2$—C, in various mesophilic and thermophilic UvrA proteins. The amino acid sequence of Bca UvrA protein showed higher than 50% identity with all UvrA proteins with known sequence (52—82%). As expected, the highest identity was observed with *B. subtilis* UvrA protein (82.2%), but unexpectedly, the second and third highest identity was found with phylogenetically distant organisms, both thermophiles, namely Archaeon *Meihanococcus thermoautotrophicum* (64.8%), and Eubacterium *Thermus thermophilus* (63.5%). The lowest amino acid sequence identity was found with UvrA protein from *Helicohacter pyroli* (52.6%).

TABLE 2

Comparison of amino acid sequence identity (%), and zinc finger DNA binding motif, C-$X_2$-C, in various mesophilic and thermophilic UvrA proteins.

| Organism | % identity | Zinc-finger 1 | Zinc-finger 2 | thermophile |
|---|---|---|---|---|
| Bacillus caldotenax | 100 | CPYC (SEQ ID NO: 45) ... CPDC (SEQ ID NO: 54) | CEAC (SEQ ID NO: 63) ... CEVC (SEQ ID NO: 66) | + |
| Bacillus subtilis | 82.2 | CPHC (SEQ ID NO: 46) ... CPTC (SEQ ID NO: 55) | CEAC (SEQ ID NO: 63) ... CEVC (SEQ ID NO: 66) | + |
| M. thermoautotrophicum* | 64.8 | CPGT (SEQ ID NO: 47) ... CPEC (SEQ ID NO: 56) | CEAC (SEQ ID NO: 63) ... CEVC (SEQ ID NO: 66) | + |
| Thermus thermophilus | 63.5 | CPEH (SEQ ID NO: 48) ... CPAC (SEQ ID NO: 57) | CEAC (SEQ ID NO: 63) ... CEVC (SEQ ID NO: 66) | – |
| Micrococcus luteus | 61.9 | CPNG (SEQ ID NO: 49) ... CPEC (SEQ ID NO: 56) | CEAC (SEQ ID NO: 63) ... CEVC (SEQ ID NO: 66) | – |
| Escherichia coli | 61.5 | CPIC (SEQ ID NO: 50) ... CPTC (SEQ ID NO: 55) | CEAC (SEQ ID NO: 63) ... CDQC (SEQ ID NO: 51) | – |
| Haemophilus influenzae | 61.3 | CPHC (SEQ ID NO: 46) ... CPTC (SEQ ID NO: 55) | CEAC (SEQ ID NO: 63) ... CDQC (SEQ ID NO: 51) | – |
| Neisseria gonorrhoeae | 61.2 | CPVC (SEQ ID NO: 45) ... CPTC (SEQ ID NO: 55) | CEAC (SEQ ID NO: 63) ... CEYC (SEQ ID NO: 67) | – |
| Salmonella typhimurium | 61.0 | CPIC (SEQ ID NO: 50) ... CPTC (SEQ ID NO: 55) | CEAC (SEQ ID NO: 63) ... CDQC (SEQ ID NO: 51) | – |
| Aquifex aoelicus | 60.7 | CPEH (SEQ ID NO: 48) ... CPSC (SEQ ID NO: 58) | CEAC (SEQ ID NO: 63) ... CEVC (SEQ ID NO: 66) | + |
| Synechocystis sp. | 58.7 | CPEH (SEQ ID NO: 48) ... CPDC (SEQ ID NO: 54) | CEAC (SEQ ID NO: 59) ... CDVC (SEQ ID NO: 68) | – |
| Thermatoga maritima | 58.4 | CPVC (SEQ ID NO: 45) ... CPNC (SEQ ID NO: 59) | CEAC (SEQ ID NO: 63) ... CDVC (SEQ ID NO: 68) | + |
| Deinococcus radiodurans | 58.0 | CPEH (SEQ ID NO: 48) ... CPAC (SEQ ID NO: 57) | CEHC (SEQ ID NO: 64) ... CEVC (SEQ ID NO: 66) | – |
| Mycoplasma pneumoniae | 56.5 | CDQC (SEQ ID NO: 51) ... CEYC (SEQ ID NO: 60) | CDKC (SEQ ID NO: 52) ... CEMC (SEQ ID NO: 69) | – |
| Mycoplasma genitalium | 56.5 | CDKC (SEQ ID NO: 52) ... CSYC (SEQ ID NO: 61) | CDKC (SEQ ID NO: 52) ... CEVC (SEQ ID NO: 66) | – |

TABLE 2-continued

Comparison of amino acid sequence identity (%),
and zinc finger DNA binding motif, C-X$_2$-C, in
various mesophilic and thermophilic UvrA proteins.

| Organism | % identity | Zinc-finger 1 | Zinc-finger 2 | thermo-phile |
|---|---|---|---|---|
| Helicobacter pylori | 52.6 | CFKC (SEQ ID NO: 53) . . . CESC (SEQ ID NO: 62) | CEKC (SEQ ID NO: 65) . . . CDSC (SEQ ID NO: 70) | – |

Table 2: Comparison of amino acid sequence identity (%), and zinc finger DNA binding motif, CXXC (SEQ ID NO: 71), in various mesophilic and thermophilic UvrA proteins.

Comparison of Bca UvrA protein zinc-finger DNA binding consensus sequences, C—X$_2$—C—X$_{10-20}$—C—X$_2$—C (SEQ ID NO:39), shown in FIG. 4, indicates a remarkable identity with that of *B. subtilis:* 93% identity in zinc finger 1 (Zf1) sequence and 96% identity in zinc finger 2 (Zf2) sequence and with that of *E. coli:* 75% identity (79% similarity) in Zf1 and 78% identity (93% similarity) in Zf2.

The fact that mesophilic eubacterium *B. subtilis* and thermophilic eubacterium *B. caldotenax* belong to the same genus, makes them very suitable candidates for amino acid content and sequence comparisons and for an analysis of the general features important for the thermostability of the proteins.

Bsu UvrA (M$_w$=105,641) contains 952 amino acid residues, Bca UvrA (M$_w$=106,031) is slightly bigger, containing 957 amino acid residues. Because of a very high level of amino acid sequence identity (82.2%) and similarity (88.5%) between the two proteins, the differences in frequency of individual amino acids are relatively small, with the biggest difference in amounts of Ser (57 residues in Bsu, 45 residues in Bca) and Lys (64 vs 54 residues). Altogether, there are five amino acid residues with the equal frequency in both UvrA proteins, namely Cys, His, Lys, Asn, and Glu. It is thought that Pro residues increase the enthalpy of the native state of the protein, thereby increase the stability of the protein (Watanabe et al., *Eur. J. Biochem.* 226, 277–283 (1994)). The number of Pro residues in Bca UvrA protein is increased by three residues. It has been suggested that the frequency of Asn and Met residues is reduced in thermostable proteins due to their instability at high temperature. However, this is the case only for Met, which is reduced in Bca UvrA by three residues, the amount of Asn residues is the same in both Bsu and Bca proteins.

These findings might be explained by the fact that *B. caldotenax* is a moderate thermophile with optimal growth temperature ~65° C., while Asn and Met residues are instable at much higher temperatures (>90° C.). It has been also shown that the number of Arg residues was increased substantially in Tih UvrA protein as compared with Eco UvrA (from 66 to 81 residues). This change is believed to contribute to the enhancement in the number of hydrogen bonds to stabilize the protein structure (Yamamoto et al., *Gene* 171, 103–106 (1996)). This assumption is supported by the present data, indicating a significant increase of Arg residues in Bca UvrA (67 residues) compared to its mesophilic counterpart in *B.subtilis* (59 residues).

Subcloning of the Bca uvrA Gene for Expression in *E. coli*

For subcloning of the uvrA gene of *B. caldotenax* into pTYB1 expression vector (IMPACT System, New England Biolabs), two DNA oligodeoxyribonucleotides, 5' BcTA sense primer, containing a NdeI-restriction site GCGAC-CGCATATGGATAAAATTGTCGTCAAAGG (SEQ ID NO:20), and 3' BcTA antisense primer, containing a SapI-restriction site TCTCCCGCTCTTCCGCACGCCTTCAC-CGCTTCATAT T (SEQ ID NO:21) were synthesized. The Bca uvrA gene was amplified by polymerase chain reaction (PCR) in a 100 microliter (μl)-reaction mixture containing 2.5 millimolar (mM) MgCl$_2$, 200 micromolar (μM) dNTP's, 20 picomolar (pmol) of each primer, 100 nanogram (ng) Bca genomic DNA and 2.5 units (U) Pfu DNA polymerase using following conditions: I cycle: 94° C. for 2 minutes; 25 cycles: 94° C. for 45 seconds, 52° C. for 45 seconds, 72° C. for 6 minutes, followed by 72° C. for 10 minutes.

The PCR product was extracted with phenol/chloroform/isoamylalcohol (24:24:1) and purified using clean up kit available from Promega (Madison, Wis.). Purified PCR product as well as vector pTYB I were digested with NdeI+SapI, vector was dephosphorylated with CIP, both DNA fragments were purified from the SeaKem agarose following gel electrophoresis and used in ligation under standard conditions. Ligation mixture was transformed into *E. coli* DH5α and XL-1 Blue competent cells using standard CaCl$_2$ method (Sambrook ct al., *Molecular Cloning: A Laboratory Manual*, Cold Spring Harbor Laboratory, Cold Spring Harbor, N.Y. (1989)). The plasmid from Amp$^R$ transformants was isolated, analyzed by digestion with restriction endonucleases and sequenced to confirm that no mutations were introduced during amplification of the gene by PCR. The resulting recombinant plasmid DNA, pTYB1 Bca uvrA was transformed into *E. coli* BL2I(DE3) and *E. coli* HMS174(DE3) host cells, respectively to compare the level of Bca UvrA protein expression in these strains.

For overexpression of Bca UvrA protein in *E. coli* cells, the fresh Amp$^R$ transformants were used to inoculate 2×TY medium, containing 100 μg/ml ampicillin, first in a small scale (10 ml), then in a large scale (9 to 16 liters) to an optical density at 600 nm (OD$_{600}$) of 0.05 and were grown for 2–2.5 hours at 37° C. with shaking until OD$_{600}$=0.5–0.6 when IPTG (final concentration of 1 mM) was added. The IPTG induction of Bca UvrA was performed at 30° C. for 3 hours with shaking (250 rpm). The induced culture was centrifuged and cell pellets were stored at −20° C.

Purification of Bca UvrA Protein

Cell extracts were prepared by resuspending cells in 1/50 volume of column/wash buffer (20 mM TrisCl, pH 8.00; 500 mM NaCl; 0.1 mM EDTA; 0.5% Triton X-100) containing 5 μg/ml leupeptin and 10 μg/ml pepstatin and sonicating (two pulses of 30 seconds at 18 μm and 20 μm peak-to-peak distance, respectively); phenylmethylsulfonyl fluoride (PMSF) was added to a final concentration of 50 μM immediately after the second sonication. Sonicate was clarified by centrifugation (13,200 rpm for 15 minutes at 4° C.) and supernatant was used for loading the chitin column (10 ml). Aliquots of sonicate and cleared extract, respectively were taken and separated by polyacrylamide gel electrophoresis (PAGE) to examine the solubility of overexpressed protein.

UvrA protein from *E. coli* cells was purified following the T7 IMPACT system manual. Briefly, chitin beads were equilibrated with 15 volumes of column/wash buffer containing 0.5 mM PMSF. The cell extract was loaded onto chitin column at a rate of 0.5 ml/min. The column was washed with at least 30 volumes of column/wash buffer at a flow rate of 1 ml/min. The on-column cleavage of the fusion protein (Bca UvrA-intein-CBD) was initiated by flushing the column quickly with two column volumes of freshly prepared cleavage buffer (20 mM Tris.Cl, pH 8.00; 500 mM NaCl; 0.1 mM EDTA; 30 mM dithiothreitol (DTT)). A third column volume of cleavage buffer was added and cleavage was allowed to continue at 4° C. overnight. Bca UvrA was eluted in three column volumes using additional cleavage buffer (without DTT) in one milliliter fractions. The approximate protein concentration of individual proteins was estimated by BioRad protein assay (BioRad Laboratories, Richmond, Calif.) and the fractions containing protein were examined using PAGE for molecular weight and purity of isolated protein. Samples from major steps in the overproduction and purification of Bca UvrA protein were separated on a 10% SDS-polyacrylamide gel, which was stained with Coomassie Blue and photographed. Such samples included samples from cell extracts of non-induced cultures, IPTG-induced cell cultures and fractions (approximately 1-ml fractions) after cleavage with DTT and elution from the chitin column, respectively. The appropriate fractions were pooled and dialyzed against two changes of storage buffer (50 mM TrisCl, pH 7.50; 100 mM KCl; 0.1 mM EDTA; 50% glycerol). The purified UvrA protein was stored at −20° C.

Protein Sequencing

To determine the N-terminal amino acid sequence of the complete as well as truncated version of Bca UvrA proteins, the proteins separated on the SDS-PAGE were electroblotted onto a polyvinylidene difluoride membrane at 1 mA/cm$^2$ for 4 hours. The two protein bands, visualized using Coomassie Blue, were cut out and analyzed by a protein sequencer (Applied Biosystems).

Protein Concentrations.

The concentrations of protein fraction eluted from the chitin column were determined using the Bio-Rad protein assay kit with bovine serum albumin as a standard. The *B.caldotenax* UvrA protein contains two tryptophan and thirty-five tyrosine residues. The molar extinction coefficient was calculated to be 63,150 at an absorption maximum around 280 nm using the 320 nm correction procedure described previously (Kuramitsu et al., *Biochemistry* 29, 5469–5476 (1990)).

Overexpression of Bca UvrA Protein.

The Bca uvrA gene was subcloned into pTYB I vector as an NdeI-SapI fragment by PCR using Pfu DNA polymerase. Seven out of eight Amp$^R$ transformants (in *E. coli* XL-I Blue host cells) contained Bca uvrA gene, two clones were selected and resequenced to confirm that no mutations were introduced during amplification by PCR.

To achieve a maximal overexpression of Bca UvrA protein, the following *E. coli* strains, containing λ prophage (DE3) carrying T7 RNA polymerase gene 1 were tested: BL21 is deficient in OmpT protease, it is a B strain [$r_B^-$ $m_B^-$]; HMS 174 is protease-proficient, recA1 mutant, Rif$^R$, K-12 strain [$r_K^-$ $m_K^+$]; C41 was derived from BL21, and C43 is a derivative of C41 (Miroux and Walker, *J. Mol. Biol.* 260, 289–29828 (1996)). The mutations in C41 and C43 strains have not been yet identified, but they are believed to affect the amount or activity of T7 RNA polymerase. The pTYB1uvrA$_1$ plasmid was used for transformation of *E. coli* BL21(DE3) and HMS174(DE3). A small scale (10 ml) induction (3 hours, 30° C., 1 mM IPTG) of the cells showed a relatively low expression of the fusion protein (~160 kDa) with a slightly higher induction level in *E. coli* HMS174 (DE3).

Cell extract from 1 liter culture of *E. coli* HMS174(DE3)/pTYB1Bca uvrA induced under the same conditions as above, was applied on the chitin column, cleavage of the induced fusion protein was induced at 4° C. overnight with 30 mM DTT containing cleavage buffer and 1 ml-fractions were collected. Analysis on 10% SDS-PAGE indicates that the eluate contained two protein bands, a band about 106 kDa corresponding to full-size Bca UvrA and in addition, a protein of ~80 kDa. Western blot analysis indicated that both protein bands reacted with a rabbit polyclonal anti-Eco UvrA antibody. The PAGE analysis of the induced culture suggested the induction of two proteins of ~160 kDa and ~140 kDa. These results suggested an additional initiation of translation within Bca uvrA mRNA sequence. For this reason, the sequence of Bca uvrA gene was checked for the presence of an internal Shine-Dalgarno consensus sequence (AGGA) followed by a potential translation in frame initiation codon in the optimal distance (4–10 bp) from the ribosome binding site (RBS). Two potential internal translation initiation codons were found. The first in position 574 leading to synthesis of a truncated fusion 139 kDa protein (84 kDa Bca UvrA after cleavage with DTT on the chitin column), and the second in position 1645/1648 resulting in 100 kDa fusion protein (45 kDa Bca UvrA). PAGE analysis of purified Bca UvrA suggested the initiation of translation from the CTG initiation codon starting at position 574. NH$_2$-terminal protein sequencing confirmed that the CTG codon located at the position 574 within Bca uvrA gene serves as an internal translation initiation codon for synthesis of truncated ~84 kDa Bca UvrA protein.

Site-directed Mutagenesis of the Bca uvrA Gene

To mutagenize the internal Shine-Dalgarno consensus sequence from AGGA to AAGA, overlap PCR approach has been used (Ho et al., *Gene* 77, 51–59 (1989)). Briefly, complementary oligodeoxyribonucleotide primers and PCR were used to generate two DNA fragments with overlapping ends. These fragments were combined and the resulting fusion product was amplified further by PCR using 5' and 3' end primers, respectively. In PCR 1, BCTA sense (SEQ ID NO:20) and SD antisense CAGCTCAATGTCTTCCGT CAACTC (SEQ ID NO:22) primers were used to amplify 5' region of Bca uvrA gene. In PCR 2, SD sense primer GAGTTGACGGAAGAC ATTGAGCTG (SEQ ID NO:23) combined with BcTA antisense (SEQ ID NO:21) were used to amplify the 3' region of the uvrA gene. Pfu DNA polymerase was used in both reactions under following conditions: 94° C. for 2 minutes (pre-PCR); 94° C. for 45 seconds, 55° C. for 45 seconds, 72° C. for either for 1 minute 25 seconds (PCR 1) or 4 minutes 45 seconds (PCR 2) for 25 cycles; 72° C. for 10 minutes (1 cycle). The PCR products, PCR 1 (574 bp) and PCR 2 (2.285 kb) were phenol/chloroform and chloroform extracted, ethanol precipitated and purified from 1% SeaKem agarose. Purified DNA fragments (20 ng of each) were used as template DNA for overlap PCR using BcTA sense (SEQ ID NO:20) and antisense primers (SEQ ID NO:21) and Pfu DNA polymerase under same conditions as previously, except the extension time was increased to 6 minutes. The resultant PCR product of approximately 2.9 kb was digested with NdeI and SapI restriction endonucleases and subcloned into pTYB1 vector. The inserted Bca uvrA gene sequence was checked for the presence of any mutations introduced by PCR. The resulting plasmid, PTYB1uvrA$_{SD}$ was used to transform appropriate E. coli cells to test the expression of Bca UvrA protein with AAGA sequence.

In order to achieve an increased expression of Bca UvrA protein using T7 expression system, three different mutagenized constructs of the Bca uvrA gene were made. In the first construct (SD$_{564}$), an internal Shine-Dalgarno sequence at position 564 was removed, by site-directed mutagenesis, as described above. In the second construct (UvrAm$_{MK}$), a lysine was introduced as the second amino acid residue in the Bca UvrA protein by the insertion of two codons (ATG and AAA, coding for Met and Lys, respectively) upstream of the initiation codon ATG of the Bca uvrA gene. It has been found in several cases that this change leads to a significantly higher level of expression of the respective proteins (Ikemura, J. Mol. Biol. 146, 1–21 (1981); and Belagaje et al., Protein Science 6, 1953–1962 (1997)). In the third construct (UvrA$_{CUO}$), codon usage at the 5' end of Bca uvrA gene was optimized. This optimization was performed in two steps. In the first step, the first 24 codons of wild-type Bca uvrA gene were substituted by codons preferentially used in E. coli using synthetic oligodeoxyribonucleotides. In the second step, the nucleotide sequence encoding the following 41 amino acid residues of the Bca UvrA protein (which are identical to those of E. coli UvrA protein except two conservative substitutions) were substituted with the E. coli nucleotide sequence.

Figure 5B:
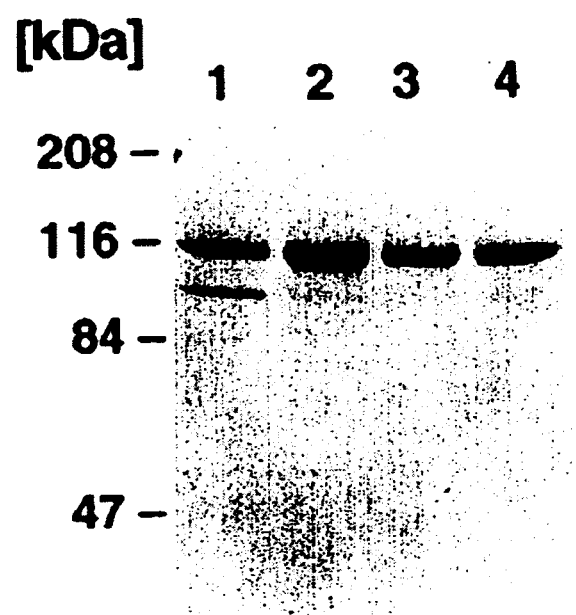
FIG. 5B is a comparison of overproduction and purification of various versions of Bca UvrA protein. Lane 1, wild-type UvrA; lane 2, UvrA with 5'-terminus codon usage optimized (UvrA$_{CUO}$); lane 3, UvrA with internal Shine-Delagarno site at position 564 removed (UvrA$_{SD}$); lane 4, UvrA with Lys introduced as the second amino acid residue (UvrA$_{MK}$).

Samples from major steps in the overproduction and purification of Bca UvrA protein were separated on a 10% SDS-polyacrylamide gel, which was stained with Coomassie Blue and photographed. FIG. 5B shows a comparison of the expression of all versions of the Bca UvrA protein. As shown in lane 3, SD$_{564}$ (with internal SD sequence at position 564 removed) results in the removal of the truncated Bca UvrA protein band. For both the UvrA$_{MK}$ (lysine as the second amino acid residue) and the UvrA$_{CUO}$ (5' end codon usage optimization) constructs a significant reduction in the ~84 kDa truncated Bca UvrA protein synthesis was observed. However, comparison of the yield of Bca UvrA protein among all three mutagenized constructs did not show a significant improvement, only a slightly higher expression level for the UvrA$_{CUO}$ construct (see FIG. 5B, lane 2). For this reason, as well as because UvrA$_{SD}$ was the only construct with wild-type amino acid sequence of Bca UvrA protein, the SD$_{564}$ construct was used in large-scale purification and in all of the following experiments. Lanes 4–9 of FIG. 5A show the yield and purity of first six fractions of Bca UvrA protein (SD$_{564}$ version) eluted from the chitin column. As shown in lane 2, the overexpression of fusion protein (Bca UvrA-intein-CBD) is still relatively low, reaching ~0.5 mg-1 mg of purified protein per liter of IPTG-induced culture of E. coli BL21 (DE3), which is about 5–10-fold higher yield than in the case of original version.

The expression of full length Bca UvrA protein (as confirmed by N-terminal sequencing of the protein) under various conditions of IPTG concentration, induction time, growth media and temperature, using various E. coli host strains was tested. However, none of these conditions led to a substantial change of Bca UvrA expression. One of the reasons for low Bca UvrA expression in E. coli could be inefficient translation of mRNA, since genes under T7 promoter are generally transcribed very efficiently (Studier and Moffatt, J. Mol. Biol. 189, 113–130(1986); and Dubendorff and Studier, J. Mol. Biol. 219, 45–59 (1991)). In addition, their data showed that mRNAs transcribed by T7 RNA polymerase are relatively stable in vivo, accumulating to level apparent in total cellular RNA. Some of this apparent stability might result from the fact that these mRNAs are very long and it takes a long time for cellular exonucleases to digest them, or T7 RNA polymerase may be able to produce mRNA so rapidly that the capacity of the cell to degrade it becomes overloaded (Studier and Moffatt, J. Mol. Biol. 189, 113–130 (1986)). The organization of the 5'end of both Bca and Eco uvrA genes is very similar (6 and 5 AT-rich codons, followed by a stretch of 13 and 12 GC's, respectively). This means that first 21 nucleotides of Bca uvrA gene contain about 71% AT, reducing secondary structure within mRNA. Also, the introduction of a lysine codon AAA which is the codon used most frequently in E. coli genes following the initiation triplet and which may have a strong effect on gene expression by exposing the important translation elements (SD and AUG) resulted in no improvement of Bca UvrA expression. Another important factor, affecting the translation efficiency, is codon usage. Comparison of codon usage between Bca uvrA gene and the whole E. coli genome showed the biggest difference in frequence of codons for glutamine: GAA 43% (69% in Eco) and GAG 57% (31% in Eco). In contrast, all Eco rare codons are present in Bca uvrA gene with similar frequency. The substitution of the first 23 codons of Bca uvra gene led only to a slight enhancement of Bca UvrA expression.

UvrABC Incision Assay

Eco or Bca UvrA (10 nM each) was preincubated at 65° C. for 0, 10, 30, or 60 minutes, and Eco UvrB (100 nM), Eco UvrC (5 nM), and the 5'-terminally labeled benzo[a]pyrene diol epoxide, 7,8-dihydroxy-9,10-poxy-7,8,9,10-tetraydrobenzo[a]pyrene (BPDE) substrate (1 nM) were incubated in a 20 µl reaction buffer containing 50 mM Tris HCl, pH 7.5, 50 mM KCl, 10 mM MgCl$_2$, 5 mM DTT, and 1 mM ATP at 37° C. for 20 minutes. The reaction was terminated by adding EDTA (20 nM) and heating to 90° C. for 3 minutes. The samples were denatured with formamide (50% v/v) and heated to 90° C. and then quick-chilled on ice. The digestion products were loaded onto a 12% (w/v) polyacrylamide sequencing gel under denaturating conditions with TBE buffer. The gel was dried and autoradiographed using KODAK XAR5 X-ray film exposed to the gel overnight in the presence of intensifying screens at −80° C. Bca UvrA, and Bca UvrA Eco UvrB Binding Reactions and Gel Mobility Shift Assay.

DNA substrates containing site-specific cis(+)- or trans (+)-BPDE in a 50 basepair (bp) duplex were constructed as described previously (Zou et al., Biochemistry 34, 13582–1359311 (1995)). Binding reactions (20 ml) were performed with 2 nM DNA substrate (3'- or 5'-[$^{32}$P] labeled cis(+)- or trans(+)-BPDE containing 50-mer duplex) with either increasing concentrations of Bca UvrA protein (0-300 nM), or with constant Bca UvrA (10 nM) and Eco UvrB (100 nM), in binding buffer containing 50 mM Tris.Cl, pH 7.50; 10 mM MgCl$_2$; 50 mM KCl; 1 mM ATP, and 5 mM DTT for 20 minutes at 37° C. Glycerol was then added to the reaction (8% v/v) and the reaction mixture was loaded onto a 4% native polyacrylamide gel (acryl:bis at 80:1). The gel and TBE running buffer (89 mM Tris, 89 mM boric acid, 2 mM EDTA) contained 1 mM ATP and 10 mM MgCl$_2$. The reaction mixture was electrophoresed for 2.5 hours at a constant voltage (100 V) at room temperature. The gel was dried and autoradiographed using KODAK XAR5 X-ray film exposed to the gel overnight in the presence of intensifying screens at −80° C.

Quantification of Shifted Complexes and Incision Products.

All quantitative data of radioactivity were generated using Molecular Dynamics PhosphorImager 425 (Amersham Biosciences, Sunnyvale, Calif.), and Molecular Dynamics ImageQuant software (Amersham Biosciences, Sunnyvale, Calif.) using volume integration method. The amount of DNA present in shifted bands or incised products (D, in pmol) by UvrABC was calculated based on the total molar amounts of DNA used in each reaction (M) and the percentage of radioactivity in the shifted or incision products (P) as compared to the total radioactivity in both the 50-mer and shifted/incision products using the formula $D_{tota}=[P/(50mer+P)]M$.

Standard ATPase Assay.

The ATPase activities of B. caldotenax and E. coli UvrA were measured using a coupled assay in which the hydrolysis of ATP to ADP was linked to the oxidation of NADH. The standard ATPase assay mixture consisted of 50 mM Tris-Cl, pH 7.5, 100 mM KCl, 10 mM $MgSO_4$, 1 mM DTT, 10% glycerol, 2 mM phosphoenol pyruvate, 0.15 mM NADH, pyruvate kinase (20 units/ml), lactate dehydrogenase (20 units/ml) and 0.1 µM UvrA. Experiments were performed in a temperature controlled Pharmacia Ultraspec III using polystyrene micro cuvettes. The assay mixtures (0.5 ml) were allowed to equilibrate to 37° C. and reactions were initiated by the addition of ATP (1 mM). The rate of ATP hydrolysis was calculated from the slope of the linear decrease in absorbance at 340 nm that results from the oxidation of $NADH(\epsilon_M^{340}=6220)$.

Thermostability of ATPase Activities of Bca and Eco UvrA

A 50 µl mixture containing 50 mM Tris-Cl, pH 7.5, 100 mM KCl, 10% glycerol and 1 µM Bca or Eco UvrA was incubated at 65° C. for 20 minutes. Following heat treatment, the entire 50 µL mixture was added to 450 µL standard ATPase assay mixture and the ATPase activity was measured as described above.

Effect of DNA on the ATPase Activities of Bca and Eco UvrA

ATPase assays were carried out under standard conditions as described above, however, pGL-2 plasmid DNA was added in one µl-aliquots to the assay mixture and allowed to incubate in the presence of UvrA for 5 minutes prior to the addition ATP. The concentration of plasmid DNA for experiments with Bca UvrA and Eco UvrA were 5.6 nM and 0.224 nM, respectively. These concentrations were empirically chosen to give maximal effect on the enzyme activity.

Characterization of the ATPase Activity of the Bca UvrA Protein.

E. coli UvrA protein ($M_w$=103,874) has two functional ATP binding domains (Husain et al., J. Biol. Chem. 261, 4895–4901 (1986)), with the Walker-type consensus recognition sequence G-$X_4$-GK(T/S)-$X_6$-(I/Y) (SEQ ID NO:40), commonly found in ATPases (Walker et al., EMBO J. 1, 945–951 (1982); see FIG. 4). The ATPase activity of Eco UvrA is DNA independent (Seeberg and Steinum, Proc. Natl. Acad. Sci. USA 79:988–992 (1982)). However, it can be modulated by DNA as well as by UvrB (Oh et al., Nuclei Acids Res. 17, 4145–4159 (1989); and Thomas et al., J. Biol. Chem. 260, 9875–9883 (1985)).

It has been demonstrated that both ATP binding sites are essential for the action of UvrABC (Thiagalingam and Grossman, J. Biol. Chem. 266, 11395–11403 (1991); Brandsma et al., J Bacteriol. 170, 1012–1114 (1988); and Myles et al., Biochemistry 30, 3824–3834 (1991)). ATP binding at both sites promotes nucleoprotein formation and ATP hydrolysis in the C-terminal ATP binding site is thought to be necessary for the dissociation of the UvrA protein from $UvrA_2B$-DNA complex (Thiagalingam and Grossman, J. Biol. Chem. 266, 11395–11403 (1991)). It has been suggested that UvrA dimerization forms a high affinity ATP binding site (Myles et al., Chem. Res. Toxicol. 2, 197–226 (1989)) and there is also some evidence for cooperativity between the two ATP binding sites (Oh and Grossman, J. Biol. Chem. 264, 1336–1343 (1989)). Alignment of amino acid sequences between UvrA proteins from E. coli and B. caldotenax has shown a high level of identity of ATP binding sites between each other and to the consensus sequence, with the exception that while most ATPases contain a Walker A box, GKT, the homologous amino acid residues of all known UvrA proteins are GKS. See FIG. 4.

The ATPase activity of Bca UvrA protein was examined by an in vitro ATPase assay at standard assay conditions of 37° C. for comparison with E. coli UvrA, as well as at 65° C. (the physiological temperature of B. caldotenax). The results are summarized in Table 3. These data indicate that under the standard assay conditions Eco UvrA has a 16 fold greater ATPase activity than Bca UvrA. While preliminary results indicate that this difference, in part, is due to differences in $K_m$, these measurements are not intended as a quantitative assessment of the catalytic efficiencies of the two enzymes for the standard assay condition used is not optimal for each enzyme. Rather the control values for each enzyme are more useful as reference points for the effects various treatments have on their ATPase activities. Indeed, after pretreatment of Bca UvrA at 65° C. for 20 minutes approximately 40% of its ATPase activity remains whereas Eco UvrA ATPase activity has been completely eliminated. This dramatic result clearly demonstrates that Bca UvrA retains thermostable ATPase activity. These results are consistent with the observation that B. caldotenax is a thermophile with optimal growth at 65° C.

TABLE 3

| | ATPase assay | | | |
|---|---|---|---|---|
| | Rate[a] | | dsDNA[d] | |
| UvrA | Control[b] | 65° C.[c] | 0.224 nM | 5.6 nM |
| B. caldotenax | 4.42 +/− 0.21[g] | 1.92 +/− 0.16[g] | 18.4 | 45.6 +/− 1.8[f] |
| E. coli | 71.5 +/− 3.3[h] | <0.01[e,f] | 55.4 +/− 2.8[f] | N.D.[i] |

[a]Rate expressed as µM product/min./µM UvrA at 1 mM ATP and 37° C.
[b]ATPase assay performed under standard conditions as described.
[c]ATPase activity of UvrA after pre-incubation at 65° C. for 20 min.
[d]ATPase assay performed in the presence of pGL-2 control plasmid at 5.6 nM for Bca UvrA or 0.224 nM for Bca UvrA.
[e]Detection limit = 0.01.
[f]n = 3; X +/− 95% confidence limits.
[g]n = 4; X +/− 95% confidence limits.
[h]n = 5; X +/− 95% confidence limits.
[i]Not determined as concentrations ≧ 0.224 were inhibitory Although UvrA is a DNA independent ATPase, its interaction with DNA can effect its ATPase activity (Seeberg and Steinum, Proc. Natl. Acad. Sci. U. S. A. 79, 988–992 (1982); Oh et al., Nuclei Acids Res. 17, 4145–4159 (1989); and Thomas et al., J. Biol. Chem. 260, 9875–9883 (1985)). The interaction of Eco UvrA with double stranded DNA results in an inhibition of its ATPase activity (Thiagalingam and Grossman, J. Biol. Chem. 266, 11395–11403 (1991)) that has been reported to result from a decrease in $V_{max}$ although a concurrent decrease in $K_m$ leads to an overall increase in catalytic efficiency (Oh et al., Nuclei Acids Res. 17, 4145–4159 (1989)). As shown in Table 3, the binding of double-stranded DNA (dsDNA) at this concentration (0.224 nM) is inhibitory to Eco UvrA, causing a 23% decrease in its rate of ATP hydrolysis. However, as is evident in Table 3, the binding of dsDNA, at this concentration, stimulated Bca UvrA ATP hydrolysis by 400%. Further increases of the dsDNA concentration had a stimulatory on Bca UvrA, resulting in a 1000% increase its ATPase activity. Control experiments using apyrase demonstrated that the effect of DNA on ATPase activity was not an artifact of the assay. The concentrations of DNA used for each enzyme were chosen where it was experimentally determined to have reached its maximal effect. Thus, in addition to the opposite effect that DNA has on the two UvrA's, these data also suggest that quantitatively (in the presence of ATP) the interaction of Bca UvrA with non-damaged DNA is of a lower affinity than that Eco UvrA.

UvrABC Incision of BPDE-Adduct.

The present data indicate that the B. caldotenax uvrA gene can function in vivo to complement a E. coli UvrA mutation. Next, the ability of Bca UvrA to support a reconstituted UvrABC endonuclease activity in vitro in combination with E. coli UvrB and UvrC proteins and its relative thermostability were examined.

The DNA substrates used in the incision and in the gel mobility shift experiments were 5'- or 3'-[$^{32}$P]-terminally labeled double stranded 50-mer with center located either (+)-cis or (+)-trans BPDE-N$^2$-guanine adducts. These DNA adducts have been shown to be efficient blocks of DNA polymerases (Choi et al., Biochemistry 33, 780–787 (1994)) and effectively recognized and incised by E. coli UvrABC endonuclease, cis-BPDE intercalative displacement adducts being recognized more efficiently than the trans-minor grove binding isomers (Zou et al., Biochemistry 34, 13582–13593 (1995)).

Figure 6:
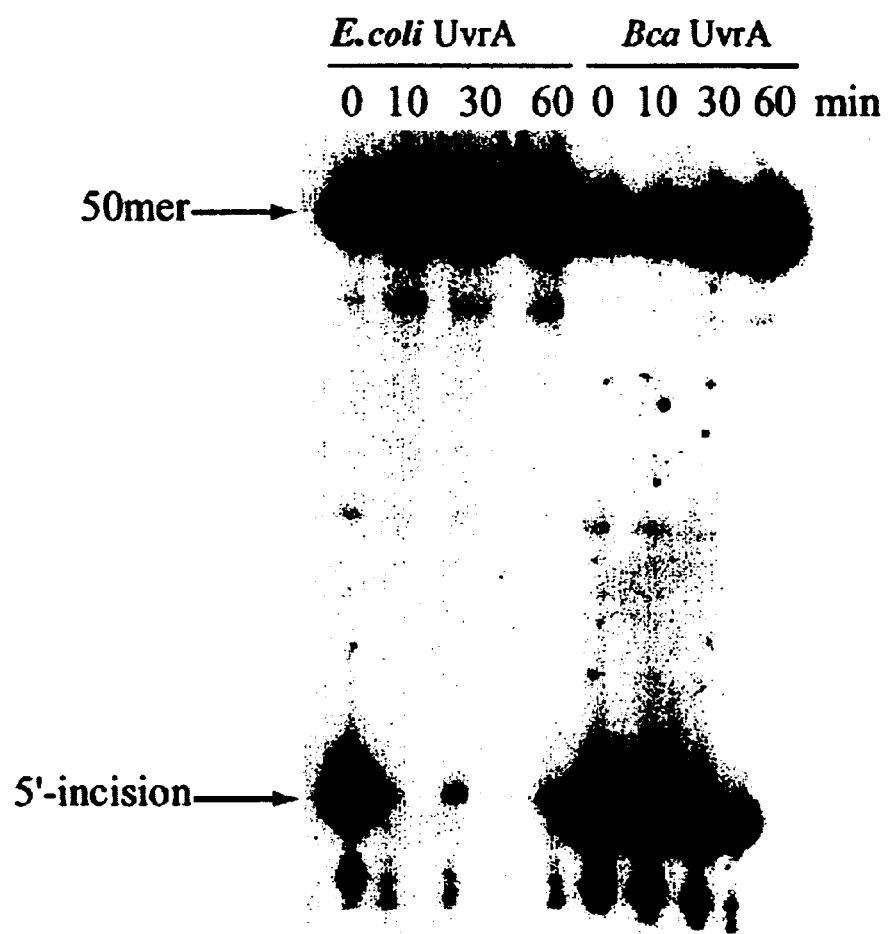
FIG. 6. Incision of 5'-end labeled (+)-cis-BPDE-damaged 50-mer duplex DNA by UvrABC endonuclease. BPDE-DNA substrate (1 nM) was incubated with Eco UvrA or Bca UvrA (10 nM each), either non-preheated or pre-incubated at 65° C. for the indicated periods, Eco UvrB (100 nM) and Eco UvrC (5 nM) in the ABC buffer at 37° C. for 20 minutes. The incised products were identified on a 12% polyacrylamide sequencing gel.

FIG. 6 shows UvrABC endonuclease incision of (+)-trans BPDE-damaged 50-bp duplex which was 5'-terminally labeled. The assay was performed with 1 nM DNA substrate, 10 nM UvrA (Eco or Bca), 100 nM UvrB (Eco), and 5 nM UvrC (Eco) in ABC buffer, as described above, and incubated at 37° C. for 20 min. UvrA proteins from Eco and Bca were either kept on ice or preincubated at 65° C. for 10, 30, or 60 min. The Eco UvrA concentration was chosen to produce the maximum rate and extent of incision as determined in an Eco UvrA titration experiment (data not shown). High concentrations of UvrA can lead to inhibition of incision (Snowden and Van Houten, J. Mol. Biol. 220, 19–33 (1991); and Bertrand-Burggraf et al., J. Mol. Biol. 219, 27–36 (1991)). Bca UvrA protein was used at the same concentration as its E. coli homologue to allow a direct comparison of both proteins in supporting UvrABC incision reaction and their thermostability. Bca UvrA protein was able to support significant higher incision (89%) than Eco UvrA (67%) (see FIG. 6 and Table 3). This result is rather unexpected when taken into consideration that E. coli is a gram-negative bacterium, while B. caldotenax is a gram-positive bacterium, and phylogenetically distant from E. coli. The result might be explained by a heat labile nature of Eco UvrA, which looses activity when stored at −20° C. for periods of time (3–6 months; see Zou et al., J. Biol. Chem. 273, 12887–12892 (1998)). Incubation of the thermolabile Eco UvrA protein for 20 minutes at 37° C. destroys its activity, in contrast to thermophilic UvrA protein from B. caldotenax which maintains full activity. As shown in FIG. 6, pre-incubating Eco UvrA at 65° C. for 10 minutes completely diminished its ability to support the incision reaction, while the same pre-incubation had only a marginal effect on Bca protein, leading to reduction of incision from 89 to 83%. Pre-incubation of Bca UvrA at 65° C. for 30 minutes results in further reduction of its activity (to 60%) (see FIG. 6). A one hour incubation leads to a substantial, approximately 4-fold reduction of Bca UvrA activity, which is surprising because 65° C. is the optimal growth temperature of B. caldotenax. Aggregation might indicate that there are some other factors, cofactors, and proteins (e.g. chaperones) which may play an important role in the thermostability of thermophilic proteins in vivo (Zou et al., J. Biol. Chem. 273, 12887–12892 (1998)). These data clearly show that the Bca UvrA protein is thermostable and efficiently supports Eco UvrB UvrC mediated incision of BPDE-containing duplex 50-mer in an in vitro assay. Thus, Bca UvrA protein can not only substitute for Eco UvrA not only in vivo, but also in in vitro conditions.

DNA Binding Activity of Bca UvrA Protein.

Figure 7A:
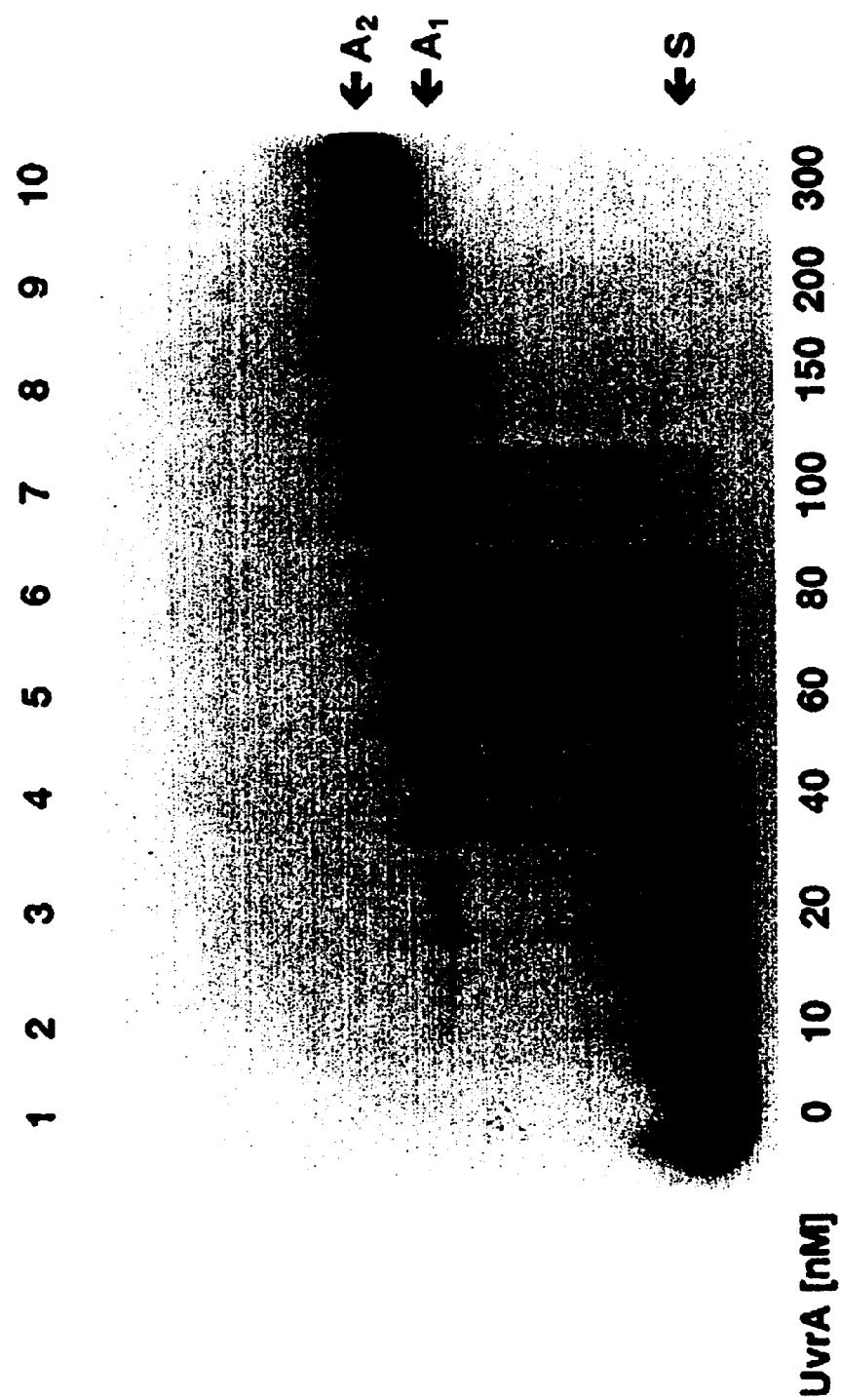
FIG. 7A is a polyacrylamide native gel of Bca UvrA-DNA shifted complexes. A$_1$ and A$_2$ represent the formation of UvrA$_2$-DNA complex. S represents non-bound substrate DNA.
Figure 7B:
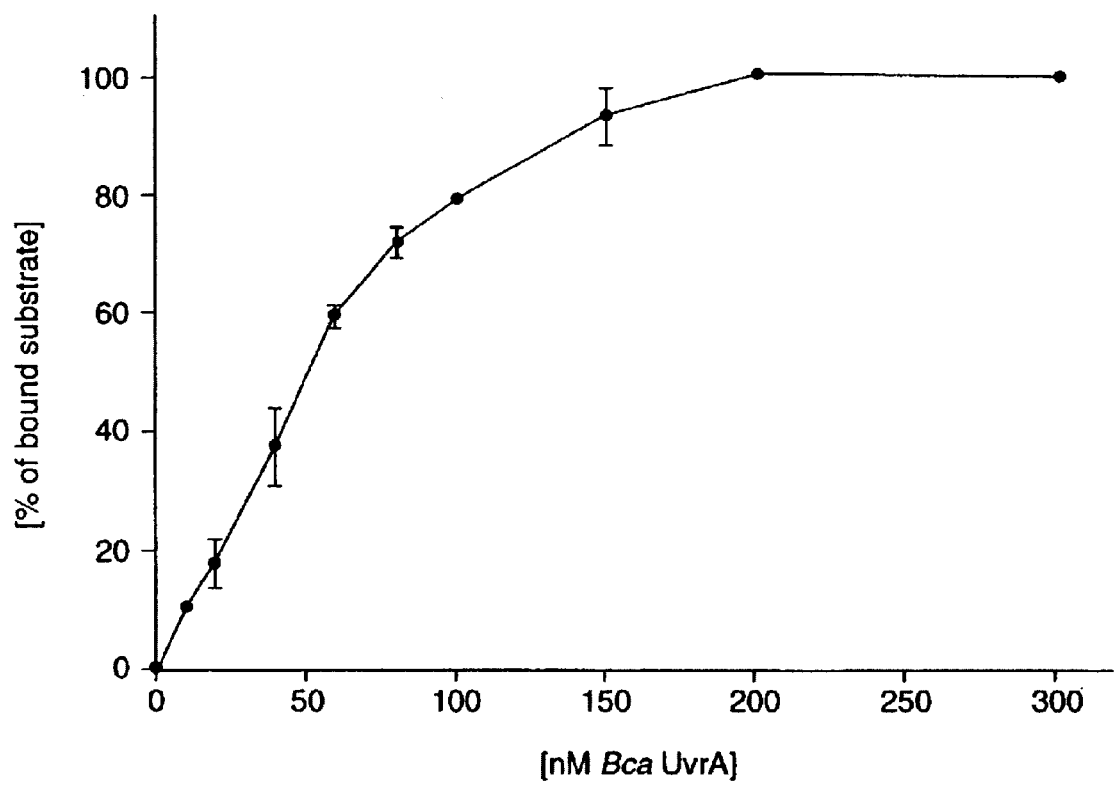
FIG. 7B is a binding isotherm of Bca UvrA$_2$ protein binding to BPDE-DNA substrate. Data were plotted as the mean of three independent experiments, in which standard deviation was 10–15%. The line represents a non-linear least square best fit of the data in which UvrA binds to DNA as a dimer as described in Zou et al., (1998) *J. Mol. Biol.* 281, 107–119.

Since Bca UvrA, in conjunction with Eco UvrB and UvrC, can support greater incision when compared to Eco UvrA, it might suggest that BPDE-containing 50-mer duplex might be recognized more efficiently by Bca UvrA than Eco UvrA. Therefore, the interaction of Bca UvrA with the above mentioned substrate DNA was examined, using a gel mobility shift assay. 5'-end labeled trans(+)-BPDE-N$^2$-dG-containing 50-mer duplex DNA (2 nM) was incubated with increasing amounts of Bca UvrA in ABC buffer at 37° C. for 20 minutes, as described above. An autoradiograph of gel mobility shift experiment, showing the interaction of Bca UvrA protein with BPDE-DNA substrate is presented in FIG. 7A. The results of three independent experiments are summarized in FIG. 7B. As shown in FIG. 7A, a single shifted band of different size was observed, dependent on the Bca UvrA protein concentration: at lower protein concentrations (10–100 nM) a shifted complex ($A_1$) is produced, which is consistent with UvrA$_2$-DNA complex (lanes 2–7), as UvrA is thought to be functional only as a dimer (Myles and Sancar, Biochemistry 30:3834–3840 (1991); and Mazur and Grossman, Biochemistry 30:4432–4443 (1991)). At higher concentrations of Bca UvrA(200 and 300 nM) a shifted complex ($A_2$) with a lower mobility is seen (lanes 9 and 10), representing presumably a higher form of oligomerization of Bca UvrA (e.g. tetramers) bound to the BPDE-DNA substrate. Using the gel mobility shift assay, the binding isotherm, shown in FIG. 7B, reveals an equilibrium dissociation constant, $K_D25 \cong 10^{-9}$ M for Bca UvrA binding to (+)-trans-BPDE-DNA substrate. This value is significantly higher than the $K_D$ of Eco UvrA(7.5 nM) for binding to the (+)-trans-BPDE-N$^2$-dG (Zou et al., J. Mol. Biol. 281:107–119 (1998)). Results of gel mobility shift assay clearly show that Bca UvrA binds less tightly to the BPDE-containing 50-mer duplex than the Eco UvrA.

Figure 8:
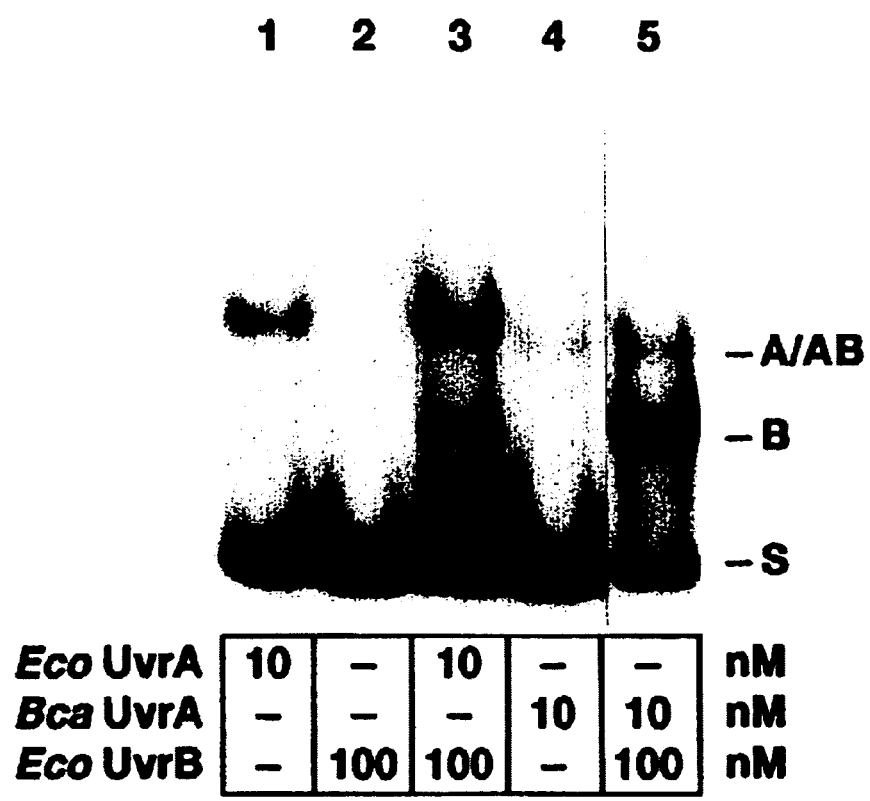
FIG. 8: Binding of BcaUvrA$_2$ EcoUvrB to the BPDE-DNA substrate. Polyacrylamide native gel of Bca UvrA$_2$-DNA and Eco UvrB-DNA shifted complexes. A/AB represents the formation of complexes of UvrA$_2$ or and UvrA$_2$UvrB with the substrate. B represents the formation of a complex of UvrB with the substrate. S represents the DNA substrate free of proteins.

These data support the theory that UvrA binding does not directly correlate to incision efficiency (Snowden and Van Houten, J. Mol. Biol. 220:19–33 (1991); and (Zou et al., J. Mol. Biol. 281:107–119 (1998)), and the formation of the stable UvrB-DNA complex may be rate-limiting for efficient incision. Therefore, the interaction of Bca UvrA with Eco UvrB protein and BPDE-DNA substrate was examined by a gel mobility shift assay. The results are shown in FIG. 8. Addition of UvrA and UvrB to the damaged substrate resulted in two shifted bands, corresponding to a UvrA$_2$B-DNA complex (A/AB) and a UvrB-DNA complex (B), respectively. Thus, the Bca UvrA protein appears to efficiently load Eco UvrB onto BPDE-DNA substrate. Eco UvrB, at a concentration of 100 nM, resulted in more than 50% of the DNA substrate bound in the form of UvrB-DNA complex, at higher concentrations of Eco UvrB (250 nM), all the BPDE-containing substrate is bound as the UvrB-DNA complex.

There have been suggested many amino acid substitutions in various proteins which might play role in their thermostability. Zulli and coworkers (Zulli et al., *Biol. Chem. Hoppe Seyler* 372:363–72 (1991)) analyzed lactate dehydrogenase (LDH) from thermophilic, mesophilic and psychrophilic bacilli and found specific amino acid substitutions particularly important for its thermostability. They have found that substitution of Thr or/and Ser by Ala residues leads to a significant increase of thermostability in mesophilic *B. megabacterium*. When Bsu and Bca UvrA were compared quantitatively in this respect, both Thr (54 to 51) and Ser (57 to 45) residues were decreased and Ala residues (59 to 65) were increased in Bca UvrA compared to Bsu UvrA. Analyzing these amino acid substitutions qualitatively, it is interesting to note that out of 17 Ala substitutions in Bca UvrA more than 50% are from either Ser (6) or Thr (3), in both cases the most frequent substitutions to Ala residue in Bca UvrA. Another striking observation is that three of these Thr(Ser)→Ala substitutions are located in 12 C-terminal amino acid residues, in the region with lowest aa sequence identity between Bsu and Bea UvrA. These changes suggest that the COOH-terminus of Bca UvrA may play an important role in its thermostability. A correlation between thermostability and increased Arg/(Arg+Lys) ratio has also been shown for several homologous enzymes (Merkler et al., *Int. J. Pept. Protein Res.* 18, 430–42 (981)). This correlation has also been confirmed for Bea UvrA; reaching an increase from 0.48 in Bsu UvrA to 0.55 in Bca UvrA.

It is also worthwhile to analyze the frequency of substitutions of another amino acid, namely proline. Proline residues have the highest β-turn potential of all the amino acids and play an important role in peptide folding and globular structure formation. They are considered to decrease the entropy of the protein in its denatured state (Watanabe et al., *Eur. J. Biochem.* 226:277–283 (1994)) and increase the conformational enthalpy in its native state (Doig and Williams, *Biochemistry* 31:9371–9375 (1992)). The increase of Pro residues has been reported in many thermophilic proteins (Yamamoto et al., *Gene* 171:103–106 (1996), Argos et al., *UCLA Forum Med. Sci.*21:159–169 (1979); Kato and Kuramitsu, *J. Biochem.* (*Tokyo*) 114:926–929 (1993); Kato et al., *J. Biol. Chem.* 271:9612–9618 (1996); Okamoto et al., *J. Biochem.* (*Tokyo*) 119:135–144 (1996); and Takamatsu et al., *Nucleic Acids Res.* 24:640–647 (1996)). It is unexpected that all 40 Pro residues from Bsu UvrA are conserved in Bea UvrA; out of 20 amino acids only three are conserved in both Bsu and Bea UvrA protein in the same location, namely Trp (1), Cys (12) and Pro (40). However, Bca UvrA contains three additional Pro residues, namely $Pro_{326}$, $Pro_{353}$, and $Pro_{403}$, suggesting that these extra proline residues might play a critical role in thermostability of Bca UvrA. Alternatively, this enhancement of Pro residues (coded by CCN) in Bea UvrA could result from a higher G+C content of Bea uvrA gene (58.8% in Bca vs 48.6% in Bsu uvrA gene, respectively). It has been suggested that an increase in the number of Pro residues, as well as deletion of residues in the loop region are common strategies for thermostability (Hiramatsu et al., *Gene* 199:77–82 (1997)). Bca UvrA protein is five amino acid residues shorter than Bsu UvrA, with two extra amino acid residues at N-terminus and three aa residues at C-terminus without any internal gaps. In contrast, UvrA protein (942 amino acids) from *Thermotoga maritima*, the most thermophilic microorganism among eubacteria, is smaller than Bca UvrA (952 amino acids), contains internal deletions of 5 and 20 amino acids, and has deleted the 16 C-terminal amino acid residues present in Bca UvrA.

Alterations of Bca UvrA Interacting with DNA and UvrB

During the studies of the present invention, two striking differences were discovered when the interaction of the Bca UvrA protein with DNA was compared to the UvrA protein from *E. coli*. First, Bca UvrA promoted more efficient loading of Eco UvrB onto damaged DNA substrate and supported higher amount of incision than its *E. coli* counterpart, although Bca UvrA bound non-damaged and damaged DNA less efficiently than Eco UvrA. Second, Bca UvrA has a DNA-stimulated ATPase activity, whereas same concentrations of dsDNA inhibited the ATPase activity of Eco UvrA. It is unexpected that a thermophilic UvrA protein, originating from a gram-positive organism is more active in both loading of UvrB and supporting incision of UvrB and UvrC from a mesophilic gram-negative bacterium. The lower activity of Eco UvrA when compared to that of Bca UvrA may be, at least partially, explained by an extreme thermolability of purified Eco UvrA. It has been suggested that UvrA protein in *E. coli* cells interacts with some stabilizing protein(s) which might be an integral part of NER in vivo and is supported by the findings that *E. coli* UvrA protein is stabilized under normal conditions by molecular chaperones, such as DnaK, DnaJ, and DnaE (Zou et al.,*J. Biol. Chem.* 273:12887–12892 (1998)). The absence of $BcaUvrA_2EcoUvrB$-DNA complexes in our gel mobility shift assays suggests a fundamentally different type of interaction between the two proteins, originating from heterologous organisms. These data suggest that Bca $UvrA_2$ protein dissociates from $UvrA_2UvrB$-DNA complex more efficiently than its *E. coli* counterpart.

Orren and Sancar (*Proc. Nail. Acad. Sci. USA* 86, 5237–5241 (1989); and *J. Biol. Chem.* 265, 15796–158036 (1990)) have proposed that $UvrA_2$ dimer dissociates from $UvrA_2B$-DNA complex once UvrB is located at the lesion site, and that the UvrA protein does not participate directly in the incision process. It has been also demonstrated that under conditions that do not favor the dissociation of UvrA from substrate the large UvrA-UvrB footprint is observed and incision is less efficient, suggesting that UvrA, after loading of UvrB onto damaged site, is not required for, and actually interferes with, incision (Snowden and Van Houten, *J. Mol. Biol.* 220, 19–33 (1991); Bertrand-Burggraf et al.,*J. Mol. Biol.* 219, 27–36 (1991)). It has been demonstrated that *E. coli* UvrA protein when stabilized by molecular chaperones, which could be viewed as an analogous situation to a thermostable UvrA protein, undergoes multiple cycles of UvrB loading that leads to an increased incision efficiency (Zou et al., *J. Biol. Chem.* 273, 12887–12892 (1998)). However, as mentioned above, heating of Bca UvrA at 65° C. for one hour leads to a loss of 86% of its activity.

More recent studies have shown that both steps, the release of $UvrA_2$, as well as the isomerization step (leading from a stable, incision-incompetent UvrB-DNA complex to an unstable, but incision-competent UvrB-DNA' complex) contribute to modulate NER efficiency (Delagoutte et al.,*J. Mol. Biol.* 266, 703–10 (1997)). The present invention indicates that the amount of the stable UvrB-DNA complex formed is directly proportional to the incision efficiency. These results are in contrast to the report by Delagoutte, showing that the efficiency of the incision reaction is inversely related to the stability of the UvrB-DNA preincision complex (Delagoutte et al., *J. Mol. Biol.* 266, 703–10 (1997)).

DNA-induced alterations in Bca UvrA ATPase activity and gel mobility shift experiments indicate that Bca UvrA binds non-damaged and damaged DNA less efficiently than the *E. coli* UvrA. Thus, the decreased affinity for DNA might also help dissociate the Bca UvrA from the UvrA$_2$ (*E. coli*) UvrB-DNA complex. The high level of in vitro complementation between Bca UvrA and Eco UvrB and UvrC, the fundamental differences in the Bca UvrA ATPase, DNA binding and UvrB loading suggest that the *E. coli* UvrA protein may exist in a pathologically unstable state due to its thermolability.

Example 2

Cloning and Expression of the *B. caldotenax* uvrB Gene

During sequencing of approximately 4.4 kb *B. caldotenax* genomic DNA fragment containing the Bca uvrA gene and conferring the UV$^R$ 4NQO$^R$ phenotype of the *E. coli* UNC1158 (UvrA$^-$) host cells described in Example 1 it was discovered that the insert also contained 370 base pairs of the 3' terminus of the uvrB gene. This finding suggested that *B. caldotenax* might have an organization of uvrA and uvrB genes similar to that of *B. subtilis* in which both genes constitute a single operon with the uvrB gene located upstream and with only an 8 bp-gap separating the two genes.

Figure 9:
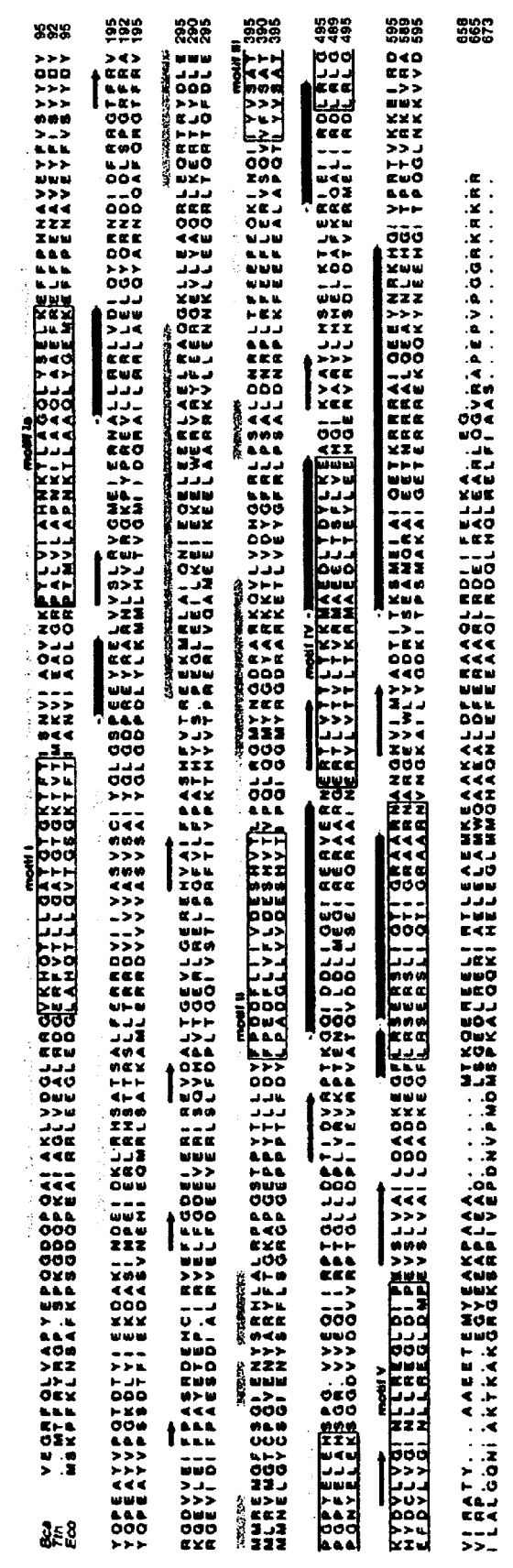

Utilizing the sequence of an adjacent gene (Bca uvrA), the inverse PCR technique was employed for the cloning of Bca uvrB gene. Inverse PCR allows in vitro amplification of a DNA flanking a region of known sequence (Ochman et al., (1988) *Genetics* 120, 621–3; Silver and Keerikatte (1989) *J. Virol.* 63, 1924–8; Triglia et al., (1988) *Nucleic Acids Res* 16, 8186). *B. caldotenax* genomic DNA was digested with BamHI restriction endonuclease, extracted with phenol and chloroform and precipitated with ethanol. Linearized DNA was circularized using T$_4$ DNA ligase and this ligation mixture was used as template DNA for inverse PCR. Two Bca UvrA gene specific primers, CGCAATATTACCCG-CAGCTGCTCG3 (SEQ ID NO:24) and CCCTTCAATCG-CATCGACGTCC (SEQ ID NO:25), used for Bca uvrA gene sequencing and oriented in opposite directions to those normally employed for PCR, were chosen as PCR primers. DNA polymerase cloned from *T. thermophilus* which allows amplification of DNA targets larger than 5 kb and which also contains a 3'→5' exonuclease (proofreading) activity was used under cycling conditions for extra-large PCR, namely 1 cycle: 94° C. for 1 minute, 16 cycles: 94° C. 15 seconds, 68° C. 10 minutes, 12 cycles: 94° C. 15 seconds, 68° C. 10 minutes with a 15-second extension in each following cycle, 1 cycle: 72° C. 10 minutes. The resulting PCR product, a fragment of approximately 15 kb which carried the complete uvrB gene, was digested with BamHI and HindIII restriction endonucleases. The 5' overhanging end of the fragment were filled in with Pfu DNA polymerase and subcloned into pUC18 vector. Using sense and antisense Bca uvrB specific primers designed from the 3'terminus of the gene, a 7-kb fragment was identified as containing the Bca uvrB gene sequence. The entire Bca uvrB gene was sequenced in the direction from its 3' terminus towards its 5' terminus. The nucleotide sequence encoding the Bca UvrB protein (SEQ ID NO:3) and the deduced amino acid sequence of the Bca UvrB protein (SEQ ID NO:4) are shown in FIG. 2. This sequence information was used to design primers for the cloning of the Bca uvrB gene into the expression vector pTYB1 of the T7 IMPACT system. FIG. 9 shoes an alignment of the UvrB sequences from *B. caldotenax*, *Thermus thermophilus* and *E. coli*. The sequence identity between UvrB from *B. caldotenax* and *E. coli* (*T. thermophilus*) is 59% (60%).

The 5' end sequence of Bca uvrB gene and its alignment with that of *E. coli* and *B. subtilus* suggested a GTG triplet coding for a valine residue as an initiation codon of Bca uvrB gene. Since expression of a target gene in the pTYB I vector requires that an ATG triplet coding for a methionine be the start codon, two different mutagenized constructs of the 5' end of Bca uvrB gene were produced, using the site-directed mutagenesis methods discussed in Example 1. The first construct, called uvrB$_{MV}$, contained an additional ATG codon upstream of the GTG codon. In the second construct, called uvrB$_{ME}$, the GTG codon was replaced with an ATG codon.

For each construct, the primers used for amplification of Bca uvrB gene were as follows: a MV sense primer CTC-CTATCATATGGTGGAGGGCCGTTTTCAATTAGT (SEQ ID NO:26), a ME sense primer TACACTCCATATG-GAGGGCCGTTTTCAATTAGTGG (SEQ ID NO:27), and a 3' antisense primer GTACAGTGCTCTTCCGCACCCT-TCCGCTTTCAATTCGAA (SEQ ID NO:28). The Bca uvrB gene was amplified by PCR in a 100 µl-reaction mixture containing 2.5 mM MgCl$_2$, 200 µM dNTP's, 20 pmol each primer, 100 ng Bca genomic DNA and 2.5 U Pfu DNA polymerase using following conditions: 1 cycle: 94° C. 2 minutes; 25 cycles: 94° C. 45 seconds, 55° C. 45 seconds, 72° C. 4 minutes, followed by 72° C. 10 minutes. The resulting PCR products were purified using a Wizard PCR DNA purification kit (Promega, Madison, Wis.), digested with NdeI and SapI restriction endonucleases and cloned into pTYB1 vector, respectively. Both versions of Bca uvrB gene were sequenced and except for the first four nucleotides they did not differ in their sequence.

In order to achieve high expression and rapid purification of the Bca UvrB protein in *E coli*, the uvrB gene of *B. caldotenax* was subcloned into pTYB1 vector of T7 IMPACT System (NEB). This expression system, discussed in more detail in Example 1, is based on an in-frame three part fusion between the target gene (Bca uvrB), an intein (from *S. cerevisiae*), and chitin binding domain (CBD; from *Bacillus circulans*).

The resulting plasmids pTYB1 uvrB$_{MV}$ and pTYB1 uvrB$_{ME}$ were transformed into appropriate *E. coli* host cells, respectively and the induction of the fusion protein in the cells was monitored by PAGE. The highest overexpression was achieved by *E. coli* BL21 (DE3)/pTYB1uvrB$_{MV}$ which was used for a large-scale isolation (from 9-liter culture). The IPTG induction of Bca UvrB was performed at 30° C. for 3 hours with shaking (250 rpm). The induced culture was centrifuged and cell pellets were stored at –20° C.

The UvrB protein was purified following the T7 IMPACT system manual (New England Biolabs). Cell extracts were prepared by resuspending the cells in 1/50 volume of column/wash buffer (20 mM Tris-HCl pH 8.0, 500 mM NaCl, 0.1 mM EDTA, 0.5% Triton X-100) containing 5 µg/ml leupeptin and 10 µg/ml pepstatin followed by sonication. Cell debris was removed by centrifugation and the supernatant was loaded onto a chitin column. The column was washed with at least 30 vols of column/wash buffer. The on-column cleavage of the fusion protein (UvrB-intein-CBD) was initiated by flushing the column quickly with two column volumes of freshly prepared cleavage buffer (20 mM Tris-HCl p1H 8.0, 500 mM NaCl, 0.1 mM EDTA, 30 mM DTT). A third column volume of cleavage buffer was added and cleavage was continued at 4° C. overnight. UvrB (>98% pure) was eluted in three column volumes using additional cleavage buffer (without DTT). The appropriate fractions were pooled and dialyzed against storage buffer (50 mM Tris-HCl pH 7.5, 100 mM KCl, 0.1 mM EDTA, 50% glycerol) and concentrated to 1 mg/ml. The average yield was approximately 2 mg of purified protein per liter.

Example 3

Crystal Structure of UvrB

As a first step in understanding the structural details of NER, the three-dimensional structure of UvrB from the thermophilic organism *Bacillus caldotenax* at 2.6 Å resolution has been determined (Theis et al., *EMBO J.* 18, 6899–6907 (1999)). These results indicate that UvrB can be divided into four domains, termed 1a, 1b, 2 and 3, with the ATP binding site being located between domains 1a and 3. Two of the domains of UvrB (1a and 3) are structurally related to helicases belonging to superfamilies I and II, and all residues implicated in coupling ATP hydrolysis to strand translocation in these helicases are present in UvrB as well. The UvrB structure is thus evidence that UvrB functions as a helicase adapted to the unique requirements of DNA repair. One of these requirements is the ability to form a tight pre-incision complex with damaged DNA. Based on the crystal structure we propose that in the pre-incision complex UvrB uses a padlock-like binding mode to wrap around one DNA strand by inserting a β-hairpin between the two strands of DNA.

Crystallization and Structure Determination

UvrB crystals were grown by hanging drop vapor diffusion. Equal volumes of a solution containing 8 mg/ml UvrB in 500 mM NaCl, 20 mM Tris-HCl pH 8.2, 1 mM DTT, 0.1 mM EDTA, 0.03% dodecylmaltoside were mixed with a precipitant solution containing 14–18% PEG 6000 or PEG 20 000, 10 mM ZnCl2 and 100 mM Bicine at pH 9 and equilibrated against a reservoir solution containing 20% PEG 6000, 500 mM NaCl, 100 mM Tris-HCl pH 8.5. Diffraction data of crystals, cryocooled in liquid nitrogen, were collected at beamlines X26C and X25 at the National Synchrotron Light Source in Brookhaven. The crystals belong to space group P3121 with a=b=150.4 Å, c=79.5 Å and contain one molecule per asymmetric unit. The structure of UvrB was solved by MIR. Derivatives were prepared by soaking crystals in solutions containing 500 mM NaCl, 14–18% PEG 6000 or PEG 20 000, 10 mM ZnCl2, 100 mM Bicine pH 9 and 1–2 mM with the following heavy atom compounds for 24 hours; K[Au(CN$_2$)], trimethylleadacetate, sodium ethylmercurythiosalicylate, and di-$\mu$-iodo-bis-(ethylenediamine) di-platinum II nitrate. All data were indexed, integrated and scaled with the HKL software (Otwinowski and Minor (1997) *Methods Enzymol.*, 276, 307–326). With exceptions as indicated, the CCP4 suite was used for all further crystallographic computations (Bailey (1994) *Acta Crystallogr. D*, 50, 760–763). The gold derivative was solved by Patterson methods and direct methods using SHELX (Sheldrick (1990) *Acta Crystallogr. A*, 46, 467–473). All other derivatives were solved by difference Fourier calculations. The ambiguity of enantiomorphic space groups and heavy atom handedness was resolved using the anomalous signal of the PIP derivative.

Phase refinement was performed with SHARP (De La Fortelle and Bricogne (1997) *Methods Enzymol.*, 276, 472–494) to a resolution of 3.0 Å. Only the gold derivative provided experimental phases up to 3.0 Å resolution, but due to the high solvent content of 68% the quality of the maps was greatly improved after solvent flattening with SOLOMON (Abrahams and Leslie (1996) ATPase. *Acta Crystallogr. D*, 52, 30–42). The resulting electron density map was of sufficient quality to trace all domains with the exception of domain 2, and to assign side chains with the program O (Jones et al. (1991) *Acta Crysiallogr. A*, 47, 110–119). This assignment was checked against the results of the secondary structure prediction program PHD (Rost and Sander (1993) *J. Mol. Biol.*, 232, 584–599) and the known location of the ATP binding motif. The preliminary model was subjected to torsion angle dynamics refinement with X-PLOR (Brünger (1992) X-PLOR Version 3.1A System for X-ray Crystallography and NMR. Yale University Press, New Haven, Conn.) at 2.9 Å resolution).

Because the electron density in the region of domain 2 remained unclear even after combination of MIR and model phases, we performed multi-crystal averaging between the native and the Au derivative data set. This derivative showed differences in cell constants (0.7% in a and b) and high non-isomorphism to the native data set. A refinement of the model against the derivative data showed that the non-isomorphism was caused by small domain movements. The density modification clearly improved the quality of the map in those regions, and it was possible to trace domain 2. The side chain density of residues 189–223 was weak and this part of UvrB has been modeled as poly-alanine.

Refinement against the 2.6 Å resolution data set was performed using a combination of the programs X-PLOR and REFMAC (Murshudov et al. (1997) *Acta Crystallogr. D*, 53, 240–255). All data (no σ-cutoff) between 20 and 2.6 Å resolution were included in the refinement, and partial structure factors for the bulk solvent contribution were calculated in X-PLOR. The model contains residues 2–186, 189–223 and 225–595, two zinc ions and 83 water molecules. The average B-factor of all atoms is 70 Å2, comparable to the Wilson B-factor of 68 Å2. The C-terminal residues 596–658 were not visible in the electron density and are thus missing in the model. A mass spectrum of the protein sample and SDS gel electrophoresis of dissolved crystals indicated that the protein is expressed with full length and stays intact in the crystal.

The UvrB-ATP complex was prepared by soaking crystals in a solution containing 5 mM ATP, 5 mM MgCl2, 500 mM NaCl, 16% PEG 6000, 10 mM ZnCl2, 100 mM Bicine pH 9 for 24 hours. A difference Fourier map showed clear electron density for an ATP molecule and a Mg2+ ion. The coordinates from the apo structure were subjected to rigid body refinement and torsion angle dynamics refinement against the UvrB-ATP diffraction data. The ATP and the Mg2+ ion were then included in the model, which was refined with REFMAC and X-PLOR as described for the apo form.

The β-fold of UvrB

As discussed in Example 2, above, the nucleotide sequence encoding UvrB (SEQ ID NO:3) from the thermophilic organism *B. caldotenax* has been cloned and a polypeptide expressed (SEQ ID NO:4). The protein shares high sequence similarity with the *E. coli* protein (FIG. 9A) and is able to substitute for it in an in vitro excision assay. The structure of UvrB was solved by multiple isomorphous replacement (MIR) with four heavy atom derivatives (K[Au(CN$_2$)], trimethylleadacetate, sodium ethylmercurythiosalicylate, and di-$\mu$-iodo-bis-(ethylenediamine) di-patinum II nitrate) and subsequent solvent flattening. The current crystallographic model consists of residues 2–186, 189–223 and 225–595. Thirty-five residues in domain 2 were modeled as alanines due to lack of side chain density, and the C-terminal 63 residues are missing from the model due to disorder. The R-factor (free R-factor) at the current stage of refinement is 25.6% (32.4%).

The structure consists of four domains named 1a, 1b, 2 and 3. Surrounded by domains 1b, 2 and 3, domain 1a is located at the center of the molecule and folds as an α/β/α-sandwich. The central β-sheet contains seven parallel strands, in the order 7, 1, 6, 5, 2, 4, 3. Helicase motif I (the ATP binding motif) is located at the C-terminal end of strand 1, and motifs II and III are at the C-terminal ends of strands 5 and 6, respectively. Domain 2 (residues 151–251) contains two anti-parallel β-sheets of four and two strands, respectively, which form a β/β-sandwich. According to sequence similarity, the TRCF (mfd protein) contains a similar domain. Domain 2 and one part of domain 1b (residues 252–323) are inserted between strands 4 and 5 of the central β-sheet. The other part of domain 1b (residues 347–378) is inserted between strands 5 and 6 of the central β-sheet; both sequence stretches are mainly α-helical. Domains 1a and 1b form a large cleft that is bridged by a β-hairpin (residues 90-115) inserted between strand 3 and an α-helix of domain 1a. Similarly to domain 1a, domain 3 (residues 412–595) folds into an α/β/α-sandwich. The parallel β-sheet contains six strands in the order 1, 6, 5, 2, 3, 4, connected by helices or loops on both sides of the sheet. Helicase motifs IV, V and VI are located in this domain, at β-strand 2, β-strand 4 and at the C-terminal end of the helix connecting strands 5 and 6, respectively. A large α-helix and a loop wrap around the domain such that the C-terminus of the model is located close to domain 1a.

UvrB binds specifically to ATP or dATP, and ATP hydrolysis is a requirement for NER (Oh and Grossman (1987) *Proc. Natl Acad. Sci. USA*, 84, 3638–3642). Mutation of Lys45 in the ATP binding motif (helicase motif I) of UvrB results in failure to form the pre-incision complex between UvrB and the damaged DNA (Seeley and Grossman (1989) *Proc. Natl. Acad. Sci. USA*, 86, 6577). To study the structural basis for this ATPase requirement, UvrB crystals were soaked in Mg-ATP-containing solutions and the structure of the resulting complexes was determined. The cofactor was clearly visible in the difference electron density map, including its triphosphate group. An additional difference density peak close to the- and -phosphates was interpreted as a Mg2+ ion. Apparently, the UvrB crystals have not hydrolyzed the ATP during the 24 hours of soaking. This is not surprising because full ATPase activity of UvrB requires the presence of both UvrA and DNA (Caron and Grossman (1988) *Nucleic Acids Res.*, 16, 9651–9662). In addition, if ATP hydrolysis in UvrB were associated with domain movements as observed for related helicases (Kim et al. (1998) *Structure*, 6, 89–100; Velankar et al. (1999) *Cell*, 97, 75–84), residual hydrolytic activity would be further inhibited by crystal packing constraints, which prevent these movements.

The ATP molecule is bound to UvrB at the adenine and phosphate moieties. N6 and N7 of the adenine form hydrogen bonds to the side chain of the conserved Gln17 and the carbonyl oxygen of Glu12. The observed pattern of hydrogen bond donors and acceptors explains the specificity for adenine. The hydrophobic residues Pro414 and Tyr11 on either face of the base position N6 and N7 for hydrogen bonding. The phosphate moiety is mainly bound by hydrogen bonds donated from backbone nitrogens of helicase motif I residues Thr41, Gly42, Thr43 and Lys45. Side chains of the conserved residues Glu338 and Asp339 of helicase motif II point toward the Mg2+ ion, but are too distant for direct interactions.

Random mutagenesis of UvrB from *E. coli* has demonstrated the importance of not only motif 1, but also motifs V and VI for DNA repair (Moolenaar et al. (1994) *J. Mol. Biol.*, 240, 294–307). For example, the mutant R544H is deficient in DNA repair, shows no helicase activity and its ATPase activity is not activated by DNA in the presence of UvrA. The crystal structure reveals that Arg543 (corresponding to Arg544 in *E. coli*) is located in domain 3 at the interface to domain 1, close to the β- and γ-phosphates of ATP. With the ATP conformation and the domain orientation observed in the crystal, however, Arg543 and also the conserved charged residues Arg540 and Glu510 are too distant from the ATP molecule for direct interactions. The interface between domains 1a and 3 is highly conserved, with most of the helicase motifs and additional conserved residues unique to UvrB located in this region.

The structural differences between UvrB in the apo and cofactor-bound forms are small, with root mean square (r.m.s.) differences between corresponding C positions in the two structures of 0.55 Å. Substantial local differences are observed in the backbone around residue Thr41. To make room for the γ-phosphate of ATP, the side chain of Thr41 is displaced; the distance between corresponding C and C atoms after superimposing domains 1a of the two structures is 1.7 and 1.1 Å, respectively. A small (2.3°) rotation of domain 3 relative to domain 1a is observed. Calculations of the electrostatic potential show that the interacting surfaces of domains 1a and 3 have opposite charges. Cycling between apo, ATP- and ADP-bound forms will modulate the electrostatic interactions, which might contribute to domain motions.

The role of the helicase motifs in Mg-ATP binding and ATPase activity has been studied in detail for the helicase PcrA (Soultanas et al. (1999) *J. Mol. Biol.*, 290, 137–148). Structural comparisons of the ATPase site of PcrA in the presence and absence of DNA substrate and cofactor analogs showed that in addition to inter-domain movements, intra-domain movements and changes in side chain conformations are observed. Significantly, the conformation of the cofactor analog was different in the presence and absence of a DNA substrate. The structure of UvrB in complex with ATP clearly shows why the nucleotide can not be hydrolyzed, but it can only suggest which residues are involved in Mg-ATP binding and hydrolysis in the active complex with UvrA and DNA.

Structural Similarity to Helicases

Known protein structures were searched for similarity to UvrB using the program Dali (Holm and Sander (1995) *Trends Biochem. Sci.*, 20, 478–480). The two proteins with highest similarity (Z-scores of 14.8 and 8.8) are the helicases NS3 (Protein Data Bank code 1HEI) and PcrA (Protein Data Bank code 1PJR), which share two structurally related domains with UvrB (Kim et al. (1998) *Structure*, 6, 89–100; Velankar et al. (1999) *Cell*, 97, 75–84). Domains 1a and 3 in UvrB correspond to domains 1 and 3 in NS3 and domains 1A and 2A in PcrA. Interestingly, no structural similarities to domain 1b or 2 of UvrB were detected, and no similarities of UvrB to nucleases were found.

The structural similarity of UvrB to helicases is greater than predicted from sequence alignments, which detect homologies in the helicase motifs only. PcrA and NS3 both show domain motion driven by ATP hydrolysis. From the high structural similarity of domains 1 a and 3 to helicases, and the high sequence conservation of the domain interface, one can conclude that UvrB undergoes domain motions driven by ATP hydrolysis in the presence of UvrA and DNA. The helicase activity of NS3 and PcrA is attributed to alternate binding and release of the single strand by the two moving domains (Kim et al. (1998) *Structure*, 6, 89–100; Velankar et al. (1999) *Cell*, 97, 75–84). If UvrB has a similar mechanism for its helicase-like activity, one would expect to find DNA binding sites in or near domains 1a and 3.

Location of DNA Binding Sites

The electrostatic surface potential of UvrB was calculated to locate possible DNA binding sites. While the net charge of the protein is negative and domain 1 has no extended surface area with a positive charge, the surface on domain 3 around helicase motif IV residues is charged positively and might interact with the phosphate backbone of DNA. The DNA-interacting surfaces of UvrB are expected to be conserved. Apart from the conserved residues at the ATP binding site, UvrB has two other surface patches with conserved residues. One is located in domain 3 at the possible DNA binding site, and the other at the entrance to the opening formed by the β-hairpin and residues of domains 1a and 1b. Because the latter surface patch contains no residues from the helicase motifs, it probably conveys a function that is unique to UvrB.

To analyze whether the DNA binding sites suggested for UvrB above correspond to those revealed by the structure of NS3 in complex with DNA (Kim et al. (1998) *Structure*, 6, 89–100) (Protein Data Bank code 1A1V), the two structures were superimposed. To account for domain motions, domain 3 and domain 1a of UvrB were superimposed separately. This results in a domain rotation of 17 from that observed in the crystal structure. The C-terminal end of domain 1 and the N-terminal end of domain 3 do not move far away from each other as indicated by an increase of 4.9 Å in the C distance between residues 412 and 413, demonstrating that this reorientation could be accomplished by a hinge motion.

In the superposition, domain 3 of UvrB contacts the backbone of the DNA through conserved residues in helicase motifs IV and V. In the NS3 DNA complex, hydrophobic side chains near domains 1 and 3 (Trp501 and Val432) intercalate between consecutive bases of the DNA, presumably translocating the DNA. Val432 is part of an interdomain stretch leading into domain 2, and thus has no direct counterpart in UvrB. However, there is a solvent-exposed side chain, Phe527, in close proximity that could act as an intercalator. The second DNA binding site in NS3 is located between domains 1 and 2. In the superposition with UvrB, the cleft between domains 1 and 2 of NS3 aligns with the cleft between domains 1a and 1b of UvrB, and the DNA passes underneath the β-hairpin (residues 90–115) of UvrB. The conserved Tyr146 of UvrB is in close proximity to Trp501 of NS3 and thus might also act as an intercalator. A superposition with PcrA in complex with DNA results in a similar path of DNA with respect to UvrB.

Structural comparisons and the location of charged and conserved residues thus suggest the same path for the translocated strand during UvrB helicase action. The extent of the proposed DNA binding sites in UvrB differs from that in NS3. In domain 1a/b, the proposed binding site of UvrB would surround the DNA single strand, effectively capturing it, whereas there are fewer possible interactions in domain 3 of UvrB because of the missing inter-domain stretches. However, it is likely that UvrA strengthens the UvrB-DNA interaction by binding to both UvrB and DNA.

The β-Hairpin

The tips of the β-hairpin form non-bonded contacts with residues of domain 1b. There are two salt bridges, between Glu99 and Arg367, and between Lys111 and Glu307. In addition, the side chains of Tyr101, Tyr108, Leu361 and Phe366 form a small hydrophobic core. These residues are all strictly conserved or, in the case of Tyr108, type-conserved in UvrB. Spanning the gap between the domains, residues Tyr92-Glu99 and Asp112-Asn116 are solvent exposed and have high temperature factors indicating mobility. The content of conserved hydrophobic residues in this region is unusually high and suggests that the hairpin interacts with a hydrophobic binding partner. If single-stranded DNA binds to UvrB between the β-hairpin and domain 1b as suggested above, complex formation or dissociation requires either free DNA ends or a conformational change in UvrB such that the strand can pass between the β-hairpin and domain 1b. The natural substrate for UvrA2B is damaged double-stranded DNA, which is partially unwound in the complex. Artificial substrates containing unpaired DNA bubble structures are also bound by UvrB, even in the absence of UvrA (Zou and Van Houten, 1999). In both cases, the single-stranded parts of the DNA have no free ends. The suggested binding mode would therefore lock the single strand between the β-hairpin and domain 1b of UvrB. Complex formation and dissociation would require that the β-hairpin acting as a lock is flexible and can open and close. The limited interactions of the β-hairpin with domain 1b and the lack of rigid secondary structure are consistent with this suggested mechanism of UvrB-DNA interaction.

Structural Model of the Pre-Incision Complex

UvrB is unable to bind double-stranded DNA, and binds single-stranded DNA only weakly. The pre-incision complex between UvrB and damaged double-stranded DNA formed with the help of UvrA, however, is extremely stable, even at high ionic strength (Orren and Sancar (1989) *Proc. Natl Acad. Sci. USA*, 86, 5237–5241). It was therefore suggested that in the pre-incision complex UvrB is bound to DNA by intercalation or hydrophobic interactions. On the basis of structural comparisons between UvrB and NS3, the location of conserved residues and the flexibility of the hairpin, we propose that in the pre-incision complex UvrB locks a DNA single strand in the gap between domains 1a and 1b with the β-hairpin acting as a clamp. Opening and closing of the clamp would be slow unless catalyzed by a third component like UvrA. This would explain the low affinity of UvrB for DNA and the high stability of the pre-incision complex once it has formed.

Based on the assumption that one strand of DNA is clamped by the β-hairpin of UvrB a model for the pre-incision complex between UvrB and DNA was constructed. Studies with double-stranded DNA containing mismatches indicate that UvrB binds if 3–6 bp are disrupted (Zou and Van Houten (1999) *EMBO J.*, 18, 4889–4901). As a starting model, we used coordinates of partially unwound DNA containing a cyclobutane T-T dimer as observed in the endonuclease V-DNA complex (Protein Data Bank code I VAS) (Vassylyev et al. (1995) *Cell*, 83, 773–782). However, to insert the β-hairpin between the DNA strands, the duplex had to be further unwound to open up a total of 5 basepairs. The orientation of the DNA with respect to domain 3 was modeled based on the interaction of NS3 with single-stranded DNA. The other end of the DNA was modeled pointing away from the surface of UvrB because the electrostatic potential is negative at the exit of the opening. The resulting bend in the DNA is consistent with results from electron microscopy studies, which estimate a bending angle of 130° (Shi et al. (1992) *J. Mol. Biol.*, 226, 425–432). In this model, the conformation of the β-hairpin was kept constant during the docking procedure, but due to the mobility of the hairpin in the crystal structure it seems likely that it will change its conformation upon DNA binding. This model does not indicate whether UvrB locks the damaged or the undamaged strand, and both cases will be discussed in terms of damage recognition and excision below.

Recognition of DNA Damage and Dual Incision

Recognition of the DNA lesion is accomplished by both UvrA and UvrB. The formation of the pre-incision complex proposed above requires that the DNA is unwound and the β-hairpin moves away from domain 1b for insertion between the DNA strands. Both processes require free energy, which is available either through ATP hydrolysis by UvrA$_2$B or as a result of complex formation. Two mechanisms of damage recognition leading to the proposed stable pre-incision complex of UvrB with DNA at the site of damage are possible. In the first mechanism, UvrA opens the double strand and UvrB's β-hairpin locks the damaged strand close to but not directly at the site of damage. UvrA$_2$B then translocates along the locked strand until it stalls upon encountering the lesion, thereby triggering the release of UvrA. In the second mechanism, UvrA opens the double-stranded DNA and moves the β-hairpin of UvrB away from domain 1b. The UvrA$_2$B complex translocates along the undamaged strand in this open conformation until it dissociates from the DNA after a limited time or encounters the lesion. In the latter case, UvrA would release both the DNA and the β-hairpin, which would resume interactions with domain 1b and thus lock the undamaged strand. The damage recognition in the first mechanism is indirect, recognizing all lesions that interfere with helicase activity because of size or chemical nature. In contrast, the second mechanism requires a more direct interaction of either UvrA or UvrB with the lesion not directly linked to the helicase activity.

The helicase-like activity leading to the proposed pre-incision complex will differ from the inchworm mechanism of NS3 and PcrA (Kim et al. (1998) *Structure*, 6, 89–100; Velankar et al. (1999) *Cell*, 97, 75–84) in several respects. While the latter proteins require a single strand-double strand junction as substrate, the substrate of UvrB is double-stranded DNA. In contrast to other helicases, UvrB does not separate long stretches of DNA. In this model of the pre-incision complex demonstrates that it is structurally feasible for the single-stranded DNA to re-anneal after it passes underneath the β-hairpin, allowing strand translocation without strand separation. While PcrA and NS3 each have helicase activity by themselves, UvrB's activity is present only in complex with UvrA. Owing to the lack of structural data on UvrA, it is not clear how the UvrA dimer binds to the UvrB monomer and where the DNA binding domains of UvrA are located. Biochemical data suggest that UvrA interacts with domain 2 and the disordered C-terminus of UvrB. These binding sites would position UvrA on either side of the β-hairpin such that UvrA could assist UvrB in DNA binding. After dissociation of UvrA, the double-stranded regions on both sides of the unwound DNA fix UvrB in its position without the requirement for strong binding to the single strand. Thus, the proposed pre-incision complex is kinetically trapped rather than thermodynamically stable. In contrast to double-stranded DNA, single-stranded DNA with free ends would be able to escape, in agreement with the observed low binding constants of UvrB for single-stranded DNA (Hsu et al (1995) *J. Biol. Chem.*, 270, 8319–8327).

Dual incision takes place after UvrC binds to the pre-incision complex. Biochemical data indicate that the active site for the 5' incision resides in UvrC (Lin et al. (1992) *J. Biol. Chem.*, 267, 17693–17700); the data concerning the location of the 3' incision are ambiguous (Lin et al. (1992) *J. Biol. Chem.*, 267, 17693–17700; Moolenaar et al. (1995) *J. Biol. Chem.*, 270, 30508–30515). If UvrB locks the damaged strand close to the lesion, the 3' incision would have to occur near the cleft between domains 1a and 1b, but there is no indication of a nuclease active site close to the hairpin. More importantly, the incised strand would be free to escape from its locked position without movement of the β-hairpin. In contrast, if UvrB locks the undamaged strand, it would remain bound even after dual incision. Removal of the oligonucleotide and UvrC by UvrD does not require processing of the undamaged strand; UvrB could remain locked to the undamaged strand until DNA polymerase I uses it as a template for resynthesis, displacing UvrB. Thus, a model of a pre-incision complex in which UvrB locks the undamaged strand is favored, because it is more consistent with the biochemical data on events following dual incision.

With the present invention, the crystal structure of the UvrB protein from *Bacillus caldotenax* has been solved. Additionally, the crystal structure of UvrB from *Thermus thermophilus* has also been determined, see Machius et al. (1999) Proc. Natl. Acad. Sci. USA, 96, 11717–11722. The determination of such crystal structures is a first step in understanding the structural basis of damage recognition and processing during NER. UvrB has all the structural properties of a helicase, with a unique binding site for the translocated strand. The pre-incision complex between UvrB and damaged DNA is a key intermediate in excision repair, which links damage recognition to the location of dual incision. Once this complex is formed, UvrB has to remain bound to the DNA without translocating, ensuring precise removal of the damaged fragment. It is proposed that UvrB wraps a flexible β-hairpin around the undamaged strand and thus locks the DNA in the pre-incision complex.

Example 4

Cloning and Expression of the *B. caldotenax* uvrC Gene

To clone the Bca uvrC gene, 5' end and 3' end guessomers were designed from the most conserved regions of the UvrC protein among ten different bacterial sequences publicly available on GenBank, National Center for Biotechnology Information, National Institutes of Health. The 5' end guessomer (C1s), GCGGATCCGTBATYTAYGTBG-GNAARGC (SEQ ID NO:29), was derived from the sequence VIYVGK (SEQ ID NO:30), which corresponded to amino acid residues 28–33 of the UvrC protein, with an added BamHI restriction site. The 3' end guessomer (C2as), GCGAATTCCCRTTNCCNCCRTCRAT (SEQ ID NO:31), was derived from sequence IDGGKG (SEQ ID NO:32), which corresponded to amino acid residues 452–457 of the UvrC protein, with the addition of an EcoRI restriction site. An approximately 1.3 kb fragment of the Bca uvrC gene, which represented about 71% of the entire gene, was amplified by PCR using guessomers C1s and C2as as primers and Bca genomic DNA as template. The rTth DNA polymerase was used under the following conditions: 1 cycle: 2 minute; 25 cycles: 94° C. 30 seconds, 55° C. 1 minute, 72° C. (20%) 3 minutes; 1 cycle: 72° C. 10 minutes. The resulting PCR product was digested with BamHI and EcoRI, subcloned into pUC18 vector and sequenced from both ends using pUC forward and reverse sequencing primers, respectively. The sequence information obtained was used to design internal Bca uvrC gene primers that were used for the sequencing of the entire 1.3 kb fragment of Bca uvrC gene. Some of the uvrC sequencing primers were used in combination with pUC forward and reverse primers, respectively in PCR reactions containing Bca genomic libraries (in pUC8, pUC8.1 and pUC8.2 vectors) as templates to subclone the 5' and 3' termini of Bca uvrC gene. Using this approach, the sequence of the Bca uvrC gene, except for the first 81 nucleotides at the 5'end of the gene, was determined.

To obtain the complete sequence information, the 5'end fragment of Bca uvrC gene was subcloned by inverse PCR using PstI-digested and recircularized Bca genomic DNA as template, and Bca uvrC sequencing primers CseqIIs (CATCGCACATCAGAGCTTTTGG) (SEQ ID NO:33) and CseqIIIas (TCAGCGATCTCCTCAACAAGCC) (SEQ ID NO:34) in an extra long (XL) PCR formulation using rTth DNA polymerase. The resulting ~4-kb fragment was digested with SmaI, end polished with Pfu DNA polymerase, and both fragments (2.5 kb and 1.5 kb, respectively) were subcloned into pUC 18 vector. The smaller, 1.5-kb fragment contained the 5'end of the Bca uvrC gene.

FIG. 3 shows the nucleotide sequence encoding the *B. caldotenax* (Bca) UvrC protein (SEQ ID NO:5) and the deduced amino acid sequence of the *B. caldotenax* (Bca) UvrC protein (SEQ ID NO:6).

For expression of the Bca UvrC protein, the sequences of the 5' and 3' termini of the Bca uvrC gene were used to design PCR primers for the subcloning of the uvrC gene into the N-terminal fusion vector pTYB11 as well as the C-terminal fusion vectors of the NEB IMPACT system (pTYB1, pTXB 1, and pKYB1). The highest level of overexpression of Bca UvrC protein was obtained from *E. coli* C41 (DE3)/pTXB1 uvrC transformants.

The Bca uvrC gene was subcloned into pTXBI vector by overlap PCR to remove an internal NdeI site present in the gene. PCR1 contained oligo C1, AAFTTACCCATATGAAC-GAGCGTCTGAAAGAAA AACTG (SEQ 11) NO:35) and oligo C2. GCATTGGCCCATGTGGTA ATACAAAC (SEQ ID NO:36) as primers. PCR2 contained oligo C3.GTTTGTATTACCACATGGGCCAATGC (SEQ ID NO:37) and oligo C4. TCTCCCGCTCTTCCGCATTCAT-GCAGTTTTTCATAG ATTTTCTCC (SEQ II) NO: 38) as primers. Both PCR reactions were catalyzed by Pfu DNA polymerase and Bca genomic DNA was used as template. the PCR conditions for both PCRs were: 1 cycle: 94° C. 2 minutes; 25 cycles: 94° C. 45 seconds. 55° C. 45 seconds, 72° C. 2 minutes 45 seconds: 1 cycle: 72° C. 10 minutes. The resulting PCR products, of approximately 1,340 and 530 basepairs, were combined as template in overlap PCR using oligo C1 (SEQ ID NO:35) and C4 (SEQ ID NO:38) as primers under the same conditions as above. The resulting PCR product was digested with NdeI and SapI restriction endonucleases and subcloned into pTXB1 vector. The resulting recombinant DNA, pTXBluvrC, was transformed into *E. coli* C741(DE3) cells. The induction of UvrC was performed at $OD_{600}$~0.6 with 1mM IPTG for 3 hours at 30° C.

Example 5

Reconstitution of the UvrAB System

To test the padlock DNA binding model and the importance the β-hairpin motif in the recognition of DNA damage, a β-hairpin deletion mutant of the *B. caldotenax* UvrB protein, designed as Δβh UvrB, was constructed with amino acid residues from Gln97 to Asp112 removed and the resulting gap bridged by a glycine residue (Skorvaga et al., *J. Biol. Chem.* 277:1553–1559 (2002)). In the resulting deletion mutant only the upper half of the β-hairpin was removed. To test the properties of this mutant, the *B. caldotenax* UvrAB system was reconstituted with purified UvrA and UvrB protein, each obtained via intein fusion proteins, as described in Examples 1 and 2.

Construction of the β-Hairpin Deletion Mutant of UvrB

The deletion of amino acid residues Gln-97 to Asp-112 and the introduction of a glycine residue in the deleted region constitutes the Δβh UvrB mutant. As described in Skorvaga et al., *J. Biol. Chem.* 277:1553–1559 (2002), the uvrB gene was subcloned into a pUC18 vector, and the mutant constructed by PCR using pUC18uvrB as a template DNA.

DNA Substrates

Figure 10:
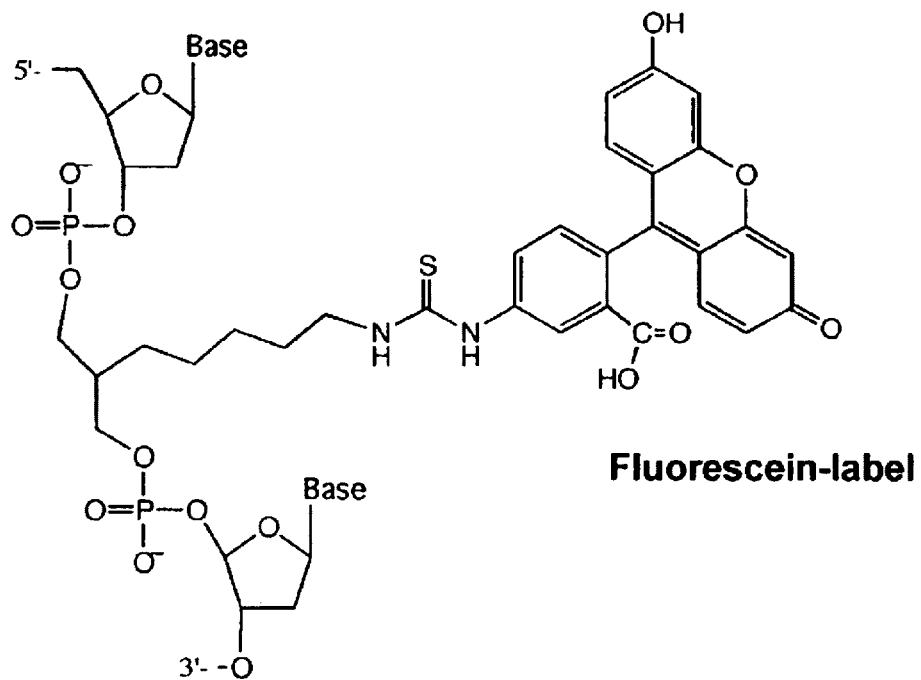
FIG. 10. The F26–50 dsDNA substrate, a 50-base pair duplex with a fluorescein attached at position 26 (SEQ ID NO:41).

Fluorescein-containing DNA substrates were synthesized by Sigma. The DNA sequence of a 50 basepair (bp) double-stranded DNA (dsDNA) substrate containing a single internal fluorescein adduct ($F_{26}$-50 dsDNA) is shown in FIG. 10. For 5' labeling, 10 pmol of 50-mer fluorescein-containing top strand was incubated with 25 units of T4 polynucleotide kinase in 70 mM This/Cl (pH 7.6), 10 mM $MgCl_2$, 100 mM KCl, 1 mM 2-mercaptoethanol, and 15 pmol of $[\gamma-^{32}P]ATP$ (3000 Ci/mmol). After incubation at 37° C. for 1 hour, the reaction was terminated by incubation at 80° C. for 10 minutes in the presence of 20 mM EDTA. Annealing of the top and the bottom strand was performed in the presence of 50 mM NaCl followed by purification through Bio-Spin P-30 polyacrylamide gel column (Bio-Rad Laboratories, Hercules, Calif.) for removal of unincorporated nucleotides. The double-stranded character and homogeneity of the 50-bp substrate were examined by a restriction assay (Zou et al. (1995) *Biochemistry* 34, 13582–13593) and analyzed on a 12% polyacrylamide sequencing gel under denaturating conditions.

The DNA sequence of the helicase substrate (HS1F-M13mp19) is shown in FIG. 11. Five pmol of a 26-mer containing an internal fluorescein adduct (HS1F) were labeled at its 5' terminus under the same conditions as the $F_{26}$-50 top strand. The helicase substrate was constructed by hybridizing 0.4 pmol of 5'-labeled HS1F oligonucleotide with equimolar amounts of M13 mp19(+) strand and purified as described above.

Gel Mobility Shift Assay

Binding reactions were performed with 2 nM DNA substrate (5–$^{32}$P-labeled $F_{26}$-50 dsDNA), 20 nM *B. caldotenax* UvrA, and 60 nM *B. caldotenax* UvrB in 20 µl of UvrABC buffer (50 mM Tris/Cl (pH 7.5), 10 mM $MgCl_2$, 50 mM KCl, 1 mM ATP, 5 mM dithiothreitol) for 20 minutes at 55° C. Glycerol was then added to the reaction 8%v/v), and the reaction mixture was loaded onto a 4% native polyacrylamide gel (80:1). The gel and the running buffer (89 mM Tris, 89 mM boric acid, 2 mM EDTA) contained 1 mM ATP and 10 mM $MgCl_2$. The electrophoresis was performed for 3 hours at 100 V at room temperature. The gel was dried and exposed against Storage Phosphor Screen (Molecular Dynamics, Amersham Biosciences, Sunnyvale, Calif.) overnight at room temperature.

CD Spectroscopy

CD spectra were measured at 20° C. on an Aviv model 62 ADS spectrometer using rectangular cells with a path length of 0.2 mm. Proteins were measured at concentrations between 0.6 and 1.4 mg/ml in a buffer containing 500 mM KF and 10 mM K2HPO4 at pH 7.4. UV absorption at 280 nm was used to determine protein concentrations. The extinction coefficients of wild type UvrB (658 amino acids) and Δβh UvrB (643 amino acids) were calculated from the primary sequence to be 33,280 and 30,720 liters/mol/cm, respectively. The CD spectra were sampled at 1-nm intervals with a time constant of 1 second and 10 scans for both samples and blanks, resulting in an acquisition time of 1 hour for each spectrum.

ATP Hydrolysis Assay

The conversion of ATP to ADP by the UvrAB system was determined by a coupled enzyme assay system consisting of pyruvate kinase and lactate dehydrogenase to link the hydrolysis of ATP to the oxidation of NADH. The assay mixture consisted of 50 mM Tris/Cl (pH 7.5), 50 mM NaCl, 4 mM $MgCl_2$, 1 mM dithiothreitol, 20 units/ml lactate dehydrogenase, 20 units/ml pyruvate kinase, 2 mM phosphoenol pyruvate, 0.15 mM NADH and 200 nM Uvr proteins in the presence or absence of 50 ng of UV-irradiated DNA substrate. DNA substrate was prepared by exposure of pUC 18 DNA to 200 J/m2. *B. caldotenax* UvrA and UvrB proteins were preheated to 55° C. for 10 minutes to inactivate *E. coli* contaminant protein activities. The reaction mixture (0.5 ml) was allowed to equilibrate at 37° C., and the assay was initiated by the addition of ATP (0.5 mM). The rate of ATP hydrolysis was calculated from the linear change in absorbance at λ=340 nm over 30 minutes, which accompanied the oxidation of NADH, using a Beckman spectrophotometer. Determinations were performed in duplicate and done three separate times. Data are reported as the means±S.D.

Loading of the Δβh UvrB Protein onto the Site of Damage

Figure 12A:
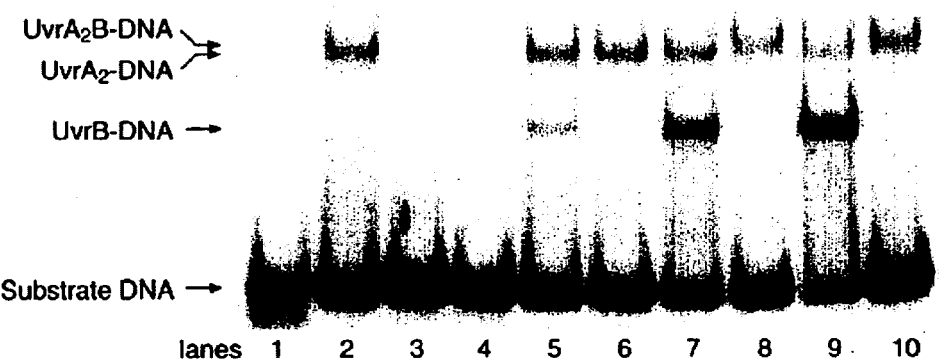
FIG. 12A, lower concentrations of Δβh UvrB (1–10 nM)
Figure 12B:
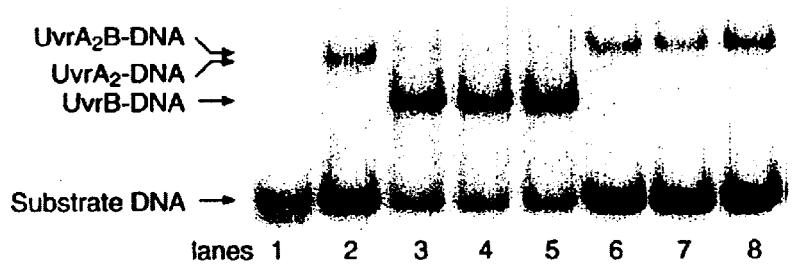
FIG. 12B, higher concentrations of Δβh UvrB (50–200 nM).
Figure 13:
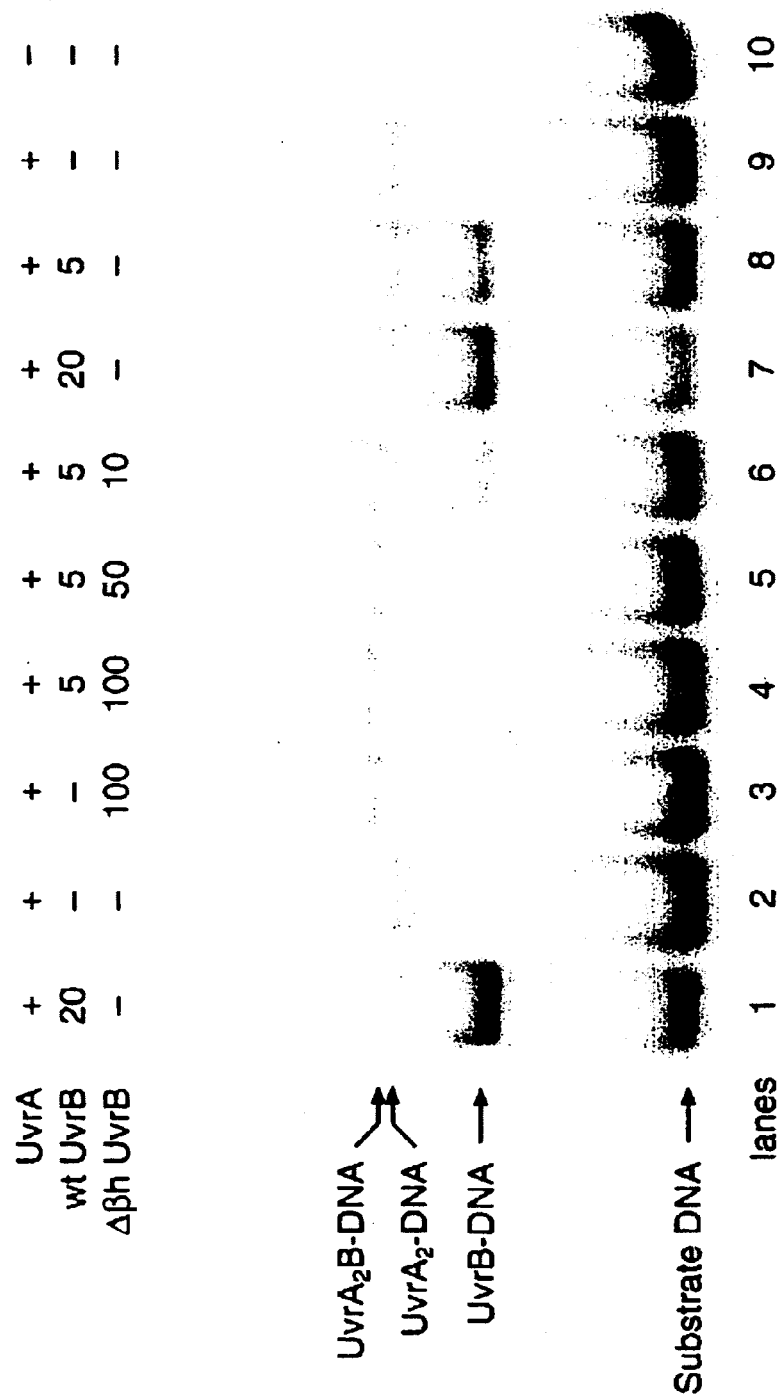
FIG. 13. Competition between wt and Δβh UvrB in binding to ds6-50 dsDNA. UvrA (20 nM), wt UvrB (5 nM), and increasing amounts of Δβh UvrB (10–100 nM) were incubated at 55° C. for 20 minutes with 2 nM F26-50 dsDNA. The reaction mixtures were analyzed by 4% native PAGE using Tris-borate-EDTA running butter with 1 mM ATP and 10 mM MgCl$_2$

A gel mobility shift assay was used to test whether the the UvrB-DNA pre-incision complex intermediate between these processes, is formed with the Δβh UvrB mutant (FIGS. 12 and 13). The Δβh UvrB protein does not form a stable complex with the damaged DNA neither at low concentrations (1–20 nM; FIG. 12A) nor at higher amounts (50–200 nM; FIG. 12B), whereas loading of wild type UvrB is very efficient, even at 5 nM (FIG. 12A, lane 7). It is interesting to note that the band corresponding to the UvrA2-DNA complex (FIG. 12B, lane 2) migrates slightly faster than the samples containing the Δβh UvrB protein (FIG. 12B, lanes 4–6). This slower mobility band probably represents the UvrA2 Δβh UvrB-DNA complex. To further investigate whether Δβh UvrB is able to bind to UvrA, competition experiments between the mutant and the wild type UvrB for binding to UvrA and F26–50 dsDNA wee conducted. In these experiments (FIG. 13) there is a clear difference in mobility between the UvrA2-DNA and UvrA2 Δβh UvrB-DNA complexes (FIG. 13, compare lane 2 with lanes 3–5). Increasing amounts of Δβh UvrB (10, 50, 100 nM) at a constant wild type UvrB concentration (5 nM) resulted in a significant reduction of the amount of wt UvrB-DNA complex (FIG. 13, lanes 4–6 versus lane 8). This dominant negative effect of Δβh UvrB supports the idea that Δβh UvrB is properly folded and shows that it is capable of interacting with UvrA, resulting in the reduction of the amount of UvrA molecules available to interact with wild type UvrB.

CD Spectra of Wild Type and the β-Hairpin Deletion Mutant UvrB

The results of CD spectra of wild type and Δβh UvrB proteins exhibit nearly identical CD spectra for both wild type and mutant proteins, indicating that the deletion of the β-hairpin motif in UvrB does not affect the global folding of the protein.

ATPase Activity of Δβh UvrB

It has been shown previously that ATP binding/hydrolysis is absolutely required for NER (Oh and Grossman (1987) *Proc. Natl. Acad Sci. USA* 84, 3638–3642). In a padlock model (Theis et al. (1999) *EMBO J.* 18, 6899–6907) it has been suggested that the formation of a stable UvrB-DNA pre-incision complex requires free energy, which might be available either through ATP hydrolysis by UvrA$_2$B or as a result of complex formation. To test whether the altered DNA binding properties of Δβh UvrB are due to an altered ATPase activity, this activity was examined for both wild type UvrB and Δβh UvrB (Table 4). By itself, Δβh UvrB has a very low ATPase activity at 37° C. (2.88 mol of ATPase/min/mg of protein), similar to wild type UvrB (1.40 mol!min/mg). In this respect, *B. caldotenax* UvrB resembles *E. coli* UvrB that has a cryptic ATPase activity. It has been shown that full ATPase activity of UvrB requires the presence of both UvrA and DNA (Caron and Grossman (1988) *Nucleic Acids Res.* 16, 10891–10902). The present data show that the ATPase activity of Δβh UvrB is not affected by deletion of the β-hairpin motif In fact, in the presence of UV-irradiated DNA, the ATPase activity of the UvrA$_2$ Δβh UvrB complex is higher than that of the UvrA2 wt UvrB complex (29 and 22 μmol/min/mg, respectively). This is further evidence that UvrA and Δβh UvrB interact, as was suggested by the results of the gel mobility shifts, CD spectra and helicase assay). The deletion of the β-hairpin does not interfere with the ATP hydrolysis by UvrB in the UvrA$_2$B complex.

TABLE 4

ATPase activity of *B. caldotenax* UvrA, and UvrB

| Samples | ATPase activity (mol of ATP hydrolyzed/ mol of protein/min) |
| --- | --- |
| UvrA | 13.2 ± 0.6 |
| UvrA + UV-DNA* | 17.0 ± 1.0 |
| UvrB | 1.4 ± 0.1 |
| UvrB + UV-DNA* | 1.4 ± 0.1 |
| UvrA + UvrB | 18.3 ± 1.1 |
| UvrA + UvrB + UV-DNA* | 22.0 ± 0.5 |
| Δβh UvrB | 2.8 ± 0.1 |
| UvrA + Δβh UvrB | 19.0 ± 0.6 |
| UvrA + Δβh UvrB + UV-DNA* | 29.0 ± 1.0 |

*UV-DNA represents UV-irradiated DNA

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Sequence Listing Free Text

SEQ ID NO: 7–17, 30, and 32 are peptide sequences.

SEQ ID NO:20–29, 31, and 33–38 are primer sequences.

SEQ ID NO:39 is an oligonucleotide consensus sequence.

SEQ ID NO:40 is a polypeptide consensus sequence.

SEQ ID NO: 41–44 are oligonucleotide sequences.

What is claimed is:

1. A method for detecting DNA damage, the method comprising:
   combining a first polypeptide, a second polypeptide and a double stranded DNA to form a mixture;
   wherein the first polypeptide is encoded by a first polynucleotide, wherein the complement of the first polynucleotide hybridizes to SEQ ID NO:1 under standard hybridization conditions, and wherein the first polypeptide forms a complex at about 50° C. to about 80° C., the complex comprising the first polypeptide, a UvrB polypeptide comprising SEQ ID NO:4, and a BPDE-DNA substrate;
   wherein the second polypeptide is encoded by a second polynucleotide wherein the complement of the second polynucleotide hybridizes to SEQ ID NO:3 under standard hybridization conditions, and wherein the second polypeptide forms a complex at about 50° C. to about 80° C., the complex comprising the second polypeptide, a UvrA polypeptide comprising SEQ ID NO:2, and a BPDE-DNA substrate;
   incubating the mixture such that a complex forms comprising the first polypeptide, the second polypeptide, and the double stranded DNA;
   detecting the complex, wherein the presence of a complex indicates the presence of DNA damage;
   wherein standard hybridization conditions are 6×SSC, 5×Denhardt, 0.5% sodium dodecyl sulfate (SDS), and 100 µg/ml fragmented and denatured salmon sperm DNA hybridized overnight at 65° C. and washed in 2×SSC, 0.1% SDS at least one time at room temperature for about 10 minutes followed by at least one wash at 65° C. for about 15 minutes followed by at least one wash in 0.2×SSC, 0.1% SDS at room temperature for at least 3–5 minutes.

2. The method of claim 1 wherein the detection of a complex comprises detecting the presence of the second polypeptide.

3. The method of claim 2 wherein the presence of the second polypeptide is detected with an antibody that binds to the second polypeptide.

4. The method of claim 1 wherein the first polypeptide comprises SEQ ID NO:2.

5. The method of claim 1 wherein the second polypeptide comprises SEQ ID NO:4.

6. The method of claim 1 wherein the double stranded DNA is from a subject.

7. The method of claim 6 wherein the subject has undergone, is undergoing or will undergo, treatment for cancer.

8. The method of claim 7 wherein the treatment comprises chemotherapy.

9. The method of claim 7 wherein the double stranded DNA is obtained from the subject before treatment.

10. The method of claim 6 wherein the subject has been exposed to, is undergoing exposure to, or will be exposed to a genotoxin.

11. The method of claim 10 wherein the double stranded DNA sample is obtained from the subject before exposure to a genotoxin.

12. A method for detecting DNA damage, the method comprising:
    combining a first polypeptide, a second polypeptide and a double stranded DNA to form a mixture;
    wherein the first polypeptide has at least about 95% sequence identity to SEQ ID NO:2 and wherein the first polypeptide forms a complex at about 50° C. to about 80° C., the complex comprising the first polypeptide, a UvrB polypeptide comprising SEQ ID NO:4, and a BPDE-DNA substrate;
    wherein the second polypeptide has at least about 95% sequence identity to SEQ ID NO:4 and wherein the second polypeptide forms a complex at about 50° C. to about 80° C., the complex comprising the second polypeptide, a UvrA polypeptide comprising SEQ ID NO:2, and a BPDE-DNA substrate;
    incubating the mixture such that a complex forms comprising the first polypeptide, the second polypeptide, and the double stranded DNA;
    detecting the complex, wherein the presence of a complex indicates the presence of DNA damage.

13. The method of claim 1 wherein the double stranded DNA is from a microbe, a plant, or an animal subject.

14. The method of claim 7 wherein the double stranded DNA is obtained from the subject during treatment.

15. The method of claim 7 wherein the double stranded DNA is obtained from the subject after treatment.

16. The method of claim 10 wherein the double stranded DNA sample is obtained from the subject during exposure to a genotoxin.

17. The method of claim 10 wherein the double stranded DNA sample is obtained from the subject after exposure to a genotoxin.

* * * * *

UNITED STATES PATENT AND TRADEMARK OFFICE
CERTIFICATE OF CORRECTION

PATENT NO. : 6,921,641 B2
DATED : July 26, 2005
INVENTOR(S) : Van Houten et al.

It is certified that error appears in the above-identified patent and that said Letters Patent is hereby corrected as shown below:

Column 12,
Line 18, delete "GTTACGGCTCCATCGCTACC GCAATCAGGCCA" and insert
-- GTTACGGCTCCATCGCTACCGCAATCAGGCCA --;

Column 18,
Line 18, insert -- . -- after "protein" and add a paragraph break after inserted -- . -- and before "Included";

Column 21,
Line 51, delete "UNCI 158" and insert -- UNC1158 --;

Column 22,
Line 27, delete "b/a" and insert -- *bla* --;
Line 45, delete "UNCI 158" and insert -- UNC1158 --;

Column 24,
Line 32, delete "*Helicohacter*" and insert -- *Helicobacter* --;

Column 25,
Lines 46 and 49, delete the paragraph breaks before "However," and "These".

Signed and Sealed this

Twenty-first Day of February, 2006

JON W. DUDAS
*Director of the United States Patent and Trademark Office*

SEQUENCE LISTING

<160> NUMBER OF SEQ ID NOS: 71

<210> SEQ ID NO 1
<211> LENGTH: 2859
<212> TYPE: DNA
<213> ORGANISM: BACILLUS CALDOTENAX

<400> SEQUENCE: 1

| | | | | | |
|---|---|---|---|---|---|
| atggataaaa | ttgtcgtcaa | agggcgcgc | gcccacaact | tgaaaaacat | tgacgtcgaa | 60 |
| atcccgcgcg | gcaagctcgt | ggtcttgacc | gggctgtccg | ggtcgggaa | gtcgtcgctg | 120 |
| gcgtttgata | cgatttacgc | ggaaggccag | cgccgctacg | tcgaatcgct | gtcggcgtat | 180 |
| gcccgccagt | ttttagggca | gatggaaaaa | ccggacgtcg | atgcgattga | aggttgtcg | 240 |
| ccggccattt | cgatcgatca | aaaaacgacg | agccgcaacc | cgcgctcaac | cgtcggcacg | 300 |
| gtgacggaaa | tttacgatta | tttacggctg | ctgttcgccc | gcatcggccg | cccagtttgc | 360 |
| ccgacgcacg | gcattgaaat | ccaatcgcag | acgatcgagc | aaatggtcga | ccggttgctc | 420 |
| gcttacccgg | agcggacgaa | aatgcaaatt | ttggcgccga | tcgtctcggg | aaaaaaaggg | 480 |
| acgcacgcca | agacattgga | ggatattcgc | aaacaagggt | atgtgcgcgt | ccgcattgac | 540 |
| ggcgagatgc | gcgagttgac | ggaggacatt | gagctgaaaa | aaacaaaaa | acattcgatt | 600 |
| gatgtcgtcg | tcgaccgcat | catcatcaaa | gacggcatcg | ccgccaggct | tgccgattcg | 660 |
| cttgagacgc | gctgaagct | cgccgacggc | aaagtggtcg | ttgacgtgat | cggcgagggg | 720 |
| gagctcttgt | tcagcgaaaa | gcacgcttgt | ccgtactgcg | gcttttcgat | cggggagctt | 780 |
| gaaccgcgtc | tgttttcgtt | caacagtcca | ttcggcgcct | gcccggactg | cgacgggctc | 840 |
| ggggcgaagc | tcgaagtgga | tctcgatttg | gtcatcccga | acgatgagct | gacgttaaaa | 900 |
| gaacacgcca | tcgctccgtg | ggagccgcaa | agctcgcaat | attacccgca | gctgctcgaa | 960 |
| gccgtgtgcc | gccattacgg | catcccgatg | gacgtgccgg | tcagagattt | gccgaaagag | 1020 |
| cagctcgata | aaattttgta | cggcagcggc | ggagagccga | tttatttccg | ctatacgaat | 1080 |
| gatttcggac | aagtgcgcga | acaatacatc | gcatttgaag | gcgtcattcc | gaacgtcgaa | 1140 |
| cgccgctatc | gcgagacgag | ctcggactac | atccgcgagc | agatggaaaa | gtatatggcg | 1200 |
| gaacaaccat | gtccgacatg | ccaaggctac | cggctgaaaa | aagaaagcct | ggccgtcctt | 1260 |
| gtcggcggca | agcatatcgg | cgaggtcacc | gccatgtcgg | tgaccgaggc | gctcgccttt | 1320 |
| tttgacgggc | tcgagctgac | cgaaaaagaa | gcgcaaatcg | cccgccttat | tttgcgtgaa | 1380 |
| attcgcgacc | ggctcggctt | tttgcaaaac | gtcggcctcg | actatttgac | gctcagccgc | 1440 |
| tcggcaggaa | cgctctccgg | cggcgaggcg | cagcgcatcc | gcttggcgac | gcagatcggc | 1500 |
| tcgcggctga | cggggtgct | gtacgtgctc | gacgagccgt | cgatcgggct | tcatcagcgc | 1560 |
| gacaacgacc | ggctgatcgc | gacgttgaaa | agcatgcgcg | acctcggcaa | tacgctcatt | 1620 |
| gtggtggagc | acgacgagga | taccatgctg | gccgcggact | atttgattga | cattggtccg | 1680 |
| ggggcgggca | tccacggcgg | cgaagtcata | tctgcgggta | cgccggaaga | agtgatggaa | 1740 |
| gatccaaatt | cattaacggg | cagctatta | tcggggaaaa | aatttatccc | attgcctcct | 1800 |
| gaaagaagaa | agccggacgg | acgttacatt | gaaattaaag | gcgcgcgcga | gcataacttg | 1860 |
| aaaaacgtat | cggtgaaaat | cccgctcggc | acgtttgtcg | ctgtcaccgg | ggtgtcggc | 1920 |
| tcgggcaaaa | gcacgcttgt | gaacgaagtg | ttgtataagg | cgctggcgca | aaagctgcac | 1980 |
| cgggcgaagg | cgaaaccggg | cgagcaccgc | gacattcgcg | ggctggagca | tctcgataaa | 2040 |

-continued

```
gtcattgaca tcgaccagtc gccgatcggc cgcacgccac gctcgaaccc ggcgacgtac    2100 accgggtgt ttgacgacat ccgcgacgtg tttgcctcga cgaacgaagc gaaagtgcgc    2160
ggctacaaaa aagggcggtt cagcttcaat gtcaaaggcg ggcgctgcga ggcgtgccat    2220
ggcgatggca tcatcaaaat tgagatgcac ttttgccgg acgtgtacgt cccgtgcgaa    2280
gtgtgccacg gcaaacggta caaccgcgag acgctcgagg tgacgtataa aggaaaaaac    2340
atcgccgagg tgctcgacat gacggtcgaa gatgcgctcg acttttcgc ctcgatcccg    2400 aaaatcaaac gcaagctcga gacgctctat gacgtcgggc tcggttatat gaagctcggc    2460
cagccggcga cgacgctctc gggcggcgag gcgcagcgcg tcaagctcgc cgctgagctt    2520
caccgccgct ccaacggccg gacgctctac attttggacg agccgacgac cgggcttcat    2580
gtcgatgaca tcgcccggct gcttgatgtg ctccaccggc tcgtcgacaa cggcgatacc    2640
gtgcttgtca ttgaacataa cttggacgtc atcaaaaccg cggactatat cattgactta    2700
ggtccggaag gcggcgaccg aggcggacaa atcgtcgctg tcggcacgcc ggaagaggtg    2760
gccgaggtgg aggagtcgca caccggccgc tacttaaacc cgattctcga gcgcgaccgg    2820
gcgcgcatgc aggcgcaata tgaagcggtg aaggcgtaa                          2859
```

<210> SEQ ID NO 2
<211> LENGTH: 952
<212> TYPE: PRT
<213> ORGANISM: BACILLUS CALDOTENAX

<400> SEQUENCE: 2

```
Met Asp Lys Ile Val Val Lys Gly Ala Arg Ala His Asn Leu Lys Asn
1               5                  10                  15

Ile Asp Val Glu Ile Pro Arg Gly Lys Leu Val Val Leu Thr Gly Leu
            20                  25                  30

Ser Gly Ser Gly Lys Ser Ser Leu Ala Phe Asp Thr Ile Tyr Ala Glu
        35                  40                  45

Gly Gln Arg Arg Tyr Val Glu Ser Leu Ser Ala Tyr Ala Arg Gln Phe
    50                  55                  60

Leu Gly Gln Met Glu Lys Pro Asp Val Asp Ala Ile Glu Gly Leu Ser
65                  70                  75                  80

Pro Ala Ile Ser Ile Asp Gln Lys Thr Thr Ser Arg Asn Pro Arg Ser
                85                  90                  95

Thr Val Gly Thr Val Thr Glu Ile Tyr Asp Tyr Leu Arg Leu Leu Phe
            100                 105                 110

Ala Arg Ile Gly Arg Pro Val Cys Pro Thr His Gly Ile Glu Ile Gln
        115                 120                 125

Ser Gln Thr Ile Glu Gln Met Val Asp Arg Leu Leu Ala Tyr Pro Glu
    130                 135                 140

Arg Thr Lys Met Gln Ile Leu Ala Pro Ile Val Ser Gly Lys Lys Gly
145                 150                 155                 160

Thr His Ala Lys Thr Leu Glu Asp Ile Arg Lys Gln Gly Tyr Val Arg
                165                 170                 175

Val Arg Ile Asp Gly Glu Met Arg Glu Leu Thr Glu Asp Ile Glu Leu
            180                 185                 190

Glu Lys Asn Lys Lys His Ser Ile Asp Val Val Asp Arg Ile Ile
        195                 200                 205

Ile Lys Asp Gly Ile Ala Ala Arg Leu Ala Asp Ser Leu Glu Thr Ala
    210                 215                 220
```

-continued

```
Leu Lys Leu Ala Asp Gly Lys Val Val Asp Val Ile Gly Glu Gly
225                 230                 235                 240

Glu Leu Leu Phe Ser Glu Lys His Ala Cys Pro Tyr Cys Gly Phe Ser
            245                 250                 255

Ile Gly Glu Leu Glu Pro Arg Leu Phe Ser Phe Asn Ser Pro Phe Gly
        260                 265                 270

Ala Cys Pro Asp Cys Asp Gly Leu Gly Ala Lys Leu Glu Val Asp Leu
    275                 280                 285

Asp Leu Val Ile Pro Asn Asp Glu Leu Thr Leu Lys Glu His Ala Ile
290                 295                 300

Ala Pro Trp Glu Pro Gln Ser Ser Gln Tyr Tyr Pro Gln Leu Leu Glu
305                 310                 315                 320

Ala Val Cys Arg His Tyr Gly Ile Pro Met Asp Val Pro Val Arg Asp
            325                 330                 335

Leu Pro Lys Glu Gln Leu Asp Lys Ile Leu Tyr Gly Ser Gly Gly Glu
        340                 345                 350

Pro Ile Tyr Phe Arg Tyr Thr Asn Asp Phe Gly Gln Val Arg Glu Gln
    355                 360                 365

Tyr Ile Ala Phe Glu Gly Val Ile Pro Asn Val Glu Arg Arg Tyr Arg
370                 375                 380

Glu Thr Ser Ser Asp Tyr Ile Arg Glu Gln Met Glu Lys Tyr Met Ala
385                 390                 395                 400

Glu Gln Pro Cys Pro Thr Cys Gln Gly Tyr Arg Leu Lys Lys Glu Ser
            405                 410                 415

Leu Ala Val Leu Val Gly Gly Lys His Ile Gly Glu Val Thr Ala Met
        420                 425                 430

Ser Val Thr Glu Ala Leu Ala Phe Phe Asp Gly Leu Glu Leu Thr Glu
    435                 440                 445

Lys Glu Ala Gln Ile Ala Arg Leu Ile Leu Arg Glu Ile Arg Asp Arg
450                 455                 460

Leu Gly Phe Leu Gln Asn Val Gly Leu Asp Tyr Leu Thr Leu Ser Arg
465                 470                 475                 480

Ser Ala Gly Thr Leu Ser Gly Gly Glu Ala Gln Arg Ile Arg Leu Ala
            485                 490                 495

Thr Gln Ile Gly Ser Arg Leu Thr Gly Val Leu Tyr Val Leu Asp Glu
        500                 505                 510

Pro Ser Ile Gly Leu His Gln Arg Asp Asn Asp Arg Leu Ile Ala Thr
    515                 520                 525

Leu Lys Ser Met Arg Asp Leu Gly Asn Thr Leu Ile Val Val Glu His
530                 535                 540

Asp Glu Asp Thr Met Leu Ala Ala Asp Tyr Leu Ile Asp Ile Gly Pro
545                 550                 555                 560

Gly Ala Gly Ile His Gly Gly Glu Val Ile Ser Ala Gly Thr Pro Glu
            565                 570                 575

Glu Val Met Glu Asp Pro Asn Ser Leu Thr Gly Ser Tyr Leu Ser Gly
        580                 585                 590

Lys Lys Phe Ile Pro Leu Pro Pro Glu Arg Arg Lys Pro Asp Gly Arg
    595                 600                 605

Tyr Ile Glu Ile Lys Gly Ala Arg Glu His Asn Leu Lys Asn Val Ser
610                 615                 620

Val Lys Ile Pro Leu Gly Thr Phe Val Ala Val Thr Gly Val Ser Gly
625                 630                 635                 640

Ser Gly Lys Ser Thr Leu Val Asn Glu Val Leu Tyr Lys Ala Leu Ala
```

```
                    645                 650                 655
Gln Lys Leu His Arg Ala Lys Ala Lys Pro Gly Glu His Arg Asp Ile
                660                 665                 670
Arg Gly Leu Glu His Leu Asp Lys Val Ile Asp Ile Asp Gln Ser Pro
                675                 680                 685
Ile Gly Arg Thr Pro Arg Ser Asn Pro Ala Thr Tyr Thr Gly Val Phe
                690                 695                 700
Asp Asp Ile Arg Asp Val Phe Ala Ser Thr Asn Glu Ala Lys Val Arg
705                 710                 715                 720
Gly Tyr Lys Lys Gly Arg Phe Ser Phe Asn Val Lys Gly Gly Arg Cys
                725                 730                 735
Glu Ala Cys His Gly Asp Gly Ile Ile Lys Ile Glu Met His Phe Leu
                740                 745                 750
Pro Asp Val Tyr Val Pro Cys Glu Val Cys His Gly Lys Arg Tyr Asn
                755                 760                 765
Arg Glu Thr Leu Glu Val Thr Tyr Lys Gly Lys Asn Ile Ala Glu Val
                770                 775                 780
Leu Asp Met Thr Val Glu Asp Ala Leu Asp Phe Phe Ala Ser Ile Pro
785                 790                 795                 800
Lys Ile Lys Arg Lys Leu Glu Thr Leu Tyr Asp Val Gly Leu Gly Tyr
                805                 810                 815
Met Lys Leu Gly Gln Pro Ala Thr Thr Leu Ser Gly Gly Glu Ala Gln
                820                 825                 830
Arg Val Lys Leu Ala Ala Glu Leu His Arg Arg Ser Asn Gly Arg Thr
                835                 840                 845
Leu Tyr Ile Leu Asp Glu Pro Thr Thr Gly Leu His Val Asp Asp Ile
                850                 855                 860
Ala Arg Leu Leu Asp Val Leu His Arg Leu Val Asp Asn Gly Asp Thr
865                 870                 875                 880
Val Leu Val Ile Glu His Asn Leu Asp Val Ile Lys Thr Ala Asp Tyr
                885                 890                 895
Ile Ile Asp Leu Gly Pro Glu Gly Gly Asp Arg Gly Gly Gln Ile Val
                900                 905                 910
Ala Val Gly Thr Pro Glu Glu Val Ala Glu Val Glu Ser His Thr
                915                 920                 925
Gly Arg Tyr Leu Asn Pro Ile Leu Glu Arg Asp Arg Ala Arg Met Gln
                930                 935                 940
Ala Gln Tyr Glu Ala Val Lys Ala
945                 950

<210> SEQ ID NO 3
<211> LENGTH: 1977
<212> TYPE: DNA
<213> ORGANISM: BACILLUS CALDOTENAX

<400> SEQUENCE: 3
gtggagggcc gttttcaatt agtggcgcca tacgaaccgc aaggcgatca gccgcaggcg    60
atcgccaagc tcgttgacgg cctgcgccgc ggggtgaagc atcaaacgct gcttggggcg   120
acggggacgg gcaaaacgtt tacgatctcg aacgtgatcg cccaagtcaa caaaccgacg   180
cttgtcatcg cccacaacaa aacgctcgct ggccaattgt acagcgagct gaaagagttt   240
ttcccgcaca cgccgtcga atattttgtc agctattacg attactatca gccggaagcg   300
tatgtgccgc agacggatac gtacattgaa aaagacgcga aaatcaacga tgaaatcgac   360
```

-continued

```
aaattgcggc actcggcgac atcagccttg tttgagcgcc gggacgtgat tatcgttgcg    420
agcgtgtcgt gcatttacgg tttagggtcg ccggaagagt accgcgaact ggtcgtatcg    480
ctgcgcgttg ggatggagat cgagcgcaac gcgttgcttc ggcggcttgt cgacatccaa    540
tacgaccgca atgacatcga ttttcgccgc ggcacgttcc gcgtccgcgg cgatgttgtc    600
gaaattttcc ccgcgtcgcg cgatgaacat tgcatccgcg tcgaattttt cggcgatgaa    660
atcgagcgca tccgcgaggt ggacgcctta accggcgagg tgctcggcga gcgcgagcat    720
gtcgccattt tcccggcgtc gcacttcgtg acgcgcgagg agaaaatgcg gctcgccatt    780
caaaacatcg aacaagagct tgaggagcgg cttgccgaac tgcgcgcgca aggaaagctc    840
ttagaggcgc agcggcttga gcagcggacg cgctatgacc ttgaaatgat gcgcgagatg    900
ggcttttgtt ccggcatcga aaactactcg cgccatttgg cgctgcggcc gccaggctcg    960
acgccgtata cattgcttga ctattttccg gacgattttt tgatcatcgt tgatgagtcg   1020
cacgtcacct tgccgcagct gcgcggcatg tacaacggcg accgggcgcg caagcaagtg   1080
cttgtcgacc acggcttccg tctgccgtcg gcgcttgaca accggccgct cacgtttgaa   1140
gagttcgagc aaaaaatcaa tcaaattatt tacgtctcag cgacgccggg gccgtatgag   1200
cttgaacaca gcccgggcgt tgtcgaacaa atcatccgcc cgaccgggct tctcgaccca   1260
acgatcgacg tccgcccgac gaaagggcaa atcgacgatt tgatcggcga aattcgcgag   1320
cgcgtcgagc ggaacgagcg gacgttggtg acgacgctga cgaaaaagat ggcggaagat   1380
ttgaccgatt atttgaaaga gcggggatc aaggtggcgt atttgcattc ggaaattaag   1440
acgctcgagc gcattgaaat catccgcgat ttgcggctcg gcaaatacga tgtattggtc   1500
ggcatcaact tgcttcgcga agggctcgac atcccagaag tgtcgcttgt cgccattttg   1560
gacgccgaca agaagggtt tttgcgctcg gagcgctcgc tcatccagac gatcggccgg   1620
gcggcgcgca acgcgaacgg ccatgtgatc atgtacgccg atacgatcac gaaatcgatg   1680
gaaatcgcca ttcaagagac gaagcggcgc cgcgcgattc aagaagagta caaccgaaag   1740
cacggcatcg tgccgcgcac ggtgaaaaag gagattcgcg acgtcatccg cgcgacgtat   1800
gcggcggaag agacggagat gtacgaggca aagccggcgg cagcgatgac gaaacaagag   1860
cgggaagagc tgattcgaac gctcgaagcg gaaatgaaag aggcggccaa agcgctcgac   1920
ttcgagcggg ccgcccagct gcgcgatatc attttcgaat tgaaagcgga agggtga    1977
```

<210> SEQ ID NO 4
<211> LENGTH: 658
<212> TYPE: PRT
<213> ORGANISM: BACILLUS CALDOTENAX

<400> SEQUENCE: 4

```
Val Glu Gly Arg Phe Gln Leu Val Ala Pro Tyr Glu Pro Gln Gly Asp
 1               5                  10                  15

Gln Pro Gln Ala Ile Ala Lys Leu Val Asp Gly Leu Arg Arg Gly Val
            20                  25                  30

Lys His Gln Thr Leu Leu Gly Ala Thr Gly Thr Gly Lys Thr Phe Thr
        35                  40                  45

Ile Ser Asn Val Ile Ala Gln Val Asn Lys Pro Thr Leu Val Ile Ala
    50                  55                  60

His Asn Lys Thr Leu Ala Gly Gln Leu Tyr Ser Glu Leu Lys Glu Phe
65                  70                  75                  80

Phe Pro His Asn Ala Val Glu Tyr Phe Val Ser Tyr Tyr Asp Tyr Tyr
                85                  90                  95
```

-continued

```
Gln Pro Glu Ala Tyr Val Pro Gln Thr Asp Thr Tyr Ile Glu Lys Asp
                100                 105                 110

Ala Lys Ile Asn Asp Glu Ile Asp Lys Leu Arg His Ser Ala Thr Ser
            115                 120                 125

Ala Leu Phe Glu Arg Arg Asp Val Ile Val Ala Ser Val Ser Cys
            130                 135                 140

Ile Tyr Gly Leu Gly Ser Pro Glu Glu Tyr Arg Glu Leu Val Val Ser
145                 150                 155                 160

Leu Arg Val Gly Met Glu Ile Glu Arg Asn Ala Leu Leu Arg Arg Leu
                165                 170                 175

Val Asp Ile Gln Tyr Asp Arg Asn Asp Ile Asp Phe Arg Arg Gly Thr
                180                 185                 190

Phe Arg Val Arg Gly Asp Val Glu Ile Phe Pro Ala Ser Arg Asp
            195                 200                 205

Glu His Cys Ile Arg Val Glu Phe Phe Gly Asp Glu Ile Glu Arg Ile
            210                 215                 220

Arg Glu Val Asp Ala Leu Thr Gly Glu Val Leu Gly Glu Arg Glu His
225                 230                 235                 240

Val Ala Ile Phe Pro Ala Ser His Phe Val Thr Arg Glu Lys Met
                245                 250                 255

Arg Leu Ala Ile Gln Asn Ile Glu Gln Glu Leu Glu Glu Arg Leu Ala
            260                 265                 270

Glu Leu Arg Ala Gln Gly Lys Leu Leu Glu Ala Gln Arg Leu Glu Gln
            275                 280                 285

Arg Thr Arg Tyr Asp Leu Glu Met Met Arg Glu Met Gly Phe Cys Ser
            290                 295                 300

Gly Ile Glu Asn Tyr Ser Arg His Leu Ala Leu Arg Pro Pro Gly Ser
305                 310                 315                 320

Thr Pro Tyr Thr Leu Leu Asp Tyr Phe Pro Asp Asp Phe Leu Ile Ile
                325                 330                 335

Val Asp Glu Ser His Val Thr Leu Pro Gln Leu Arg Gly Met Tyr Asn
                340                 345                 350

Gly Asp Arg Ala Arg Lys Gln Val Leu Val Asp His Gly Phe Arg Leu
            355                 360                 365

Pro Ser Ala Leu Asp Asn Arg Pro Leu Thr Phe Glu Glu Phe Glu Gln
            370                 375                 380

Lys Ile Asn Gln Ile Ile Tyr Val Ser Ala Thr Pro Gly Pro Tyr Glu
385                 390                 395                 400

Leu Glu His Ser Pro Gly Val Val Glu Gln Ile Ile Arg Pro Thr Gly
                405                 410                 415

Leu Leu Asp Pro Thr Ile Asp Val Arg Pro Thr Lys Gly Gln Ile Asp
                420                 425                 430

Asp Leu Ile Gly Glu Ile Arg Glu Arg Val Glu Arg Asn Glu Arg Thr
            435                 440                 445

Leu Val Thr Thr Leu Thr Lys Lys Met Ala Glu Asp Leu Thr Asp Tyr
450                 455                 460

Leu Lys Glu Ala Gly Ile Lys Val Ala Tyr Leu His Ser Glu Ile Lys
465                 470                 475                 480

Thr Leu Glu Arg Ile Glu Ile Ile Arg Asp Leu Arg Leu Gly Lys Tyr
                485                 490                 495

Asp Val Leu Val Gly Ile Asn Leu Leu Arg Glu Gly Leu Asp Ile Pro
            500                 505                 510
```

-continued

Glu Val Ser Leu Val Ala Ile Leu Asp Ala Asp Lys Glu Gly Phe Leu
            515                 520                 525
Arg Ser Glu Arg Ser Leu Ile Gln Thr Ile Gly Arg Ala Ala Arg Asn
        530                 535                 540
Ala Asn Gly His Val Ile Met Tyr Ala Asp Thr Ile Thr Lys Ser Met
545                 550                 555                 560
Glu Ile Ala Ile Gln Glu Thr Lys Arg Arg Ala Ile Gln Glu Glu
                565                 570                 575
Tyr Asn Arg Lys His Gly Ile Val Pro Arg Thr Val Lys Lys Glu Ile
                580                 585                 590
Arg Asp Val Ile Arg Ala Thr Tyr Ala Ala Glu Glu Thr Glu Met Tyr
            595                 600                 605
Glu Ala Lys Pro Ala Ala Ala Met Thr Lys Gln Glu Arg Glu Glu Leu
        610                 615                 620
Ile Arg Thr Leu Glu Ala Glu Met Lys Glu Ala Lys Ala Leu Asp
625                 630                 635                 640
Phe Glu Arg Ala Ala Gln Leu Arg Asp Ile Ile Phe Glu Leu Lys Ala
                645                 650                 655
Glu Gly

<210> SEQ ID NO 5
<211> LENGTH: 1773
<212> TYPE: DNA
<213> ORGANISM: BACILLUS CALDOTENAX

<400> SEQUENCE: 5

| | |
|---|---|
| atgaacgagc ggctgaaaga aaaactggct gtgctgccgg agcagccggg ctgctatttg | 60 |
| atgaaagaca aacacggaac ggtgatttat gtcgggaagg cgaagtcgct gaaagagcgc | 120 |
| gtccgctcgt atttaccgg gacgcatgac ggcaagacgc agcggcttgt tgaggagatc | 180 |
| gctgatttcg aatacatcgt cacctcgtca acgccgagg cgctcatttt ggagatgaat | 240 |
| ttgatcaaaa agcatgatcc gaaatacaac gtcatgctga agatgataa aagctacccg | 300 |
| tttattaaaa tcaccgcaga aaagcatccg cgcctgctta tcacccgcaa agtgaaaaaa | 360 |
| gacggcggca atatttcgg cccgtatcca acgtgcagg cggcgaacga acgaaaaag | 420 |
| ctgctcgacc gctatatcc gctccgcaaa tgttcgacgc tgccttcgcg cgcctgtttg | 480 |
| tattaccata tgggccaatg cctcgccccg tgcgtccacc cggtgtcgga cgaacaaaat | 540 |
| aaggcgatgg ttgaacaaat cgtccgcttt taaacggcg gtatgaaga cgtgaagcgg | 600 |
| gagttggccg agaaaatgca cgaggcggcg aaacgctcg agtttgaacg ggcgaaagaa | 660 |
| taccgcgatc aaatcgcggc gattgagatg acgatggaaa agcaaaaaat gatgctcaac | 720 |
| gacttcatcg accgcgatgt attcggctat gcgtacgaca aaggctggat gtgcgtgcaa | 780 |
| gtgttttttcc ttcgccaagg gaagctgatt gagcgcgacg tgtcgatctt cccgctttac | 840 |
| caagacccgg atgaggaaat gcttacgttt ttgggtcagt tttatgcgaa agcgcatcat | 900 |
| ttgaagccaa aagaagtcgt tctcccgtcc gacattgacg gcgagctcgc ccgcgaattg | 960 |
| ctcggcgttg ccgtcgtcca gccgaaaaaa gggaagaaaa aagagcttgt tgagctggcg | 1020 |
| agcaaaaacg cggccattgc tctgaaagaa aaatttttatt tcatcgagcg ggacgaagaa | 1080 |
| cggacgatca aagcggtcga acgtctcgga gagcgtcttg gcattccggc gccgcgccgc | 1140 |
| atcgaggcgt ttgacaactc gaacatttac ggggccgatc cggtctcggc gctcgtcgtt | 1200 |
| ttcctcgatg gcaagccggc gaaaaagaa taccggaaat ataaggtgaa aacggtcgcg | 1260 |

-continued

```
gggccgaacg attatgaaac gatgcgcgaa gtcgtgcgcc gccgctatac gcgcgtgttg      1320
aaagaaggat tgccgcttcc cgatttgatc attatcgacg gcggcaaagg ccacttgtcg      1380
gcggtgcggg atgtgctcga aaacgaactt ggactggatg tgccgctggc tggattggcg      1440
aaagacgaaa acatcgcac atcagagctt ttggccggcg accgccgga tgtcgtgccg        1500 ctcgaccggc aaagccaaga gttttattta ttgcagcgca tccaggatga agtgcatcgg      1560
tttgccgtta tgtttcaccg aaagacgcgg cagaaaacga tgttccattc cgtgcttgat     1620
gacatccccg cgtcggggga aaagcggaaa aaagcactct tgaattattt cggctctgtg      1680
aaaaagatga aagaggcgac ggtggaagag ttgcagcggg cgaacattcc gcgagcggtg      1740
gcggagaaaa tctatgaaaa actgcatgaa taa                                   1773
```

<210> SEQ ID NO 6
<211> LENGTH: 590
<212> TYPE: PRT
<213> ORGANISM: BACILLUS CALDOTENAX

<400> SEQUENCE: 6

```
Met Asn Glu Arg Leu Lys Glu Lys Leu Ala Val Leu Pro Glu Gln Pro
1               5                   10                  15

Gly Cys Tyr Leu Met Lys Asp Lys His Gly Thr Val Ile Tyr Val Gly
            20                  25                  30

Lys Ala Lys Ser Leu Lys Glu Arg Val Arg Ser Tyr Phe Thr Gly Thr
        35                  40                  45

His Asp Gly Lys Thr Gln Arg Leu Val Glu Glu Ile Ala Asp Phe Glu
    50                  55                  60

Tyr Ile Val Thr Ser Ser Asn Ala Glu Ala Leu Ile Leu Glu Met Asn
65                  70                  75                  80

Leu Ile Lys Lys His Asp Pro Lys Tyr Asn Val Met Leu Lys Asp Asp
                85                  90                  95

Lys Ser Tyr Pro Phe Ile Lys Ile Thr Ala Glu Lys His Pro Arg Leu
            100                 105                 110

Leu Ile Thr Arg Lys Val Lys Lys Asp Gly Gly Lys Tyr Phe Gly Pro
        115                 120                 125

Tyr Pro Asn Val Gln Ala Ala Asn Glu Thr Lys Lys Leu Leu Asp Arg
    130                 135                 140

Leu Tyr Pro Leu Arg Lys Cys Ser Thr Leu Pro Ser Arg Ala Cys Leu
145                 150                 155                 160

Tyr Tyr His Met Gly Gln Cys Leu Ala Pro Cys Val His Pro Val Ser
                165                 170                 175

Asp Glu Gln Asn Lys Ala Met Val Glu Gln Ile Val Arg Phe Leu Asn
            180                 185                 190

Gly Gly Tyr Glu Asp Val Lys Arg Glu Leu Ala Glu Lys Met His Glu
        195                 200                 205

Ala Ala Glu Thr Leu Glu Phe Glu Arg Ala Lys Glu Tyr Arg Asp Gln
    210                 215                 220

Ile Ala Ala Ile Glu Met Thr Met Glu Lys Gln Lys Met Met Leu Asn
225                 230                 235                 240

Asp Phe Ile Asp Arg Asp Val Phe Gly Tyr Ala Tyr Asp Lys Gly Trp
                245                 250                 255

Met Cys Val Gln Val Phe Phe Leu Arg Gln Gly Lys Leu Ile Glu Arg
            260                 265                 270

Asp Val Ser Ile Phe Pro Leu Tyr Gln Asp Pro Asp Glu Glu Met Leu
        275                 280                 285
```

```
Thr Phe Leu Gly Gln Phe Tyr Ala Lys Ala His His Leu Lys Pro Lys
    290                 295                 300

Glu Val Val Leu Pro Ser Asp Ile Asp Gly Glu Leu Ala Arg Glu Leu
305                 310                 315                 320

Leu Gly Val Ala Val Val Gln Pro Lys Lys Gly Lys Lys Lys Glu Leu
                325                 330                 335

Val Glu Leu Ala Ser Lys Asn Ala Ala Ile Ala Leu Lys Glu Lys Phe
            340                 345                 350

Tyr Phe Ile Glu Arg Asp Glu Arg Thr Ile Lys Ala Val Glu Arg
        355                 360                 365

Leu Gly Glu Arg Leu Gly Ile Pro Ala Pro Arg Arg Ile Glu Ala Phe
370                 375                 380

Asp Asn Ser Asn Ile Tyr Gly Ala Asp Pro Val Ser Ala Leu Val Val
385                 390                 395                 400

Phe Leu Asp Gly Lys Pro Ala Lys Lys Glu Tyr Arg Lys Tyr Lys Val
                405                 410                 415

Lys Thr Val Ala Gly Pro Asn Asp Tyr Glu Thr Met Arg Glu Val Val
            420                 425                 430

Arg Arg Arg Tyr Thr Arg Val Leu Lys Glu Gly Leu Pro Leu Pro Asp
        435                 440                 445

Leu Ile Ile Ile Asp Gly Gly Lys Gly His Leu Ser Ala Val Arg Asp
450                 455                 460

Val Leu Glu Asn Glu Leu Gly Leu Asp Val Pro Leu Ala Gly Leu Ala
465                 470                 475                 480

Lys Asp Glu Lys His Arg Thr Ser Glu Leu Leu Ala Gly Asp Pro Pro
                485                 490                 495

Asp Val Val Pro Leu Asp Arg Gln Ser Gln Glu Phe Tyr Leu Leu Gln
            500                 505                 510

Arg Ile Gln Asp Glu Val His Arg Phe Ala Val Met Phe His Arg Lys
        515                 520                 525

Thr Arg Gln Lys Thr Met Phe His Ser Val Leu Asp Asp Ile Pro Gly
530                 535                 540

Val Gly Glu Lys Arg Lys Lys Ala Leu Leu Asn Tyr Phe Gly Ser Val
545                 550                 555                 560

Lys Lys Met Lys Glu Ala Thr Val Glu Glu Leu Gln Arg Ala Asn Ile
                565                 570                 575

Pro Arg Ala Val Ala Glu Lys Ile Tyr Glu Lys Leu His Glu
            580                 585                 590

<210> SEQ ID NO 7
<211> LENGTH: 15
<212> TYPE: PRT
<213> ORGANISM: BACILLUS SUBTILIS

<400> SEQUENCE: 7

Gly Leu Ser Gly Ser Gly Lys Ser Ser Leu Ala Phe Asp Thr Ile
1               5                   10                  15

<210> SEQ ID NO 8
<211> LENGTH: 15
<212> TYPE: PRT
<213> ORGANISM: ESCHERICHIA COLI

<400> SEQUENCE: 8

Gly Leu Ser Gly Ser Gly Lys Ser Ser Leu Ala Phe Asp Thr Leu
1               5                   10                  15
```

<210> SEQ ID NO 9
<211> LENGTH: 15
<212> TYPE: PRT
<213> ORGANISM: BACILLUS SUBTILIS

<400> SEQUENCE: 9

```
Gly Val Ser Gly Ser Gly Lys Ser Thr Leu Val Asn Glu Ile Leu
1               5                   10                  15
```

<210> SEQ ID NO 10
<211> LENGTH: 15
<212> TYPE: PRT
<213> ORGANISM: BACILLUS CALDOTENAX

<400> SEQUENCE: 10

```
Gly Val Ser Gly Ser Gly Lys Ser Thr Leu Val Asn Glu Val Leu
1               5                   10                  15
```

<210> SEQ ID NO 11
<211> LENGTH: 15
<212> TYPE: PRT
<213> ORGANISM: ESCHERICHIA COLI

<400> SEQUENCE: 11

```
Gly Cys Ser Gly Ser Gly Lys Ser Thr Leu Ile Asn Asp Thr Leu
1               5                   10                  15
```

<210> SEQ ID NO 12
<211> LENGTH: 28
<212> TYPE: PRT
<213> ORGANISM: BACILLUS SUBTILIS

<400> SEQUENCE: 12

```
Cys Pro His Cys Gly Phe Ser Ile Gly Glu Leu Glu Pro Arg Leu Phe
1               5                   10                  15
Ser Phe Asn Ser Pro Phe Gly Ala Cys Pro Thr Cys
            20                  25
```

<210> SEQ ID NO 13
<211> LENGTH: 28
<212> TYPE: PRT
<213> ORGANISM: BACILLUS CALDOTENAX

<400> SEQUENCE: 13

```
Cys Pro Tyr Cys Gly Phe Ser Ile Gly Glu Leu Glu Pro Arg Leu Phe
1               5                   10                  15
Ser Phe Asn Ser Pro Phe Gly Ala Cys Pro Asp Cys
            20                  25
```

<210> SEQ ID NO 14
<211> LENGTH: 28
<212> TYPE: PRT
<213> ORGANISM: ESCHERICHIA COLI

<400> SEQUENCE: 14

```
Cys Pro Ile Cys Gly Tyr Ser Met Arg Glu Leu Glu Pro Arg Leu Phe
1               5                   10                  15
Ser Phe Asn Asn Pro Ala Gly Ala Cys Pro Thr Cys
            20                  25
```

<210> SEQ ID NO 15
<211> LENGTH: 27

<212> TYPE: PRT
<213> ORGANISM: BACILLUS SUBTILIS

<400> SEQUENCE: 15

```
Cys Glu Ala Cys Arg Gly Asp Gly Ile Ile Lys Ile Glu Met His Phe
1               5                   10                  15

Leu Pro Asp Val Tyr Val Pro Cys Glu Val Cys
            20                  25
```

<210> SEQ ID NO 16
<211> LENGTH: 27
<212> TYPE: PRT
<213> ORGANISM: BACILLUS CALDOTENAX

<400> SEQUENCE: 16

```
Cys Glu Ala Cys His Gly Asp Gly Ile Ile Lys Ile Glu Met His Phe
1               5                   10                  15

Leu Pro Asp Val Tyr Val Pro Cys Glu Val Cys
            20                  25
```

<210> SEQ ID NO 17
<211> LENGTH: 27
<212> TYPE: PRT
<213> ORGANISM: ESCHERICHIA COLI

<400> SEQUENCE: 17

```
Cys Glu Ala Cys Gln Gly Asp Gly Val Ile Lys Val Glu Met His Phe
1               5                   10                  15

Leu Pro Asp Ile Tyr Val Pro Cys Asp Gln Cys
            20                  25
```

<210> SEQ ID NO 18
<211> LENGTH: 665
<212> TYPE: PRT
<213> ORGANISM: THERMUS THERMOPHILUS

<400> SEQUENCE: 18

```
Met Thr Phe Arg Tyr Arg Gly Pro Ser Pro Lys Gly Asp Gln Pro Lys
1               5                   10                  15

Ala Ile Ala Gly Leu Val Glu Ala Leu Arg Asp Gly Glu Arg Phe Val
            20                  25                  30

Thr Leu Leu Gly Ala Thr Gly Thr Gly Lys Thr Val Thr Met Ala Lys
        35                  40                  45

Val Ile Glu Ala Leu Gly Arg Pro Ala Leu Val Leu Ala Pro Asn Lys
    50                  55                  60

Ile Leu Ala Ala Gln Leu Ala Ala Glu Phe Arg Glu Leu Phe Pro Glu
65                  70                  75                  80

Asn Ala Val Glu Tyr Phe Ile Ser Tyr Tyr Asp Tyr Tyr Gln Pro Glu
                85                  90                  95

Ala Tyr Val Pro Gly Lys Asp Leu Tyr Ile Glu Lys Asp Ala Ser Ile
            100                 105                 110

Asn Pro Glu Ile Glu Arg Leu Arg His Ser Thr Thr Arg Ser Leu Leu
        115                 120                 125

Thr Arg Arg Asp Val Ile Val Val Ala Ser Val Ser Ala Ile Tyr Gly
    130                 135                 140

Leu Gly Asp Pro Arg Glu Tyr Arg Ala Arg Asn Leu Val Val Glu Arg
145                 150                 155                 160

Gly Lys Pro Tyr Pro Arg Glu Val Leu Leu Glu Arg Leu Leu Glu Leu
                165                 170                 175
```

-continued

```
Gly Tyr Gln Arg Asn Asp Ile Asp Leu Ser Pro Gly Arg Phe Arg Ala
            180                 185                 190
Lys Gly Glu Val Leu Glu Ile Phe Pro Ala Tyr Glu Thr Glu Pro Ile
        195                 200                 205
Arg Val Glu Leu Phe Gly Asp Glu Val Glu Arg Ile Ser Gln Val His
    210                 215                 220
Pro Val Thr Gly Glu Arg Leu Arg Glu Leu Pro Gly Phe Val Leu Phe
225                 230                 235                 240
Pro Ala Thr His Tyr Leu Ser Pro Glu Gly Leu Glu Glu Ile Leu Lys
                245                 250                 255
Glu Ile Glu Lys Glu Leu Trp Glu Arg Val Arg Tyr Phe Glu Glu Arg
            260                 265                 270
Gly Glu Val Leu Tyr Ala Gln Arg Leu Lys Glu Arg Thr Leu Tyr Asp
        275                 280                 285
Leu Glu Met Leu Arg Val Met Gly Thr Cys Pro Gly Val Glu Asn Tyr
    290                 295                 300
Ala Arg Tyr Phe Thr Gly Lys Ala Pro Gly Glu Pro Pro Tyr Thr Leu
305                 310                 315                 320
Leu Asp Tyr Phe Pro Glu Asp Phe Leu Val Phe Leu Asp Glu Ser His
                325                 330                 335
Val Thr Val Pro Gln Leu Gln Gly Met Tyr Arg Gly Asp Tyr Ala Arg
            340                 345                 350
Lys Lys Thr Leu Val Asp Tyr Gly Phe Arg Leu Pro Ser Ala Leu Asp
        355                 360                 365
Asn Arg Pro Leu Arg Phe Glu Glu Phe Leu Glu Arg Val Ser Gln Val
    370                 375                 380
Val Phe Val Ser Ala Thr Pro Gly Pro Phe Glu Leu Ala His Ser Gly
385                 390                 395                 400
Arg Val Val Glu Gln Ile Ile Arg Pro Thr Gly Leu Leu Asp Pro Leu
                405                 410                 415
Val Arg Val Lys Pro Thr Glu Asn Gln Ile Leu Asp Leu Met Glu Gly
            420                 425                 430
Ile Arg Glu Arg Ala Ala Arg Gly Glu Arg Thr Leu Val Thr Val Leu
        435                 440                 445
Thr Val Arg Met Ala Glu Glu Leu Thr Ser Phe Leu Val Glu His Gly
    450                 455                 460
Ile Arg Ala Arg Tyr Leu His His Glu Leu Asp Ala Phe Lys Arg Gln
465                 470                 475                 480
Ala Leu Ile Arg Asp Leu Arg Leu Gly His Tyr Asp Cys Leu Val Gly
                485                 490                 495
Ile Asn Leu Leu Arg Glu Gly Leu Asp Ile Pro Glu Val Ser Leu Val
            500                 505                 510
Ala Ile Leu Asp Ala Asp Lys Glu Gly Phe Leu Arg Ser Glu Arg Ser
        515                 520                 525
Leu Ile Gln Thr Ile Gly Arg Ala Ala Arg Asn Ala Arg Gly Glu Val
    530                 535                 540
Trp Leu Tyr Ala Asp Arg Val Ser Glu Ala Met Gln Arg Ala Ile Glu
545                 550                 555                 560
Glu Thr Asn Arg Arg Ala Leu Gln Glu Ala Tyr Asn Leu Glu His
                565                 570                 575
Gly Ile Thr Pro Glu Thr Val Arg Lys Glu Val Arg Ala Val Ile Arg
            580                 585                 590
```

```
Pro Glu Gly Tyr Glu Glu Ala Pro Leu Glu Ala Asp Leu Ser Gly Glu
            595                 600                 605

Asp Leu Arg Glu Arg Ile Ala Glu Leu Glu Leu Ala Met Trp Gln Ala
    610                 615                 620

Ala Glu Ala Leu Asp Phe Glu Arg Ala Ala Arg Leu Arg Asp Glu Ile
625                 630                 635                 640

Arg Ala Leu Glu Ala Arg Leu Gln Gly Val Arg Ala Pro Glu Pro Val
            645                 650                 655

Pro Gly Gly Arg Lys Arg Lys Arg
            660                 665

<210> SEQ ID NO 19
<211> LENGTH: 673
<212> TYPE: PRT
<213> ORGANISM: ESCHERICHIA COLI

<400> SEQUENCE: 19

Met Ser Lys Pro Phe Lys Leu Asn Ser Ala Phe Lys Pro Ser Gly Asp
1               5                   10                  15

Gln Pro Glu Ala Ile Arg Arg Leu Glu Glu Gly Leu Glu Asp Gly Leu
            20                  25                  30

Ala His Gln Thr Leu Leu Gly Val Thr Gly Ser Gly Lys Thr Phe Thr
        35                  40                  45

Ile Ala Asn Val Ile Ala Asp Leu Gln Arg Pro Thr Met Val Leu Ala
    50                  55                  60

Pro Asn Lys Thr Leu Ala Ala Gln Leu Tyr Gly Glu Met Lys Glu Phe
65                  70                  75                  80

Phe Pro Glu Asn Ala Val Glu Tyr Phe Val Ser Tyr Tyr Asp Tyr Tyr
                85                  90                  95

Gln Pro Glu Ala Tyr Val Pro Ser Ser Asp Thr Phe Ile Glu Lys Asp
            100                 105                 110

Ala Ser Val Asn Glu His Ile Glu Gln Met Arg Leu Ser Ala Thr Lys
        115                 120                 125

Ala Met Leu Glu Arg Arg Asp Val Val Val Ala Ser Val Ser Ala
    130                 135                 140

Ile Tyr Gly Leu Gly Asp Pro Asp Leu Tyr Leu Lys Met Met Leu His
145                 150                 155                 160

Leu Thr Val Gly Met Ile Ile Asp Gln Arg Ala Ile Leu Arg Arg Leu
                165                 170                 175

Ala Glu Leu Gln Tyr Ala Arg Asn Asp Gln Ala Phe Gln Arg Gly Thr
            180                 185                 190

Phe Arg Val Arg Gly Glu Val Ile Asp Ile Phe Pro Ala Glu Ser Asp
        195                 200                 205

Asp Ile Ala Leu Arg Val Glu Leu Phe Asp Glu Glu Val Glu Arg Leu
    210                 215                 220

Ser Leu Phe Asp Pro Leu Thr Gly Gln Ile Val Ser Thr Ile Pro Arg
225                 230                 235                 240

Phe Thr Ile Tyr Pro Lys Thr His Tyr Val Thr Pro Arg Glu Arg Ile
                245                 250                 255

Val Gln Ala Met Glu Glu Ile Lys Glu Glu Leu Ala Ala Arg Arg Lys
            260                 265                 270

Val Leu Leu Glu Asn Asn Lys Leu Leu Glu Glu Gln Arg Leu Thr Gln
        275                 280                 285

Arg Thr Gln Phe Asp Leu Glu Met Met Asn Glu Leu Gly Tyr Cys Ser
    290                 295                 300
```

```
Gly Ile Glu Asn Tyr Ser Arg Phe Leu Ser Gly Arg Gly Pro Gly Glu
305                 310                 315                 320

Pro Pro Pro Thr Leu Phe Asp Tyr Leu Pro Ala Asp Gly Leu Leu Val
            325                 330                 335

Val Asp Glu Ser His Val Thr Ile Pro Gln Ile Gly Met Tyr Arg
            340                 345                 350

Gly Asp Arg Ala Arg Lys Glu Thr Leu Val Glu Tyr Gly Phe Arg Leu
            355                 360                 365

Pro Ser Ala Leu Asp Asn Arg Pro Leu Lys Phe Glu Glu Phe Glu Ala
370                 375                 380

Leu Ala Pro Gln Thr Ile Tyr Val Ser Ala Thr Pro Gly Asn Tyr Glu
385                 390                 395                 400

Leu Glu Lys Ser Gly Gly Asp Val Val Asp Gln Val Val Arg Pro Thr
            405                 410                 415

Gly Leu Leu Asp Pro Ile Ile Glu Val Arg Pro Val Ala Thr Gln Val
            420                 425                 430

Asp Asp Leu Leu Ser Glu Ile Arg Gln Arg Ala Ala Ile Asn Glu Arg
            435                 440                 445

Val Leu Val Thr Thr Leu Thr Lys Arg Met Ala Glu Asp Leu Thr Glu
450                 455                 460

Tyr Leu Glu Glu His Gly Glu Arg Val Arg Tyr Leu His Ser Asp Ile
465                 470                 475                 480

Asp Thr Val Glu Arg Met Glu Ile Ile Arg Asp Leu Arg Leu Gly Glu
            485                 490                 495

Phe Asp Val Leu Val Gly Ile Asn Leu Leu Arg Glu Gly Leu Asp Met
            500                 505                 510

Pro Glu Val Ser Leu Val Ala Ile Leu Asp Ala Asp Lys Glu Gly Phe
            515                 520                 525

Leu Arg Ser Glu Arg Ser Leu Ile Gln Thr Ile Gly Arg Ala Ala Arg
            530                 535                 540

Asn Val Asn Gly Lys Ala Ile Leu Tyr Gly Asp Lys Ile Thr Pro Ser
545                 550                 555                 560

Met Ala Lys Ala Ile Gly Glu Thr Glu Arg Arg Arg Glu Lys Gln Gln
            565                 570                 575

Lys Tyr Asn Glu Glu His Gly Ile Thr Pro Gln Gly Leu Asn Lys Lys
            580                 585                 590

Val Val Asp Ile Leu Ala Leu Gly Gln Asn Ile Ala Lys Thr Lys Ala
            595                 600                 605

Lys Gly Arg Gly Lys Ser Arg Pro Ile Val Glu Pro Asp Asn Val Pro
610                 615                 620

Met Asp Met Ser Pro Lys Ala Leu Gln Gln Lys Ile His Glu Leu Glu
625                 630                 635                 640

Gly Leu Met Met Gln His Ala Gln Asn Leu Glu Phe Glu Glu Ala Ala
            645                 650                 655

Gln Ile Arg Asp Gln Leu His Gln Leu Arg Glu Leu Phe Ile Ala Ala
            660                 665                 670

Ser
```

<210> SEQ ID NO 20
<211> LENGTH: 33
<212> TYPE: DNA
<213> ORGANISM: ARTIFICIAL
<220> FEATURE:
<223> OTHER INFORMATION: primer

<400> SEQUENCE: 20
gcgaccgcat atggataaaa ttgtcgtcaa agg 33

<210> SEQ ID NO 21
<211> LENGTH: 37
<212> TYPE: DNA
<213> ORGANISM: ARTIFICIAL
<220> FEATURE:
<223> OTHER INFORMATION: primer

<400> SEQUENCE: 21
tctcccgctc ttccgcacgc cttcaccgct tcatatt 37

<210> SEQ ID NO 22
<211> LENGTH: 24
<212> TYPE: DNA
<213> ORGANISM: ARTIFICIAL
<220> FEATURE:
<223> OTHER INFORMATION: primer

<400> SEQUENCE: 22
cagctcaatg tcttccgtca actc 24

<210> SEQ ID NO 23
<211> LENGTH: 24
<212> TYPE: DNA
<213> ORGANISM: ARTIFICIAL
<220> FEATURE:
<223> OTHER INFORMATION: primer

<400> SEQUENCE: 23
gagttgacgg aagacattga gctg 24

<210> SEQ ID NO 24
<211> LENGTH: 24
<212> TYPE: DNA
<213> ORGANISM: ARTIFICIAL
<220> FEATURE:
<223> OTHER INFORMATION: primer

<400> SEQUENCE: 24
cgcaatatta cccgcagctg ctcg 24

<210> SEQ ID NO 25
<211> LENGTH: 22
<212> TYPE: DNA
<213> ORGANISM: ARTIFICIAL
<220> FEATURE:
<223> OTHER INFORMATION: primer

<400> SEQUENCE: 25
cccttcaatc gcatcgacgt cc 22

<210> SEQ ID NO 26
<211> LENGTH: 36
<212> TYPE: DNA
<213> ORGANISM: ARTIFICIAL
<220> FEATURE:
<223> OTHER INFORMATION: primer

<400> SEQUENCE: 26
ctcctatcat atggtggagg gccgttttca attagt 36

<210> SEQ ID NO 27

```
<211> LENGTH: 35
<212> TYPE: DNA
<213> ORGANISM: ARTIFICIAL
<220> FEATURE:
<223> OTHER INFORMATION: primer

<400> SEQUENCE: 27
tacactccat atggagggcc gttttcaatt agtgg                              35

<210> SEQ ID NO 28
<211> LENGTH: 39
<212> TYPE: DNA
<213> ORGANISM: ARTIFICIAL
<220> FEATURE:
<223> OTHER INFORMATION: primer

<400> SEQUENCE: 28
gtacagtgct cttccgcacc cttccgcttt caattcgaa                          39

<210> SEQ ID NO 29
<211> LENGTH: 28
<212> TYPE: DNA
<213> ORGANISM: ARTIFICIAL
<220> FEATURE:
<223> OTHER INFORMATION: primer
<220> FEATURE:
<221> NAME/KEY: misc_feature
<222> LOCATION: (23)..(23)
<223> OTHER INFORMATION: any nucleotide

<400> SEQUENCE: 29
gcggatccgt batytaygtb ggnaargc                                      28

<210> SEQ ID NO 30
<211> LENGTH: 6
<212> TYPE: PRT
<213> ORGANISM: BACILLUS CALDOTENAX

<400> SEQUENCE: 30

Val Ile Tyr Val Gly Lys
1               5

<210> SEQ ID NO 31
<211> LENGTH: 25
<212> TYPE: DNA
<213> ORGANISM: ARTIFICIAL
<220> FEATURE:
<223> OTHER INFORMATION: primer
<220> FEATURE:
<221> NAME/KEY: misc_feature
<222> LOCATION: (14)..(14)
<223> OTHER INFORMATION: any nucleotide
<220> FEATURE:
<221> NAME/KEY: misc_feature
<222> LOCATION: (17)..(17)
<223> OTHER INFORMATION: any nucleotide

<400> SEQUENCE: 31
gcgaattccc rttnccnccr tcrat                                         25

<210> SEQ ID NO 32
<211> LENGTH: 6
<212> TYPE: PRT
<213> ORGANISM: BACILLUS CALDOTENAX

<400> SEQUENCE: 32

Ile Asp Gly Gly Lys Gly
1               5
```

<210> SEQ ID NO 33
<211> LENGTH: 22
<212> TYPE: DNA
<213> ORGANISM: ARTIFICIAL
<220> FEATURE:
<223> OTHER INFORMATION: primer

<400> SEQUENCE: 33
catcgcacat cagagctttt gg                                              22

<210> SEQ ID NO 34
<211> LENGTH: 22
<212> TYPE: DNA
<213> ORGANISM: ARTIFICIAL
<220> FEATURE:
<223> OTHER INFORMATION: primer

<400> SEQUENCE: 34
tcagcgatct cctcaacaag cc                                              22

<210> SEQ ID NO 35
<211> LENGTH: 37
<212> TYPE: DNA
<213> ORGANISM: ARTIFICIAL
<220> FEATURE:
<223> OTHER INFORMATION: primer

<400> SEQUENCE: 35
aattacccat atgaacgagc gtctgaaaga aaaactg                              37

<210> SEQ ID NO 36
<211> LENGTH: 26
<212> TYPE: DNA
<213> ORGANISM: ARTIFICIAL
<220> FEATURE:
<223> OTHER INFORMATION: primer

<400> SEQUENCE: 36
gcattggccc atgtggtaat acaaac                                          26

<210> SEQ ID NO 37
<211> LENGTH: 26
<212> TYPE: DNA
<213> ORGANISM: ARTIFICIAL
<220> FEATURE:
<223> OTHER INFORMATION: primer

<400> SEQUENCE: 37
gtttgtatta ccacatgggc caatgc                                          26

<210> SEQ ID NO 38
<211> LENGTH: 45
<212> TYPE: DNA
<213> ORGANISM: ARTIFICIAL
<220> FEATURE:
<223> OTHER INFORMATION: primer

<400> SEQUENCE: 38
tctcccgctc ttccgcattc atgcagtttt tcatagattt ctcc                      45

<210> SEQ ID NO 39
<211> LENGTH: 18
<212> TYPE: PRT
<213> ORGANISM: ARTIFICIAL
<220> FEATURE:

```
<223> OTHER INFORMATION: DNA binding consensus sequence
<220> FEATURE:
<221> NAME/KEY: misc_feature
<222> LOCATION: (2)..(3)
<223> OTHER INFORMATION: any amino acid
<220> FEATURE:
<221> NAME/KEY: misc_feature
<222> LOCATION: (5)..(14)
<223> OTHER INFORMATION: any amino acid
<220> FEATURE:
<221> NAME/KEY: misc_feature
<222> LOCATION: (16)..(17)
<223> OTHER INFORMATION: any amino acid

<400> SEQUENCE: 39

Cys Xaa Xaa Cys Xaa Xaa Xaa Xaa Xaa Xaa Xaa Xaa Xaa Xaa Cys Xaa
 1               5                   10                  15

Xaa Cys

<210> SEQ ID NO 40
<211> LENGTH: 15
<212> TYPE: PRT
<213> ORGANISM: ARTIFICIAL
<220> FEATURE:
<223> OTHER INFORMATION: polypeptide consensus sequence
<220> FEATURE:
<221> NAME/KEY: misc_feature
<222> LOCATION: (2)..(5)
<223> OTHER INFORMATION: any amino acid
<220> FEATURE:
<221> NAME/KEY: misc_feature
<222> LOCATION: (8)..(8)
<223> OTHER INFORMATION: T or S
<220> FEATURE:
<221> NAME/KEY: misc_feature
<222> LOCATION: (9)..(14)
<223> OTHER INFORMATION: I or Y
<220> FEATURE:
<221> NAME/KEY: misc_feature
<222> LOCATION: (15)..(15)
<223> OTHER INFORMATION: I or Y

<400> SEQUENCE: 40

Gly Xaa Xaa Xaa Xaa Gly Lys Xaa Xaa Xaa Xaa Xaa Xaa Xaa Xaa
 1               5                   10                  15

<210> SEQ ID NO 41
<211> LENGTH: 50
<212> TYPE: DNA
<213> ORGANISM: ARTIFICIAL
<220> FEATURE:
<223> OTHER INFORMATION: oligonucleotide
<220> FEATURE:
<221> NAME/KEY: misc_feature
<222> LOCATION: (26)..(26)
<223> OTHER INFORMATION: fluorescein-label

<400> SEQUENCE: 41
gactacgtac tgttacggct ccatcnctac cgcaatcagg ccagatctgc            50

<210> SEQ ID NO 42
<211> LENGTH: 35
<212> TYPE: DNA
<213> ORGANISM: ARTIFICIAL
<220> FEATURE:
<223> OTHER INFORMATION: oligonucleotide

<400> SEQUENCE: 42
aaatgtatct aatggtcaaa ctaaatctac tcgtt                            35
```

```
<210> SEQ ID NO 43
<211> LENGTH: 26
<212> TYPE: DNA
<213> ORGANISM: ARTIFICIAL
<220> FEATURE:
<223> OTHER INFORMATION: oligonucleotide
<220> FEATURE:
<221> NAME/KEY: misc_feature
<222> LOCATION: (12)..(12)
<223> OTHER INFORMATION: fluorescein adduct

<400> SEQUENCE: 43
tagatttagt tngaccatta gataca                                              26

<210> SEQ ID NO 44
<211> LENGTH: 50
<212> TYPE: DNA
<213> ORGANISM: ARTIFICIAL
<220> FEATURE:
<223> OTHER INFORMATION: oligonucleotide

<400> SEQUENCE: 44
gactacgtac tgttacggct ccatcgctac cgcaatcagg ccagatctgc                    50

<210> SEQ ID NO 45
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 45

Cys Pro Tyr Cys
1

<210> SEQ ID NO 46
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 46

Cys Pro His Cys
1

<210> SEQ ID NO 47
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 47

Cys Pro Gly Thr
1

<210> SEQ ID NO 48
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 48

Cys Pro Glu His
1
```

```
<210> SEQ ID NO 49
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 49

Cys Pro Asn Gly
1

<210> SEQ ID NO 50
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 50

Cys Pro Ile Cys
1

<210> SEQ ID NO 51
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 51

Cys Asp Gln Cys
1

<210> SEQ ID NO 52
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 52

Cys Asp Lys Cys
1

<210> SEQ ID NO 53
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 53

Cys Phe Lys Cys
1

<210> SEQ ID NO 54
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 54

Cys Pro Asp Cys
1
```

```
<210> SEQ ID NO 55
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 55

Cys Pro Thr Cys
1

<210> SEQ ID NO 56
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 56

Cys Pro Glu Cys
1

<210> SEQ ID NO 57
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 57

Cys Pro Ala Cys
1

<210> SEQ ID NO 58
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 58

Cys Pro Ser Cys
1

<210> SEQ ID NO 59
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 59

Cys Pro Asn Cys
1

<210> SEQ ID NO 60
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 60

Cys Glu Tyr Cys
1

<210> SEQ ID NO 61
```

-continued

```
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 61

Cys Ser Tyr Cys
1

<210> SEQ ID NO 62
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 62

Cys Glu Ser Cys
1

<210> SEQ ID NO 63
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 63

Cys Glu Ala Cys
1

<210> SEQ ID NO 64
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 64

Cys Glu His Cys
1

<210> SEQ ID NO 65
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 65

Cys Glu Lys Cys
1

<210> SEQ ID NO 66
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 66

Cys Glu Val Cys
1

<210> SEQ ID NO 67
<211> LENGTH: 4
```

```
<212> TYPE: PRT
<213> ORGANISM: ARTIFICIAL
<220> FEATURE:
<223> OTHER INFORMATION: zinc finger binding motif

<400> SEQUENCE: 67

Cys Glu Tyr Cys
1

<210> SEQ ID NO 68
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 68

Cys Asp Val Cys
1

<210> SEQ ID NO 69
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 69

Cys Glu Met Cys
1

<210> SEQ ID NO 70
<211> LENGTH: 4
<212> TYPE: PRT
<213> ORGANISM: ARTIFICIAL
<220> FEATURE:
<223> OTHER INFORMATION: zinc finger binding motif

<400> SEQUENCE: 70

Cys Asp Ser Cys
1

<210> SEQ ID NO 71
<211> LENGTH: 4
<212> TYPE: PRT
<213> ORGANISM: ARTIFICIAL
<220> FEATURE:
<223> OTHER INFORMATION: zinc finger binding motif
<220> FEATURE:
<221> NAME/KEY: X
<222> LOCATION: (2)..(3)
<223> OTHER INFORMATION: amino acid
<220> FEATURE:
<221> NAME/KEY: misc_feature
<222> LOCATION: (2)..(3)
<223> OTHER INFORMATION: Xaa can be any naturally occurring amino acid

<400> SEQUENCE: 71

Cys Xaa Xaa Cys
1
```